United States Patent
Krauss-Etschmann et al.

(10) Patent No.: US 10,857,128 B2
(45) Date of Patent: Dec. 8, 2020

(54) METHODS AND COMPOSITIONS FOR TREATING INFLAMMATORY DISEASES

(71) Applicant: Helmholtz Zentrum München Deutsches Forschungszentrum für Gesundheit und Umwelt (GmbH), Neuherberg (DE)

(72) Inventors: Susanne Krauss-Etschmann, Hamburg (DE); Anton Hartmann, Forchheim (DE); Philippe Schmitt-Kopplin, Marzling (DE); Michael Schloter, Inning (DE)

(73) Assignee: Helmholtz Zentrum München Deutsches Forschungszentrum für Gesundheit und Umwelt (GmbH), Neuherberg (DE)

(*) Notice: Subject to any disclaimer, the term of this patent is extended or adjusted under 35 U.S.C. 154(b) by 0 days.

(21) Appl. No.: 15/708,902

(22) Filed: Sep. 19, 2017

(65) Prior Publication Data

US 2019/0083461 A1 Mar. 21, 2019

(51) Int. Cl.
| | | |
|---|---|---|
| *A61K 31/405* | (2006.01) | |
| *A61P 37/08* | (2006.01) | |
| *A61P 11/06* | (2006.01) | |
| *A23L 33/175* | (2016.01) | |
| *A23L 33/00* | (2016.01) | |
| *A23L 33/10* | (2016.01) | |

(52) U.S. Cl.
CPC ............ *A61K 31/405* (2013.01); *A23L 33/10* (2016.08); *A23L 33/175* (2016.08); *A23L 33/30* (2016.08); *A23L 33/40* (2016.08); *A61P 11/06* (2018.01); *A61P 37/08* (2018.01); *A23V 2002/00* (2013.01)

(58) Field of Classification Search
CPC ................. A61K 31/405; A23V 2250/065
See application file for complete search history.

(56) References Cited

U.S. PATENT DOCUMENTS 3,717,477 A * 2/1973 Nonomiya .............. A23L 27/31
426/548
3,988,466 A * 10/1976 Takagi ................. A61K 31/405
514/561

OTHER PUBLICATIONS

Shibata et al. (Biosci. Biotechnol. Biochem. 63, 206-209, 1999). (Year: 1999).*
Kepert et al., J Allergy Clin Immunol, May 2017 (Year: 2017).*
Cava, et al., (2011) "Distinct pathways for modification of the bacterial cell wall by non-canonical o-amino acids", The EMBO Journal, 30: 3442-3453.
Hashimoto, et al. (1993) "Embryonic Development and Postnatal Changes in Free D-Aspartate and D-Serine in the Human Prefrontal Cortex", Journal of Neurochemistry, 61(1): 348-351.
Treibwasser et al., ( 1976) "Metabolism of D- and L-Tryptophan in Dogs", J. Nutr., 106: 642-652.
Kolodkin-Gal et al., (2010) "D-Amino Acids Trigger Biofilm Disassembly", Science, 328: 627-629.
Visser et al. (2011) "A sensitive and simple ultra-high-performance-liquid chromatography-tandem mass spectrometry based method for the quantification of D-amino acids in body fluids", Journal of Chromatography A, 1218: 7130-7136.
Kepert et al., (2017) "D-tryptophan from probiotic bacteria influences the gut microbiome and allergic airway disease", J. Allergy Clin. Immunol., 139(5): 1525-1535.
"Rats and Mice Weights", Animal Resources Centre, retrieved from www.arc.wa.gov.au/?page_id=125, 2018, 3 pages.
"Anthropometric Reference Data for Children and Adults: United States, 2011-2014", Vital and Health Statistics, Series 3, No. 9, U.S Department of Health and Human Services, Centers for Disease Control and Prevention, Aug. 2016, 46 pages.
"Median Lethal Dose", Wikipedia, retrieved from www.en.wikipedia.org/wiki/Median_lethal_dose, 2018, 8 pages.

* cited by examiner

*Primary Examiner* — Theodore R. West
(74) *Attorney, Agent, or Firm* — Kagan Binder, PLLC

(57) ABSTRACT

The present invention relates to a food composition and a pharmaceutical comprising D-tryptophan. The present invention further relates to D-tryptophan for use in the treatment, prevention or amelioration of a diseases associated with $T_{reg}$ or $T_H2$ cells, such as allergy and in particular asthma.

21 Claims, 26 Drawing Sheets

Specification includes a Sequence Listing.

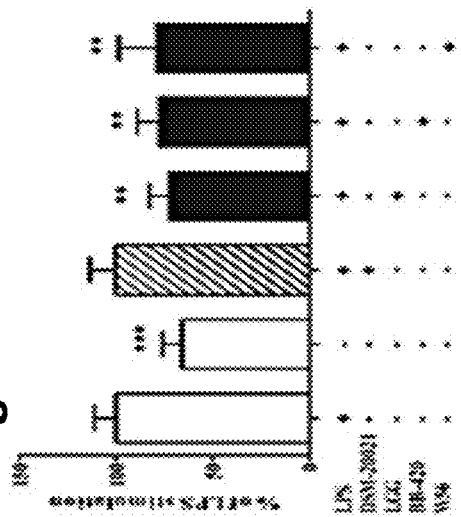
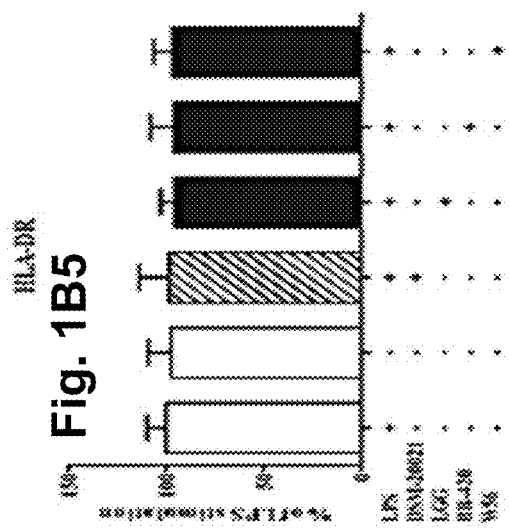
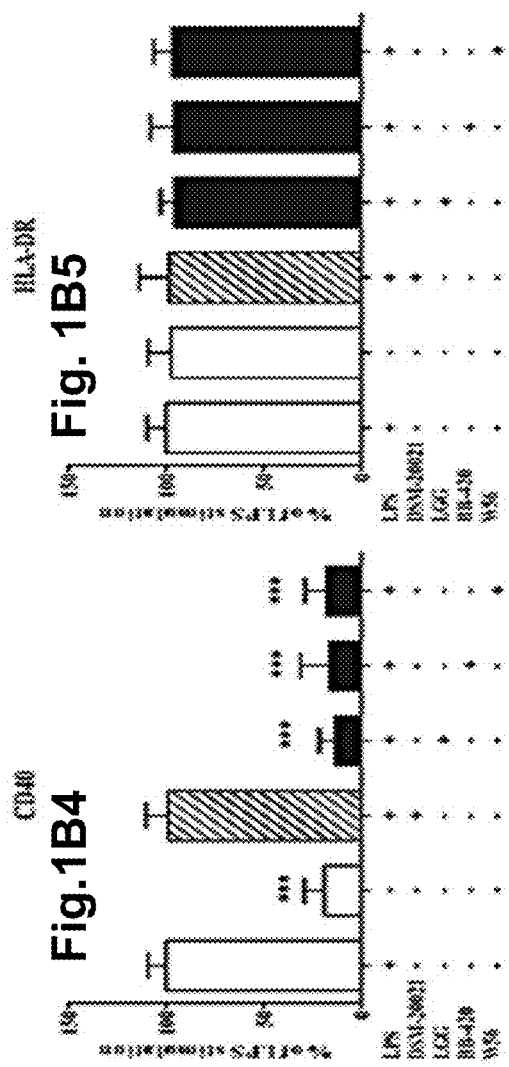

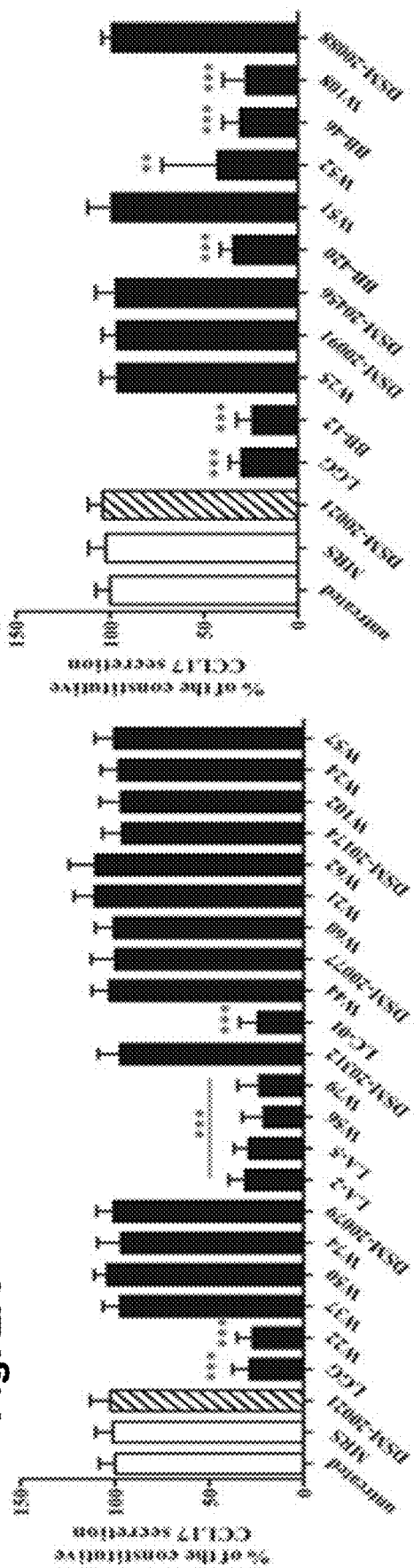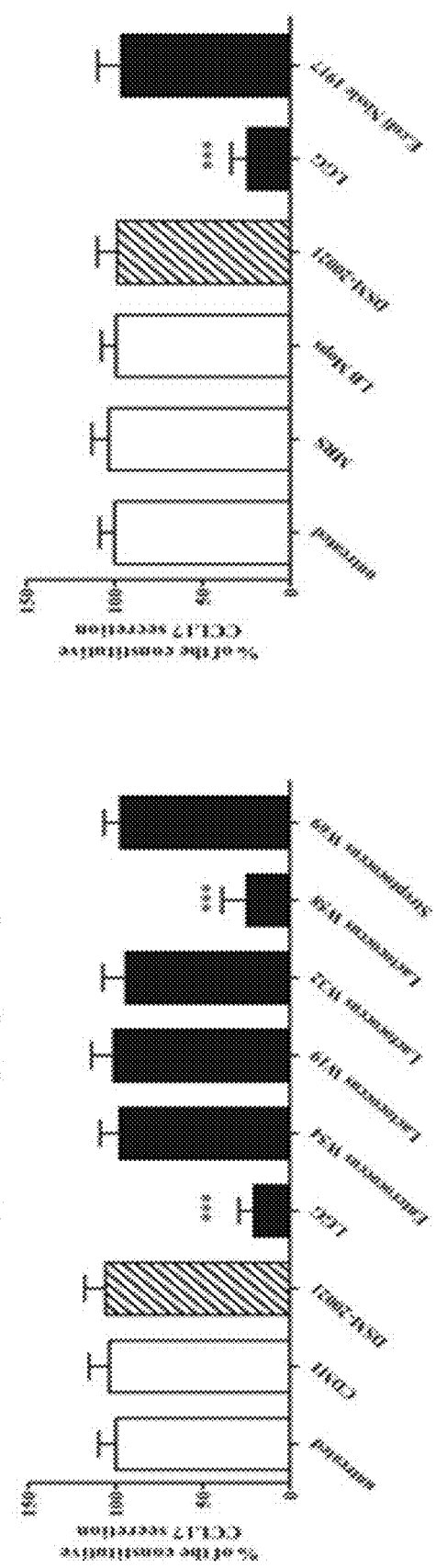

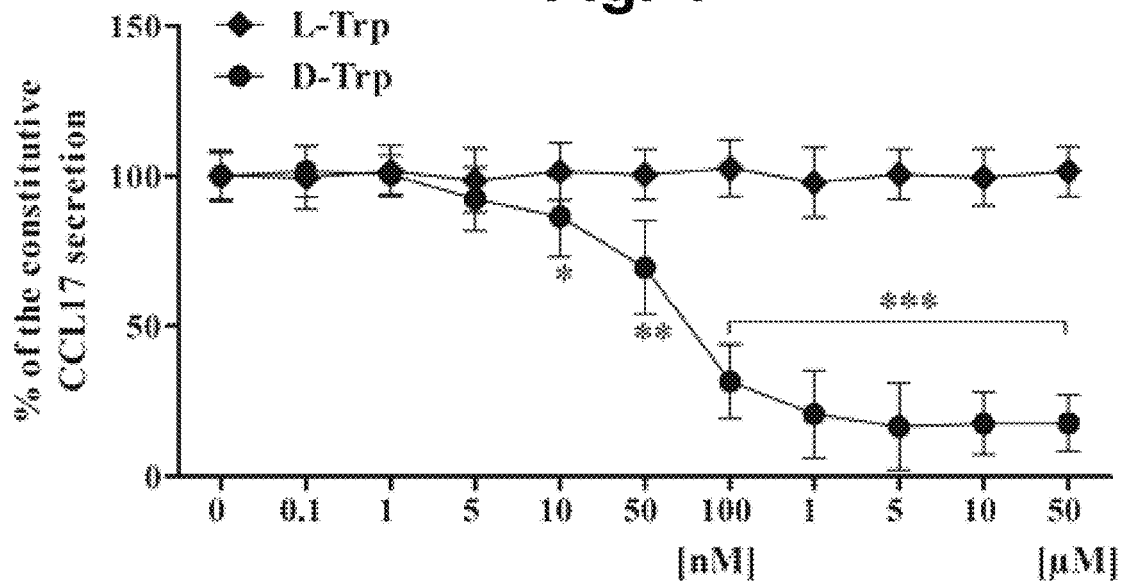
Fig. 4
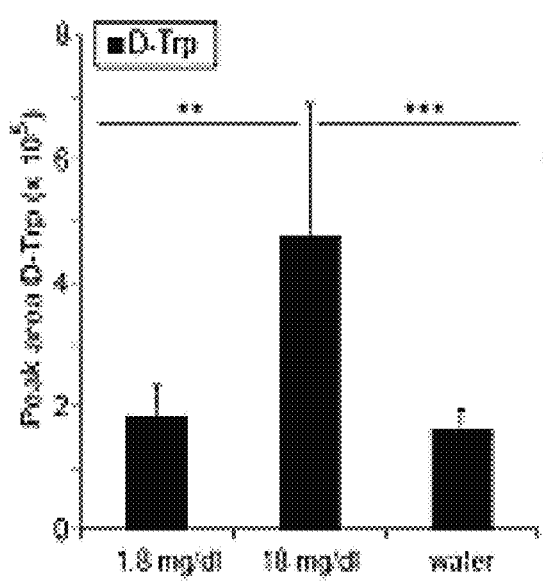
Fig. 5A1
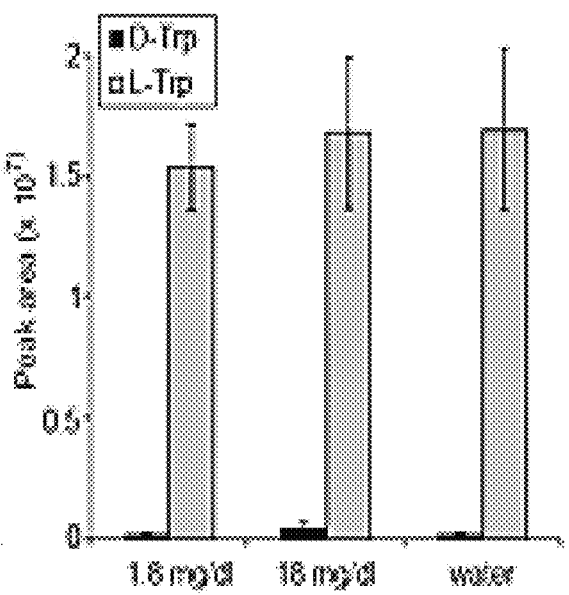
Fig. 5A2

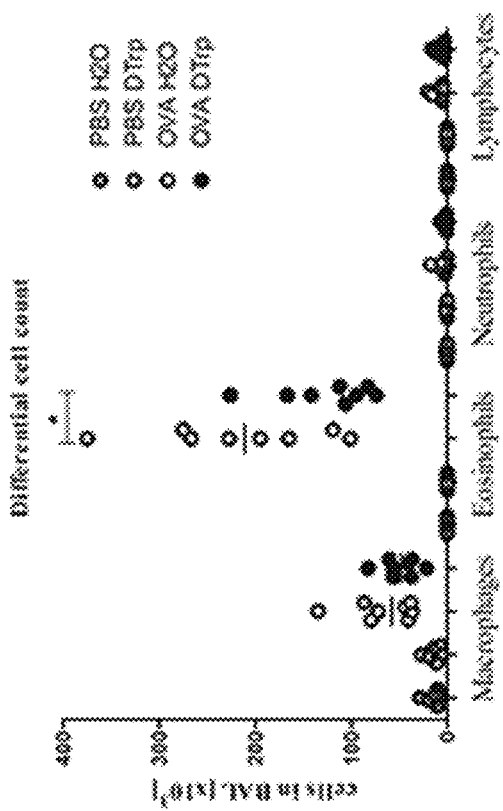
Fig. 5B
Fig. 5C
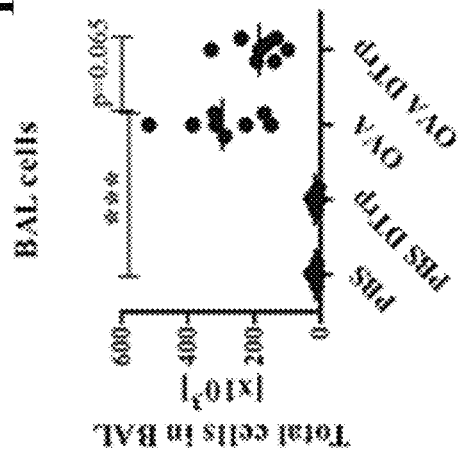
Fig. 5D

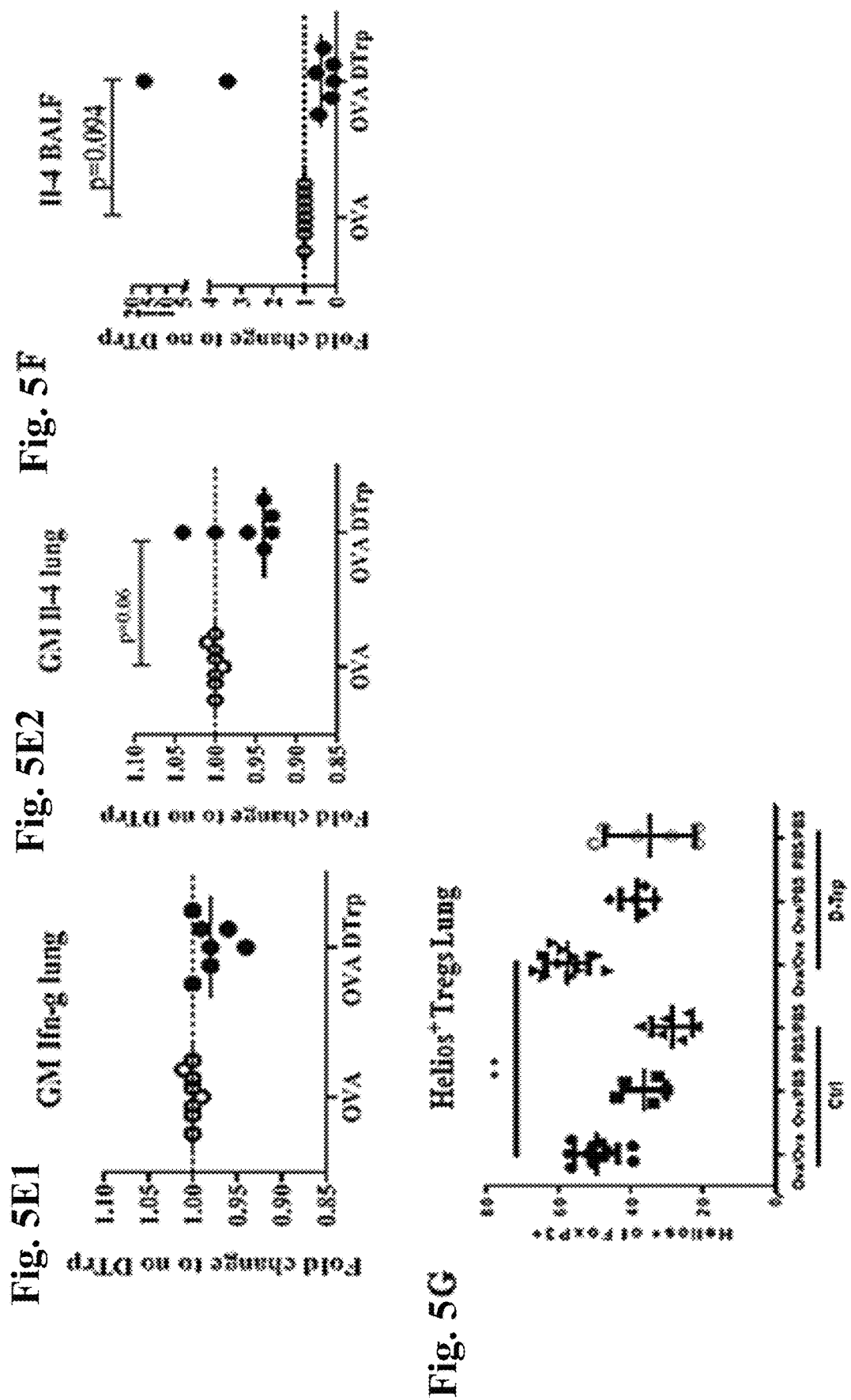

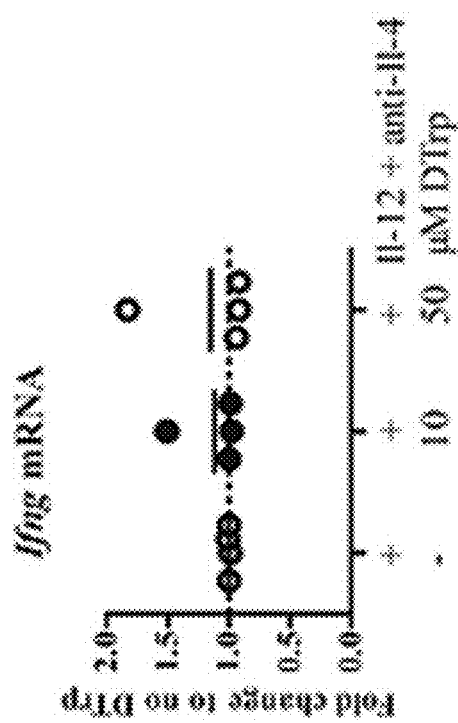
Fig. 6A2
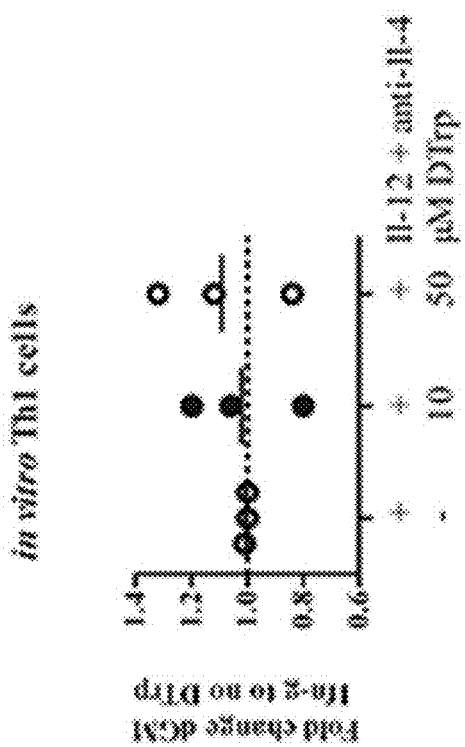
Fig. 6A1

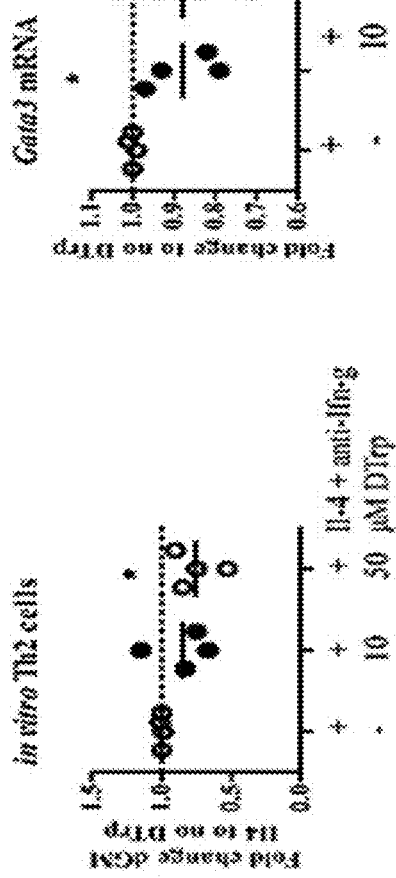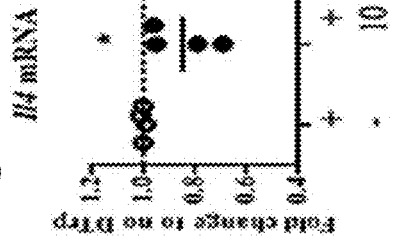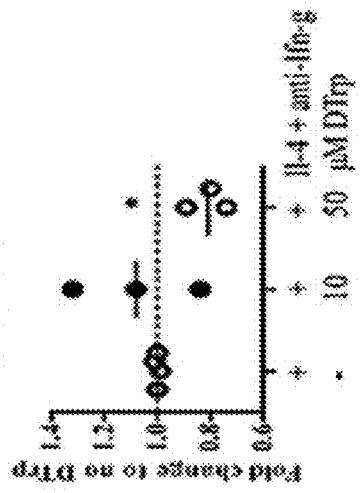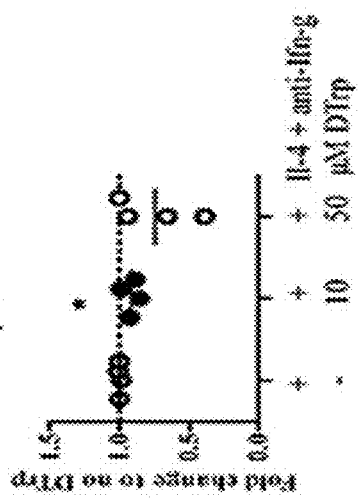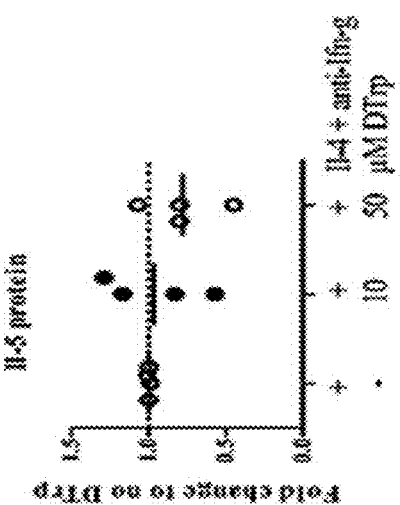

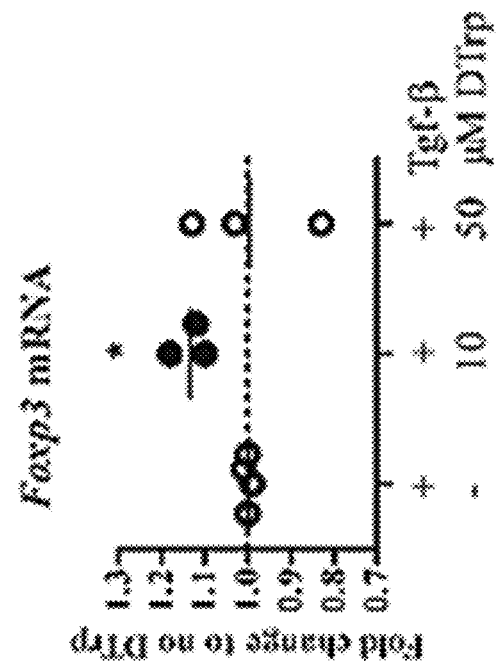
Fig. 6C1
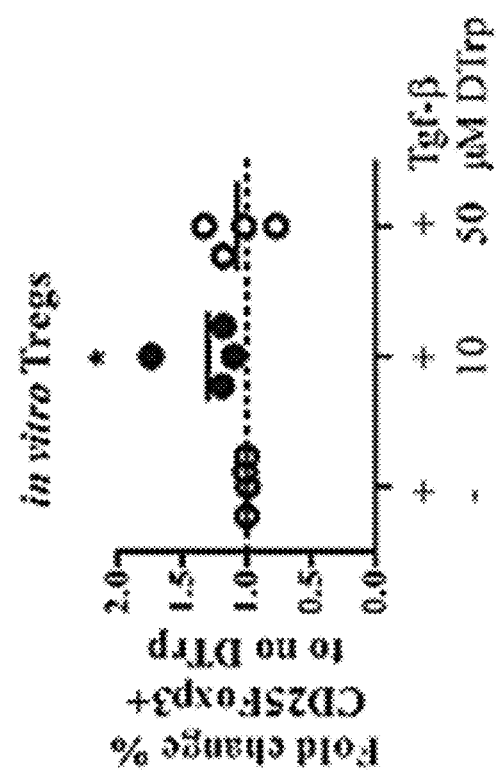
Fig. 6C2

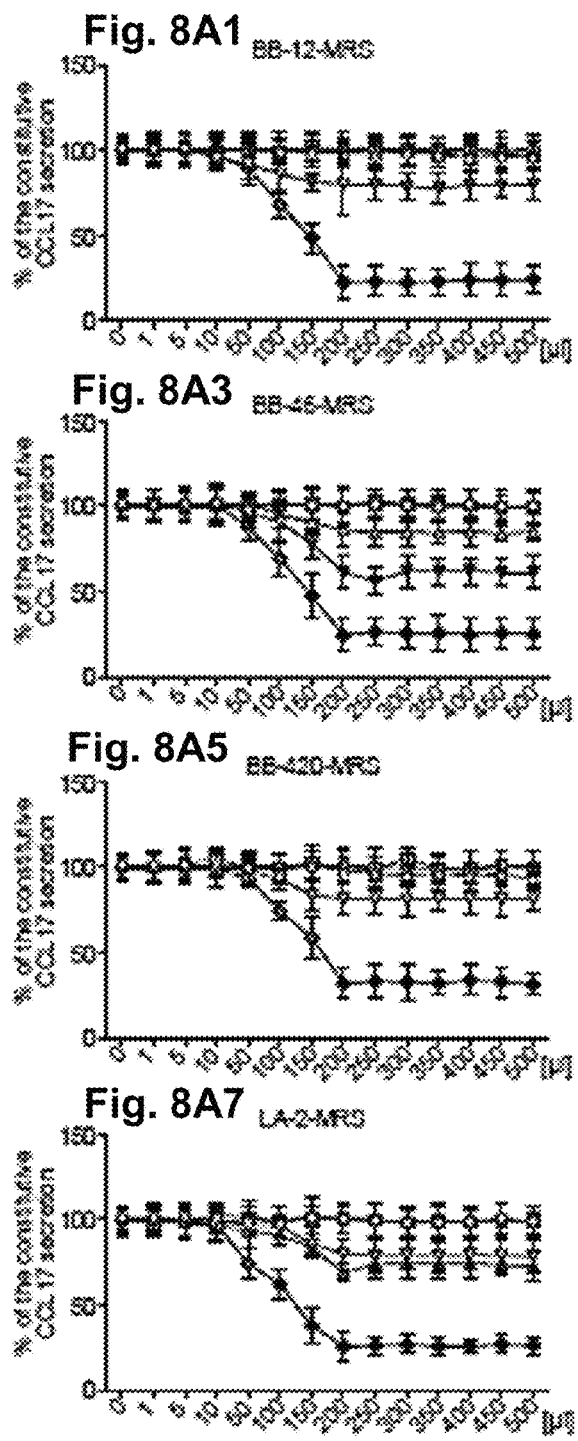
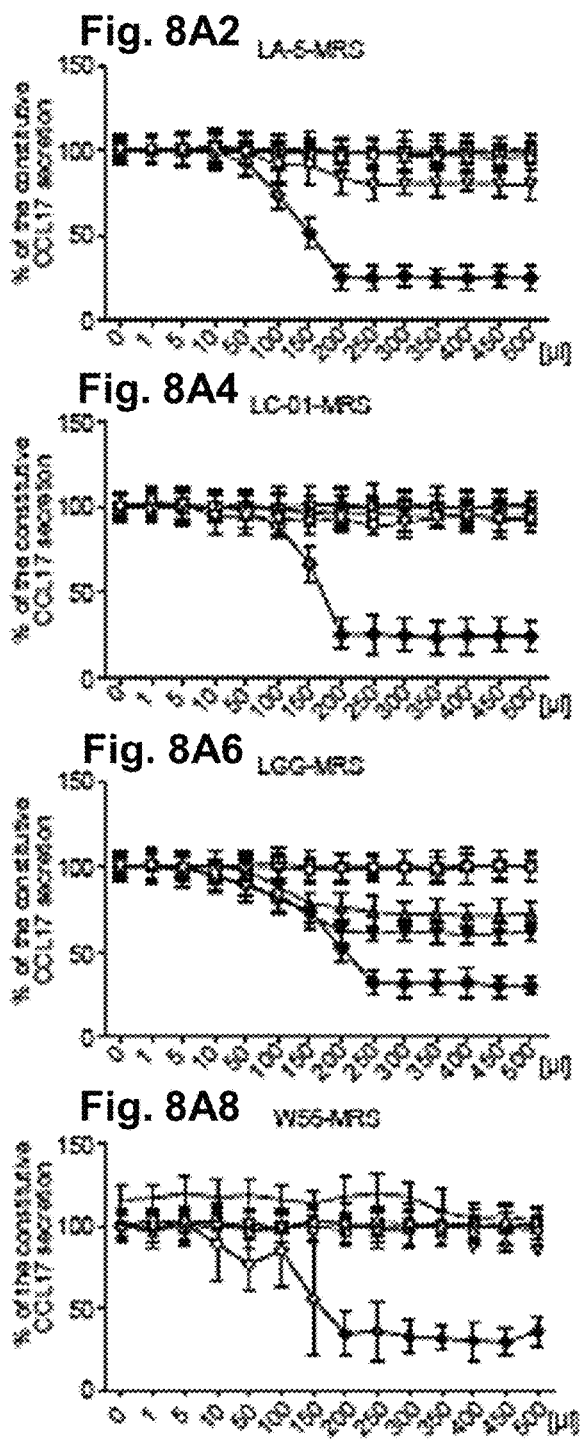

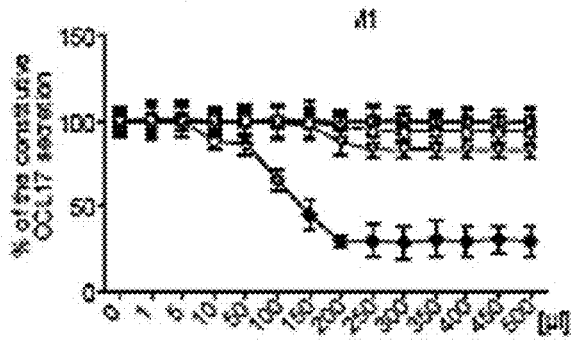
Fig. 8B1
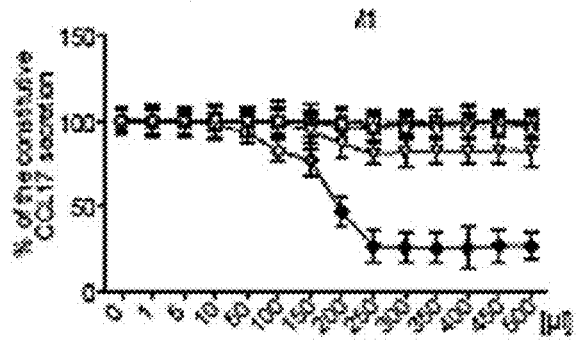
Fig. 8B2
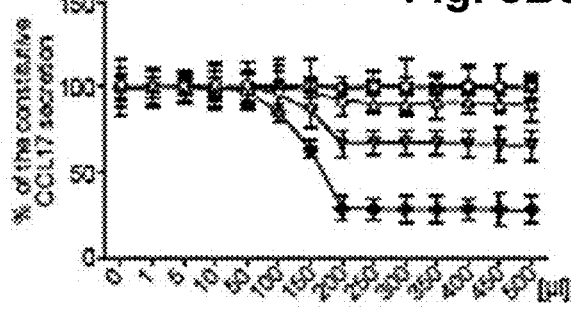
Fig. 8B3
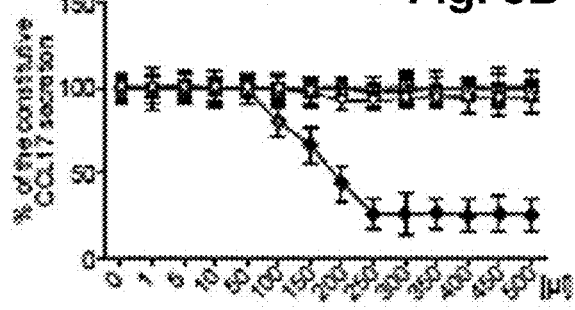
Fig. 8B4
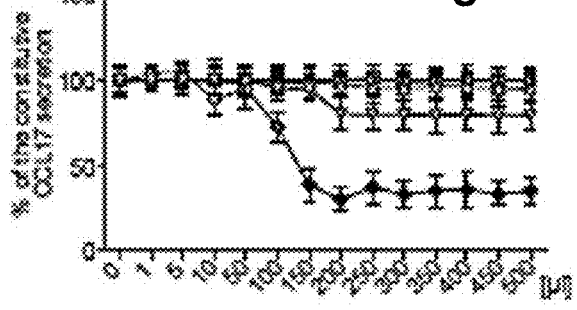
Fig. 8B5
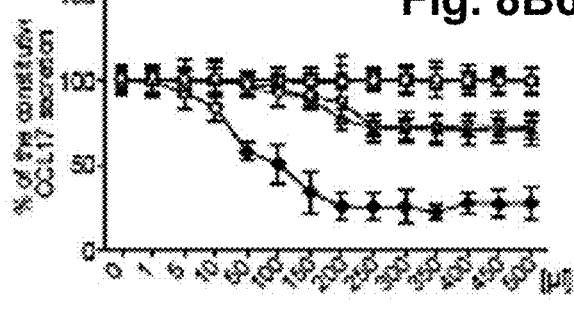
Fig. 8B6
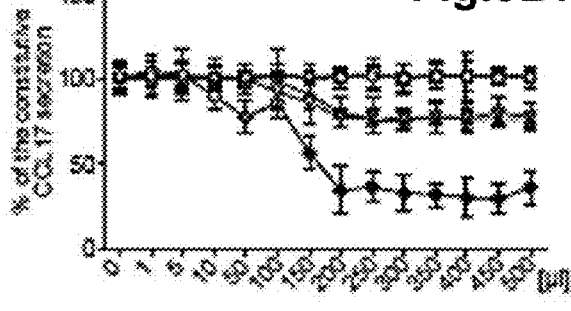
Fig. 8B7
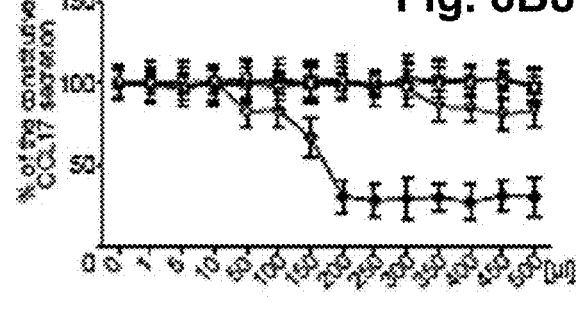
Fig. 8B8

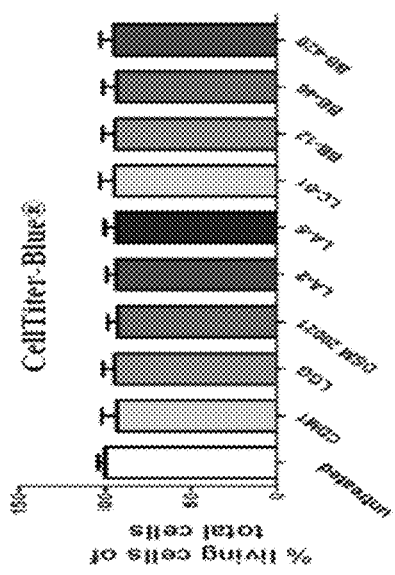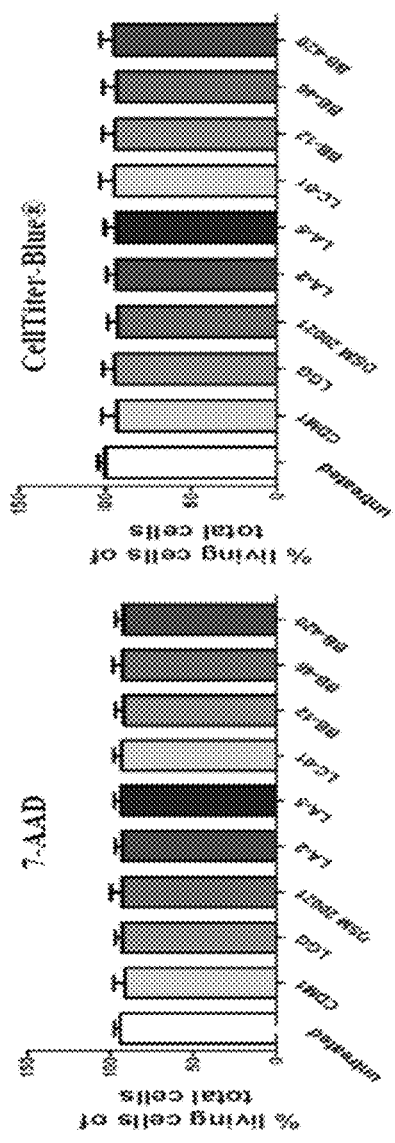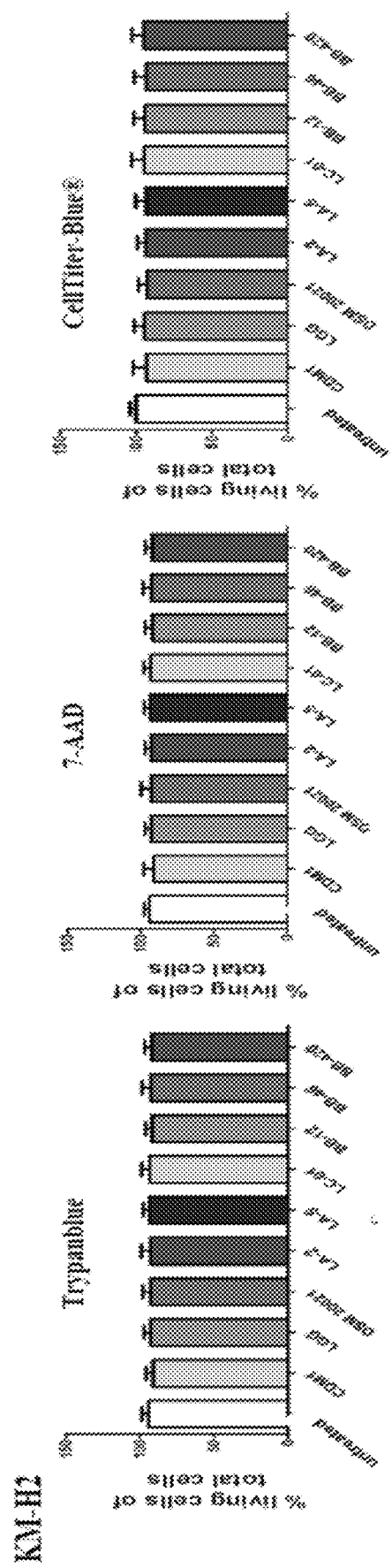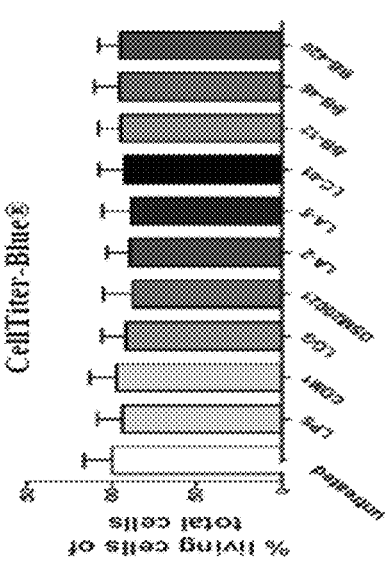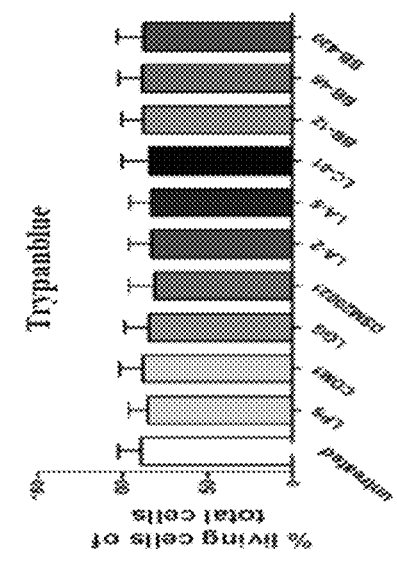

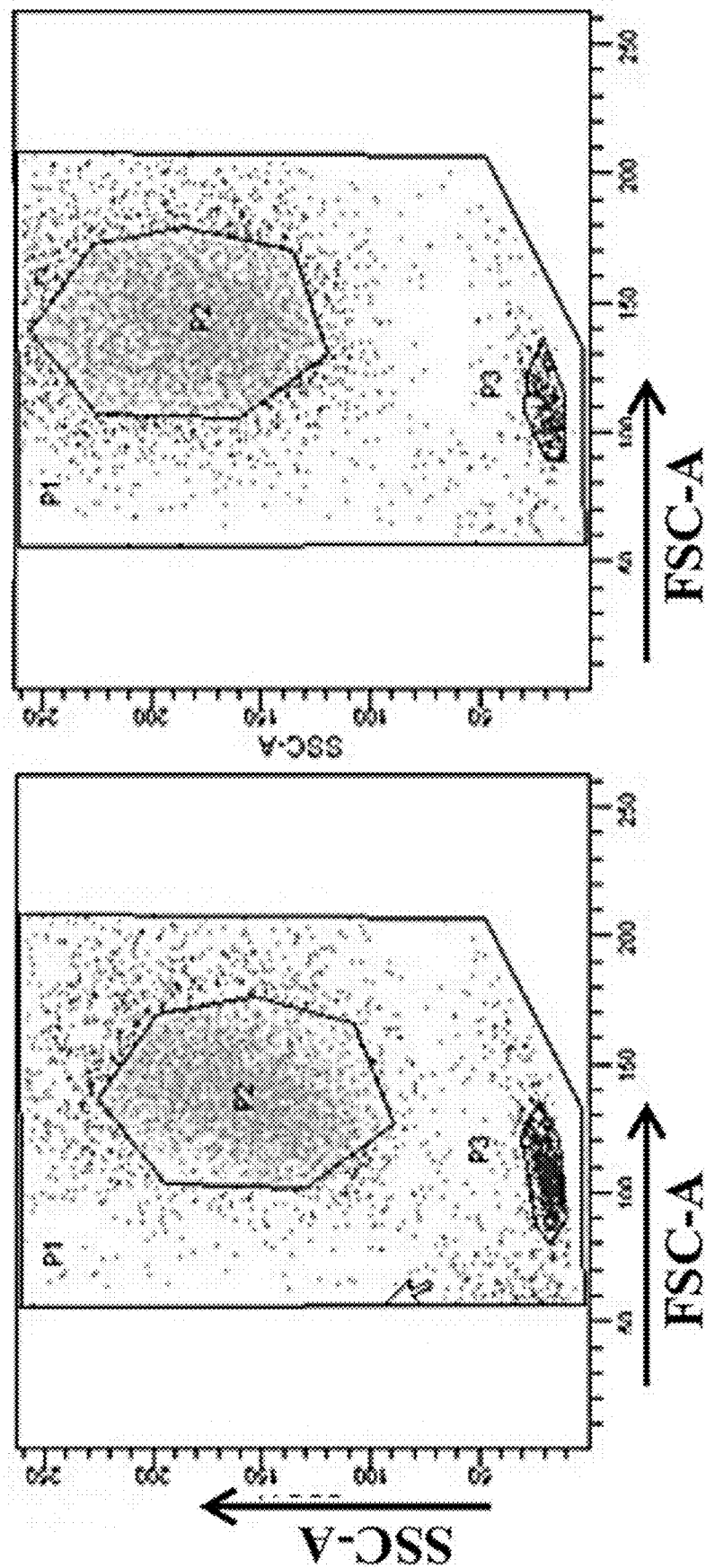
Fig. 9D1 Immature DCs
Fig. 9D2 S treated DCs

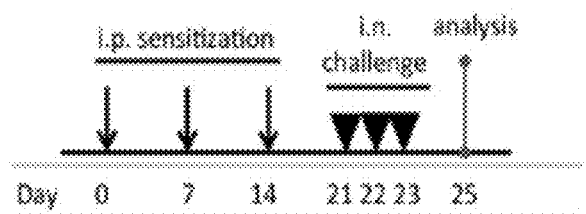
Fig. 14A
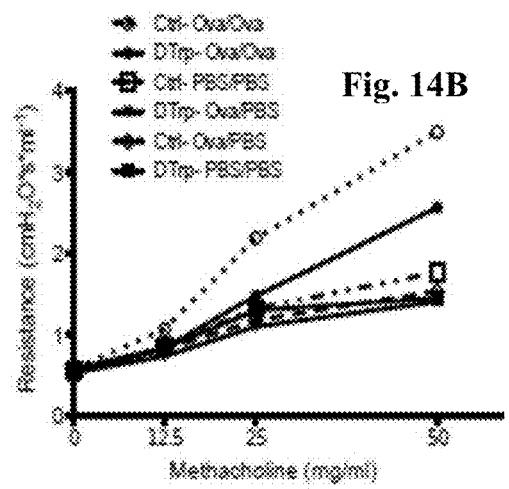
Fig. 14B
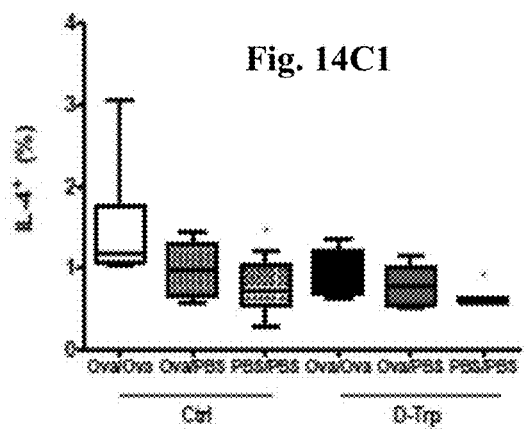
Fig. 14C1
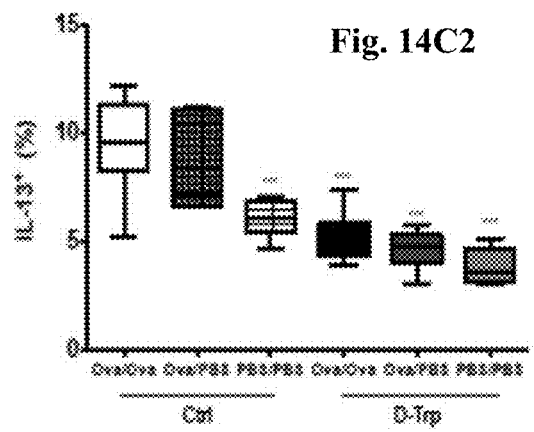
Fig. 14C2
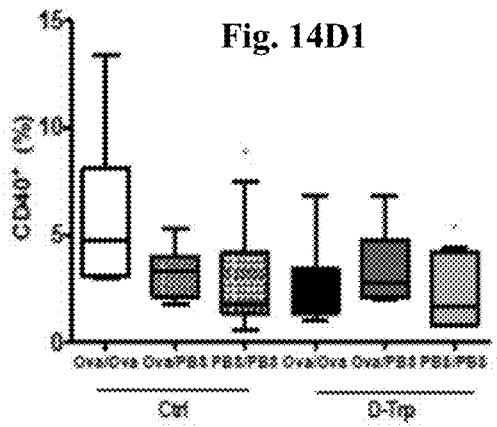
Fig. 14D1
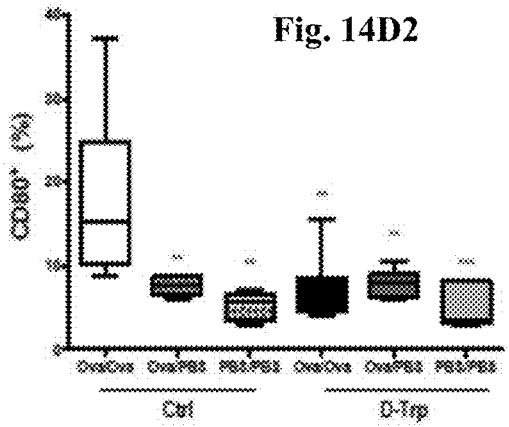
Fig. 14D2

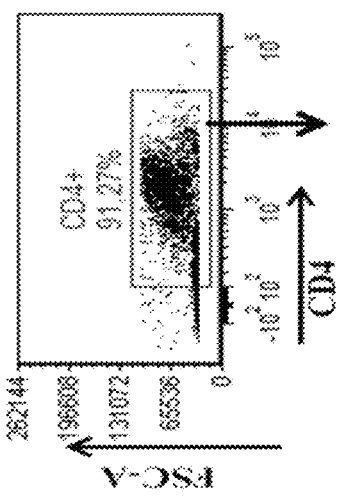
Fig. 15A3
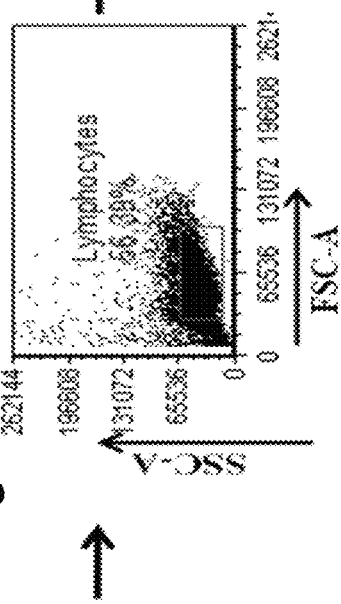
Fig. 15A2
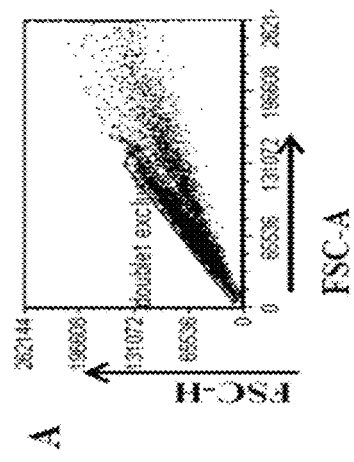
Fig. 15A1
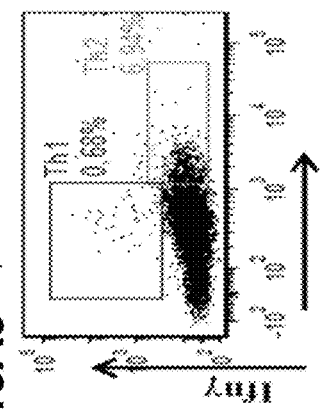
Fig. 15A6
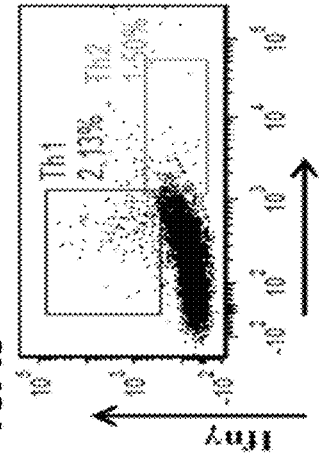
Fig. 15A5
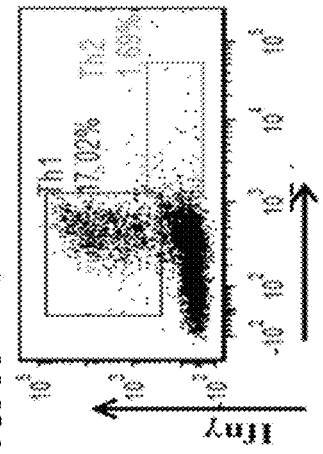
Fig. 15A4

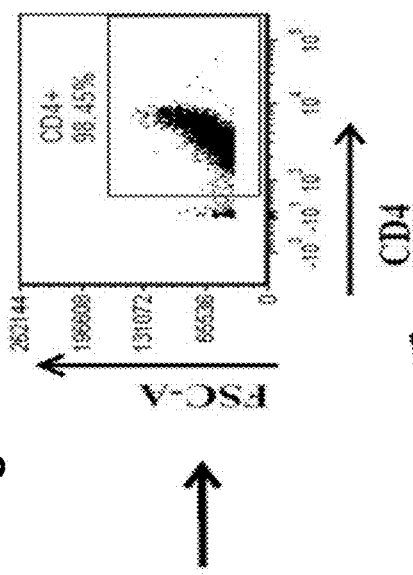
Fig. 15B3
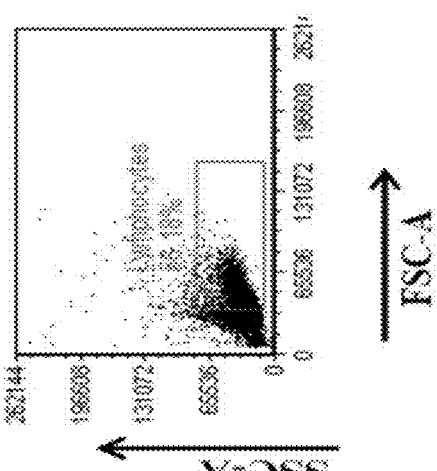
Fig. 15B2
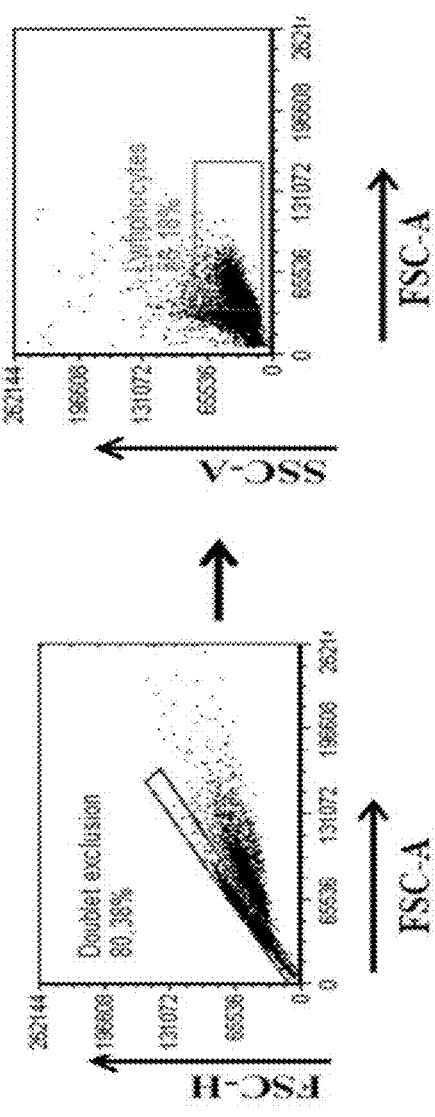
Fig. 15B1
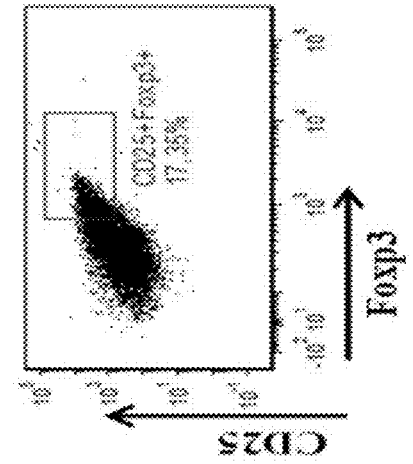
Fig. 15B5
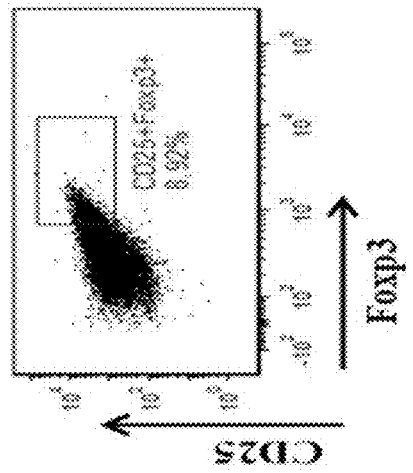
Fig. 15B4

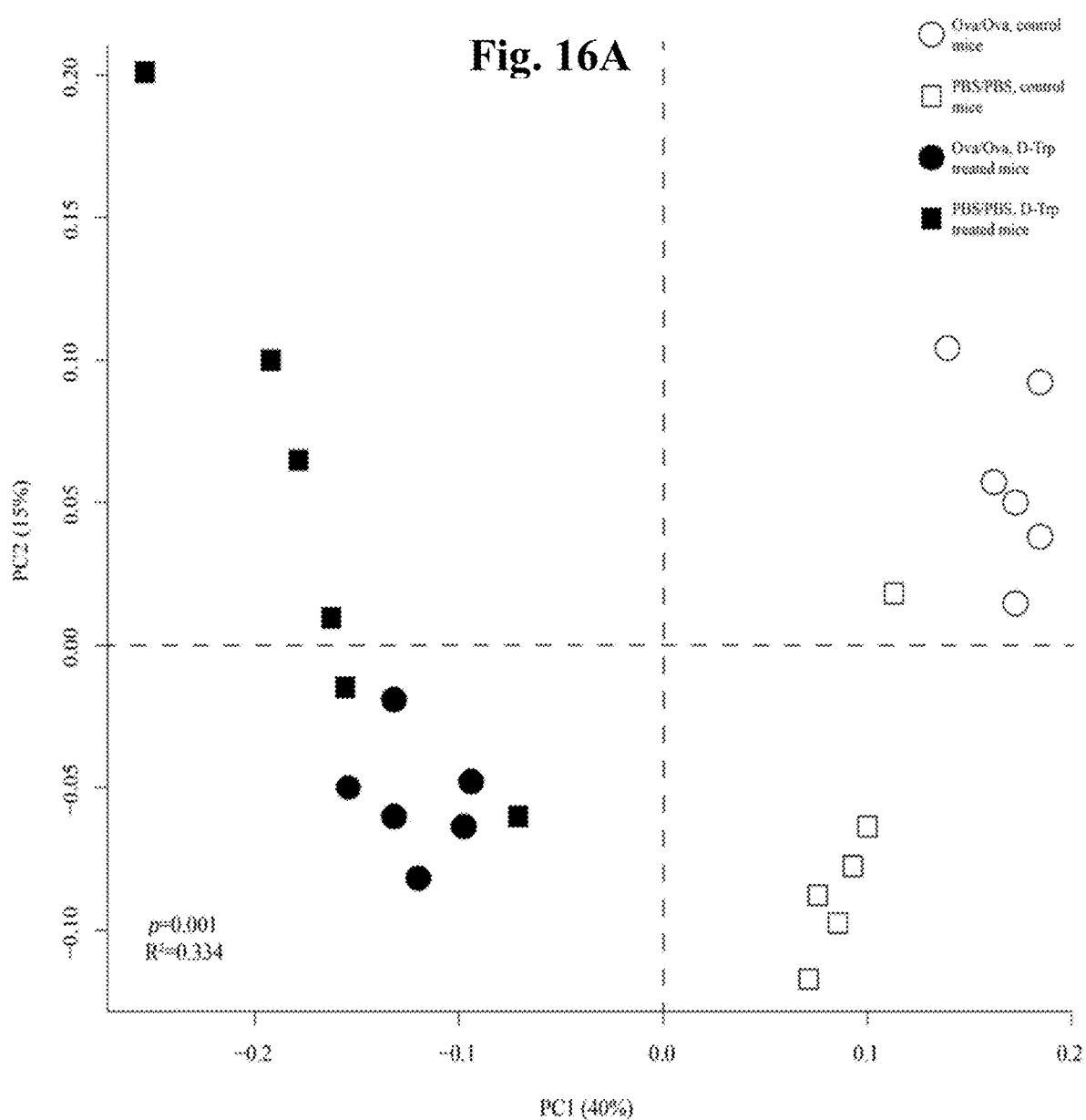

Fig. 16B1
Ova/Ova, control mice
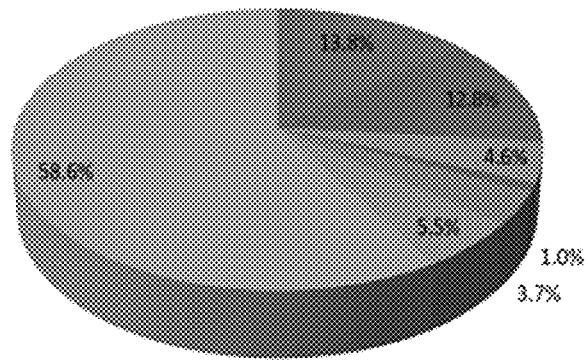
Fig. 16B2
PBS/PBS, control mice
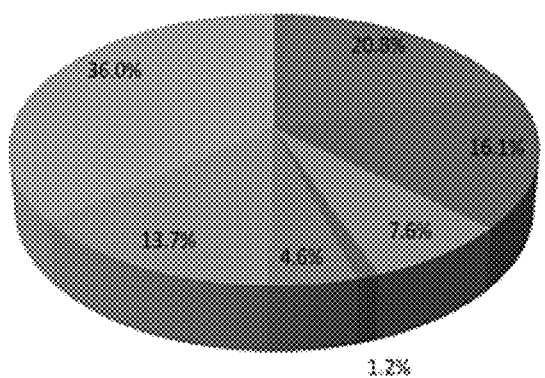
Ova/Ova, D-Trp treated mice
Fig. 16B3
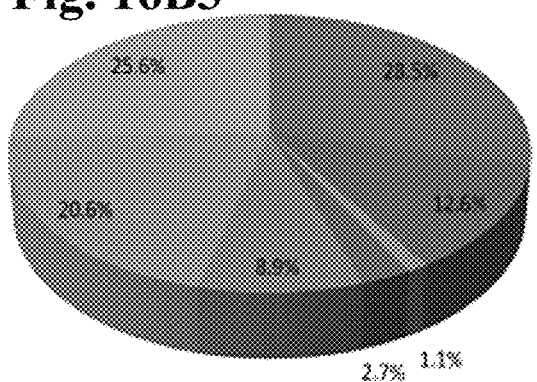
PBS/PBS, D-Trp treated mice
Fig. 16B4
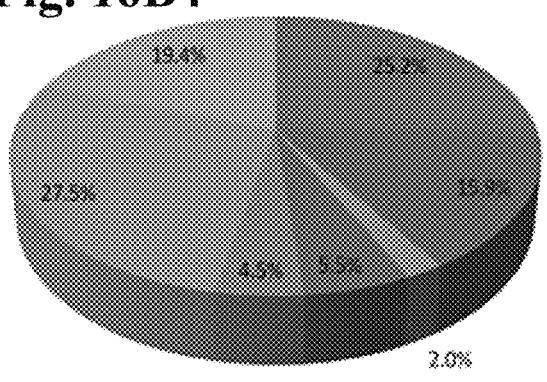
- unclass. Bacteria
- Bacteroidales;S24-7
- Bacteroidales;Rikenellaceae
- Bacteroidales;Odoribacteraceae
- Clostridiales;Ruminococcaceae
- Clostridiales;Lachnospiraceae
- unclass. Clostridiales

SEQUENCE LISTING

```
<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: primer S-D-Bact-0785-a-S-18

<400> SEQUENCE: 1
ggmttagata cccbdgta                                                 18

<210> SEQ ID NO 2
<211> LENGTH: 15
<212> TYPE: DNA
<213> ORGANISM: Artificial Sequence
<220> FEATURE:
<223> OTHER INFORMATION: primer S-*-Univ-1100-a-A-15

<400> SEQUENCE: 2
gggtykcgct cgttr                                                    15

<210> SEQ ID NO 3
<211> LENGTH: 20
<212> TYPE: DNA
<213> ORGANISM: Artificial Sequence
<220> FEATURE:
<223> OTHER INFORMATION: primer sequence Gata3 FW

<400> SEQUENCE: 3
cttatcaagc ccaagcgaag                                               20

<210> SEQ ID NO 4
<211> LENGTH: 20
<212> TYPE: DNA
```

```
<213> ORGANISM: Artificial Sequence
<220> FEATURE:
<223> OTHER INFORMATION: primer sequence Gata3 rev

<400> SEQUENCE: 4
cattagcgtt cctcctccag                                               20

<210> SEQ ID NO 5
<211> LENGTH: 21
<212> TYPE: DNA
<213> ORGANISM: Artificial Sequence
<220> FEATURE:
<223> OTHER INFORMATION: primer sequence IL4 fwd

<400> SEQUENCE: 5
ggatgcgaca aaaatcactt g                                             21

<210> SEQ ID NO 6
<211> LENGTH: 20
<212> TYPE: DNA
<213> ORGANISM: Artificial Sequence
<220> FEATURE:
<223> OTHER INFORMATION: primer sequence IL4 rev

<400> SEQUENCE: 6
ttggaagccc tacagacgag                                               20

<210> SEQ ID NO 7
<211> LENGTH: 20
<212> TYPE: DNA
<213> ORGANISM: Artificial Sequence
<220> FEATURE:
<223> OTHER INFORMATION: primer sequence Ifny fwd

<400> SEQUENCE: 7
aggtcaacaa cccacaggtc                                               20

<210> SEQ ID NO 8
<211> LENGTH: 20
<212> TYPE: DNA
<213> ORGANISM: Artificial Sequence
<220> FEATURE:
<223> OTHER INFORMATION: primer sequence Ifny rev

<400> SEQUENCE: 8
gaatcagcag cgactccttt                                               20

<210> SEQ ID NO 9
<211> LENGTH: 22
<212> TYPE: DNA
<213> ORGANISM: Artificial Sequence
<220> FEATURE:
<223> OTHER INFORMATION: primer sequence Foxp3 fwd

<400> SEQUENCE: 9
tcaagtacca caatatgcga cc                                            22

<210> SEQ ID NO 10
<211> LENGTH: 21
<212> TYPE: DNA
<213> ORGANISM: Artificial Sequence
```

```
<220> FEATURE:
<223> OTHER INFORMATION: primer sequence Foxp3 rev

<400> SEQUENCE: 10
taggcgaaca tgcgagtaaa c                                              21
```

METHODS AND COMPOSITIONS FOR TREATING INFLAMMATORY DISEASES

REFERENCE

The entire contents of the ASCII text file entitled "IPM0077US_Sequence_Listing.txt" created on Sep. 16, 2017, having a size of 3 kilobytes is incorporated herein by reference.

FIELD

The invention relates the treatment of inflammatory diseases using compositions that include D-tryptophan.

BACKGROUND

Chronic immune diseases, such as allergies, inflammatory bowel disease, or diabetes, are highly prevalent in industrialized countries, and a further increase of burden caused by noncommunicable diseases is expected for the next decades (World Health Organization; Global status report on noncommunicable diseases 2010. The incidence of the allergic disease asthma has increased continuously over the last 50 years in affluent countries (Pawankar; 2014, World Allergy Organization Journal; vol. 7; issue 1: 12). This trend has reached $2^{nd}$ world countries with rapid economic development resulting in currently 223 million asthma patients worldwide (Global Asthma Network; The Global Asthma Report 2014; Auckland, New Zealand; 2014). A further increase of asthma prevalence is expected within the next years (To et al., BMC Public Health; vol. 12; issue 1: 254; Global Data. Asthma—Epidemiology Forecast to 2013; 2014).

Asthma is a complex and heterogeneous chronic inflammation of the upper airways caused by a hypersensitivity of the bronchial system against different environmental stimuli. The disease leads to structural and functional changes in the lungs, including goblet cell hyperplasia, airway smooth muscle hypertrophy and subepithelial fibrosis in the airways that in turn give rise to airway hyperresponsiveness (AHR) and reversible airflow limitation (Barnes, 2014, Immunological Reviews, vol. 242, issue 1: 31-50). The processes that underlie asthma are characterized by different patterns of cytokine-based inflammation involving diverse cell types such as T cells, B cells, mast cells, eosinophils, basophils, neutrophils and dendritic cells, as well as structural cell types including epithelial, smooth muscle and mesenchymal cells (Walsh, 2013, Immunotherapy, vol. 5, issue 11: 1255-1264).

Accumulating knowledge has driven the development of biological therapies that target the cytokines important in asthma pathobiology, such as IL-4, IL-5 and IL-13. However, with the exception of the anti-IgE monoclonal antibody omalizumab, early clinical trials with cytokine-targeted biologics in patients with asthma were disappointing (Walsh et al., 2013). Therefore, current therapies for the treatment of asthma mainly include two types of medication. Long-term control medicines, such as corticosteroids, generally reduce inflammation of the airways and are the most effective option for long-term relief. In order to achieve this preventing effect, the medicaments have to be administered repeatedly for the entire lifetime and cause well-documented side effects. Quick-relief medicines, such as short-acting beta2-agonists, are administered if required to treat acute symptoms. These medicines act quickly to relax tight muscles around the airways upon a flare-up allowing the airways to open up.

However, all available therapies only achieve a symptomatic relief but are unable to cure the disease or reduce its prevalence. In consequence, patients suffer from asthma for their entire life time constituting a huge burden for the health care systems with overall costs for asthma in Europe of € 19.3 billion in 2010 (Accordini et al., 2013, International archives of allergy and immunology, vol. 160, issue 1: 93-101). Furthermore, patients under treatment with corticosteroids frequently suffer from strong side effects. Thus, there is a high and so far unmet need to develop novel strategies for asthma treatment and prevention.

Asthma is the result of a reduced diversity of the human microbiome, which modulates the immune system and induces the symptoms. Thus, increasing the diversity of the human microbiome could result in a modulation of the immune response and thus amelioration or cure of asthma. However, a sustainable modification of the human microbiome, in particular increasing the diversity, remains challenging. Although probiotic bacteria have been shown to modify immune responses in vitro (Borthakur et al., 2010, Am J Physiol Gastrointest Liver Physiol, vol. 299, pages G928-G934; Heuvelin et al., 2010, J Nutr, vol. 140, pages 7-11; Mileti et al., 2009, PLoS One, vol. 4, page e7056) and in animal studies (Kwon et al., 2010, PNAS, vol. 107, pages 2159-2164; Fanning et al., 2012, PNAS, vol. 109, pages 2108-2113), clear evidence for clinical efficacy in the treatment of chronic inflammatory disorders is largely lacking. Apart from acute infectious diarrhea (Allen et al., 2010, Cochrane database Syst Rev (11), p. CD003048) clinical trials for different indications, such as primary prevention of allergic diseases (Boyle et al., 2011, Allergy, vol. 66, pages 509-516 and others) or treatment of chronic inflammatory bowel disease (Butterworth et al., 2008, Cochrane database Syst Rev (3), p. CD006634), were highly inconsistent. Accordingly, Fiocchi et al. (2012, World Allergy Organ Journal, vol. 5, pages 148-167) and the European Food Safety Authority stated that a role for probiotic microbes for prevention of allergic manifestations is not established. One important reason for the conflicting results is most likely the extremely complex crosstalk among probiotic bacteria, the host's microbiota and immune cells. Even in healthy subjects, the gut microbiome differs remarkably among individual subjects. In addition, both the microbiome and immunity can be substantially altered under disease conditions. Thus, it is hard to predict the precise functionality of a probiotic strain in individual subjects. In addition, there is a lack of mechanistic understanding that is important to establish biological plausibility for any claimed health effect (Kepert et al., 2017, Journal of Allergy and Clincal Immunology, vol. 139, issue 5: 1525-1535).

In contrast to higher organisms, numerous bacteria, including probiotic bacteria, produce D-amino acids, such as D-glutamate and D-alanine, by using them mainly for crosslinking glycan chains in the peptidoglycan wall (Cava et al., 2011, EMBO, vol. 20, pages 3442-3453). A role for D-tryptophan in bacterial communication was discovered by demonstrating its requirement for disassembly of biofilms in *Bacillus subtilis* (Kolodkin-Gal et al, 2010, Science, vol. 328, pages 627-629).

D-amino acids are nonproteinogenic enantiomers of L-amino acids. Until the discovery of free D-aspartate and D-serine in the mammalian brain as neurotransmitters in the late 1980s, D-amino acids were considered to play no role in higher organisms. So far, research on D-amino acids in mammals has been mainly restricted to the nervous system because of the relative abundance of D-aspartate and D-serine in the brain (Hashimoto et al., 1993, J Neurochem., vol. 61, pages 348-351) and the difficulty of detecting D-amino acids at trace levels (Visser et al., 2011, J Chromatogr A, vol. 1218, pages 7130-7136). Thus very little is known on D-tryptophan in humans, and it has been assumed that higher organisms use D-tryptophan poorly (Triebwasser et al, 1976, J Nutr, vol. 106, pages 642-652).

In sum, the treatment of inflammatory diseases, in particular allergic airway diseases, such as asthma, remains challenging. Consequently, there is a high and so far unmet need for novel treatments and preventions of such inflammatory diseases. This problem is addressed by the present invention.

Now, the present inventors surprisingly discovered for the first time that D-tryptophan acts as an immunomodulatory substance influencing both, immune responses and the gut microbial diversity. The present inventors further surprisingly discovered that D-tryptophan conceivably reduces the degree of allergic airway disease (AAI) in mice and maintains a diverse gut microbiota, which was otherwise lost in animals with AAI. Since mice models of allergic airway disease represent acknowledged model systems which allow extrapolation of obtained results and effects to human (Chapman et al., 2014, J. Cell Biochem 115(12); 2055-2064), the results obtained by the present inventors can be reasonably transferred and/or extrapolated to humans. Therefore, the present invention provides for the first time prevention and treatment of allergic diseases such as asthma.

SUMMARY

The current invention is directed to compositions and methods for treating or preventing inflammatory diseases based on various experimental studies, including those showing D-tryptophan compositions were able to lower cytokine secretion and prevent upregulation of inflammatory molecules in cellular studies, and also alter immune responses in animal models.

In one aspect, the invention provides a food or pharmaceutical composition that comprises D-tryptophan. The food or pharmaceutical composition can include one or more excipient materials that are edible and suitable for oral ingestion, or one or more excipient materials suitable for administration of the pharmaceutical composition via a desired route. A D-tryptophan pharmaceutical composition can be formulated for oral, intravenous, subcutaneous, parenteral, transdermal, intraperitoneal, intramuscular or pulmonary administration.

The D-tryptophan can be present in an amount and configured in the food or pharmaceutical composition to elicit one or more of the following effect(s): (1) decreases constitutive CCL17 secretion of the cell line KM-H2 and/or preventing upregulation of costimulatory molecules of LPS-stimulated human dendritic cells; (2) increases the serum level of D-tryptophan in a subject; (3) alters the gut microbiota in a subject upon administration; and/or (4) treats, prevents, or ameliorates a disease associated with $T_{reg}$ or $T_H2$ cells in a subject.

In another aspect, the invention provides a method for the treatment, prevention or amelioration of a disease associated with $T_{reg}$ or $T_H2$ cells in a subject suffering from, or at risk for such a disease. The method comprises a step of ingesting or administering to said subject a composition comprising D-tryptophan. Following said ingesting or administering, the disease associated with $T_{reg}$ or $T_H2$ cells in the subject is treated, prevented, or ameliorated. In aspects the disease is allergy, an allergic airway disease, or asthma.

BRIEF DESCRIPTION OF THE DRAWINGS

FIGS. 1B1-1B5 are graphs showing the effect of various bacterial supernatants to prevent full upregulation of costimulatory molecules and HLA-DR on LPS stimulated human monocyte derived dendritic cells.

FIGS. 2A-2D are graphs showing the effect of various bacterial supernatants to lower CCL17 secretion of KM-H2 cells.

FIG. 4 is a graph showing the effect of tryptophan L- and D-isomers on CCL17 secretion by KM-H2 cells.

FIGS. 5A1 and 5A2 are graphs of serum D-tryptophan in mice receiving D-tryptophan (50 mM) in drinking water or water only; FIG. 5B is a graph of the total number of cells in BALF; FIG. 5C is a graph of the differential cell count; FIG. 5D is a graph of airway resistance to increasing doses of methacholine(two-way ANOVA with Bonferroni post-test); FIGS. 5E1 and 5E2 are graphs of Ifn-g and Il-4 in lung-derived CD3$^+$CD4$^+$ lymphocytes; FIG. 5F is a graph of Il-4 levels in BALF of mice, assessed by CBA; and FIG. 5G is a graph of Helios+ Tregs of lung-derived CD3$^+$CD4$^+$ Foxp3$^+$ lymphocytes.

FIGS. 6A1-6C2 are graphs representing differentiation of primary, murine splenocytes differentiated towards Th1 (FIGS. 6A1 and 6A2), Th2 (FIGS. 6B1-6B6), and Treg (FIGS. 6C1 and 6C2) with respective cytokine mixes under the presence of 0, 10 or 50 µM D-Trp (dissolved in water). Differentiation was assessed by flow cytometry, qRT-PCR and CBA for Il-13 and Il-5 protein levels from culture supernatants.

FIGS. 8A1-8A8 are graphs showing the capacity of supernatants from bacteria cultured in rich MRS medium to lower CCL17 secretion of KM-H2 cells. FIGS. 8B1-8B8 are graphs showing the capacity of supernatants from bacteria cultured in restricted CDM1 medium to lower CCL17 secretion of KM-H2 cells.

FIGS. 9A1-9C2 are graphs of viability analysis of KM-H2cells (FIGS. 9A1-9C1) and primary DCs (FIGS. 9A2-9C2) after treatment with probiotic supernatants with trypanblue (FIGS. 9A1, 9A2), 7-AAD staining (FIGS. 9B1, 9B2) and photometric analysis after treatment with CellTiter-Blue® reagent (FIGS. 9C1, 9C2). FIGS. 9D1 and 9D2 are graphs of purity assessment of primary DCs via flow cytometry before (FIG. 9D1) and after LPS stimulation (FIGS. 9D2) (representative image).

FIGS. 12A(1) and 12B(1) are an enlargement of the shaded areas of FIGS. 12A(1) and 12B(1), respectively.

FIG. 14A is an time line illustration of a treatment scheme for induction of allergic airway inflammation using oral D-tryptophan. FIG. 14B is a graph of airway resistance to increasing doses of methacholine. FIG. 14C1 and 14C2 are graphs of percent II-4$^+$ and II-13$^+$ cells, respectively, within spleen CD3$^+$CD4$^+$ T cells. FIG. 14D1 and 14D2 are graphs of CD40$^+$ and CD80$^+$, respectively, on spleen CD11b$^{high}$DCs.

FIGS. 15A1-15B5 is a gating strategy and graphs of analysis of Th1 & Th2 cells as assessed by CD4$^+$Ifny$^+$ or CD4$^+$II4$^+$ (FIGS. 15A1-15A6), and induced Tregs as CD4$^+$CD25$^+$Foxp3$^+$ cells (FIGS. 15B1-15B5).

FIG. 16A is a scatterplot of Principal Coordinate Analysis (PCoA) based on D-tryptophan supplementation on the intestinal bacterial composition in healthy and diseased mice. FIGS. 16B1-16B4 are pie charts were representing the relative distribution of the most abundant bacteria at the family level.

DETAILED DESCRIPTION

Figure 1A:
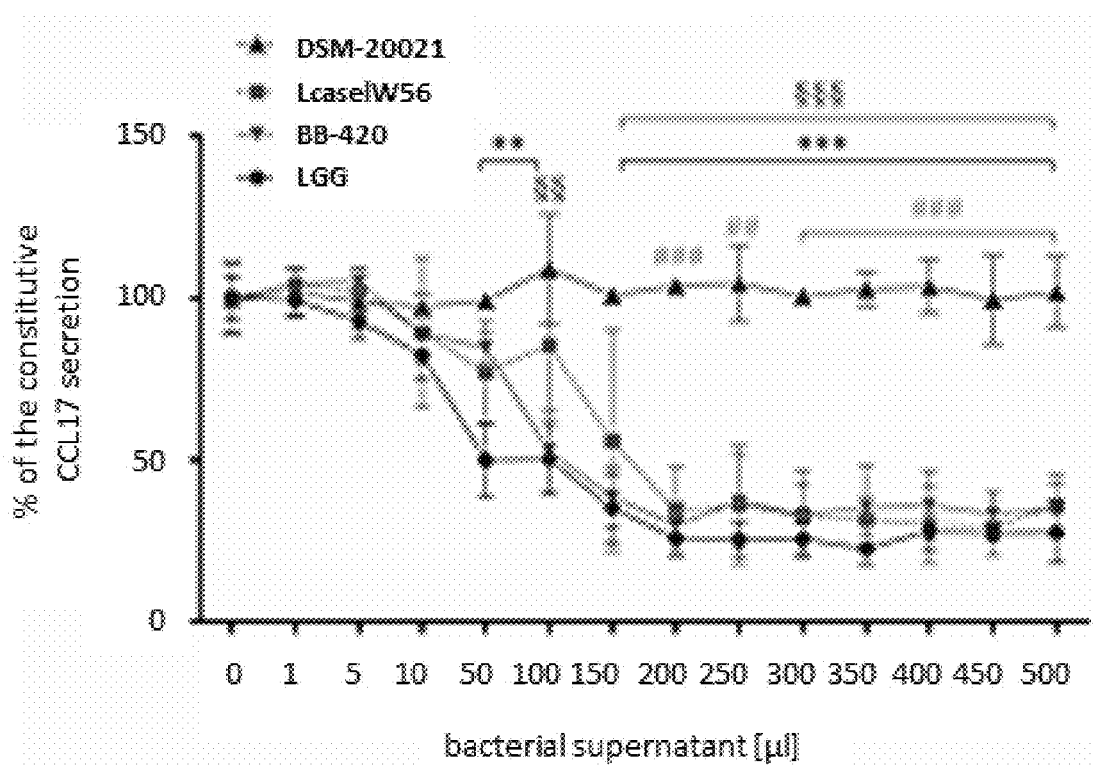
FIG. 1A is a graph of showing the effect of various bacterial supernatants to lower CCL17 secretion of human Hodgkin lymphoma KM-H2 cells.

The present inventors screened supernatants of probiotic bacteria for their ability to concordantly lower the constitutive CCL17 secretion of a human Hodgkin lymphoma cell line and prevent upregulation of costimulatory molecules of LPS-stimulated human dendritic cells. The present inventors found that supernatants from 13 of 37 tested probiotic strains showed immunoactivity. Bioassay-guided chromatographic fractionation of two supernatants according to polarity, followed by total ion chromatograms and mass spectrometry, yielded $C_{11}H_{12}N_2O_2$ as molecular formula of a bioactive substance. Proton nuclear magnetic resonance and enantiomeric separation identified D-tryptophan. In contrast, L-tryptophan and eleven other D-amino acids were inactive. Furthermore, feeding D-tryptophan to mice prior to experimental asthma induction, increased numbers of lung and gut regulatory T cells, lowered lung $T_H2$ responses, and ameliorated allergic airway inflammation and hyperresponsiveness. Allergic airway inflammation reduced the gut microbial diversity, which was increased by D-tryptophan. In sum, D-tryptophan is a newly identified product from probiotic bacteria. The findings of the present inventors show that D-tryptophan can be used in novel preventative and/or therapeutic strategies for inflammatory diseases, such as allergies, for example, an allergic airway disease, for example asthma.

Therefore, the present invention provides a food composition comprising D-tryptophan.

The term "food composition" as used herein generally relates to a composition comprising D-tryptophan and an orally acceptable carrier or excipient. A food composition according to the present invention comprises any eatable, palatable and/or drinkable stuff for mammals, for example, humans or animals, e.g. pets. Such a food composition can be produced by a general method for producing foods, drinks or feeds, including adding D-tryptophan to a raw or cooked material of food, drink or feed. By addition D-tryptophan the composition may in embodiments be referred to as a "prepared food composition", "prepared food product" or "prepared beverage," which reflects the composition is a man-made (fabricated) composition. In turn, such a man-made food or beverage composition may have a D-tryptophan concentration higher than any naturally-occurring material (e.g., probiotic bacteria) by weight. The food composition in accordance with the present invention can be molded and granulated in the same manner as generally used for foods, drinks or feeds. The molding and granulating method includes granulation methods such as fluid layer granulation, agitation granulation, extrusion granulation, rolling granulation, gas stream granulation, compaction molding granulation, cracking granulation, spray granulation, and injection granulation, coating methods such as pan coating, fluid layer coating, and dry coating, puff dry, excess steam method, foam mat method, expansion methods such as microwave incubation method, and extrusion methods with extrusion granulation machines and extruders. Specific food compositions to which D-tryptophan is added, include, for example, juices, refreshing drinks, drinking water, soups, teas, milk, beverages, dairy products such as fermented milks, ices, butter, cheese, processed milk and skim milk, meat products such as ham, sausage, and hamburger, fish meat cake products, egg products such as seasoned egg rolls and egg curd, confectioneries such as cookie, jelly, snacks, and chewing gum, breads, noodles, pickles, smoked products, dried fishes and seasonings. The form of the food or drink includes, for example, powder foods, sheet-like foods, bottled foods, canned foods, retort foods, capsule foods, tablet foods and fluid foods. Food compositions to be ingested by infants, are preferably nutritious compositions for infants. Such nutritious composition for infants includes modified milk prepared for infants, protein-decomposed milk, specific nutritionally modified milk or baby foods and foods prepared for toddlers. The form of the nutritious composition for infants includes but is not specifically limited to powder milks dried and pulverized and baby foods and also include general foods such as ice cream, fermented milk, and jelly for infantile ingestion. The food composition of the present invention comprising D-tryptophan can also be used as feed for pets. The pet feed includes, for example, pet feeds for dogs, cats and rats, cattle feeds for cows and pigs, chicken feeds for chicken and turkeys, and fish cultivation feeds for porgy and yellowtail. The feed can be produced by appropriately blending D-tryptophan in a raw feed material including, for example, cereals, brans, oil-seed meals, animal-derived raw feed materials, other raw feed materials and purified products. The cereals include, for example, mile, wheat, barley, oats, rye, brown rice, buckwheat, fox-tail millet, Chinese millet, Deccan grass, com, and soybean. The brans include, for example, rice bran, defatted rice bran, bran, lowest-grade flour, wheat germ, barley bran, screening pellet, corn bran, and corn germ. The oil-seed meals include, for example, soybean meal, soybean powder, linseed meal, cottonseed meal, peanut meal, safflower meal, coconut meal, palm meal, sesame meal, sunflower meal, rapeseed meal, kapok seed meal and mustard meal. The animal-derived raw feed materials include, for example, fish powders, import meal, whole meal, and coast meal, fish soluble, meat powder, meat and bone powder, blood powder, decomposed hair, bone powder, byproducts from butchery, feather meal, silkworm pupa, skim milk, casein, dry whey and krill. Other raw feed materials include, for example, plant stems and leaves such as alfalfa, hey cube, alfalfa leaf meal, and locust leaf powder, byproducts from corn processing industries, such as corn gluten meal, corn gluten feed and corn steep liquor, starch, sugar, yeast, byproducts from fermentation industry such as beer residue, malt root, liquor residue and soy sauce residue, and agricultural byproducts such as citrus processed residue, soybean curd residue, coffee residue, and cocoa residue, cassava, horse bean, guar meal, seaweed, spirulina and chlorella. The purified products include, for example, proteins such as casein and albumin, amino acids, starch, cellulose, saccharides such as sucrose and glucose, minerals and vitamins.

For preparation of a food composition, the D-tryptophan can be added to a raw or cooked material of food, drink, or feed in an amount effective to provide a desired biologic effect when the food material is consumed by a subject. A desired biologic effect can include, for example, achieving a serum concentration of D-tryptophan after a recommended portion (e.g., recommended serving size) of a solid food product or a beverage is consumed by the subject. The solid food product or beverage can include packaging or labeling indicating the amount of D-tryptophan added per amount of other food materials, or an amount in the liquid beverage, and a recommendation of how much to consume on the package or container. A desired serum concentration can be understood by known techniques, including by ULCMS to determine peak areas of D-tryptophan. The term "D-tryptophan" as used herein relates to the non-proteinogenic enantiomer of the amino acid L-tryptophan. D-tryptophan is characterized by the following formula.

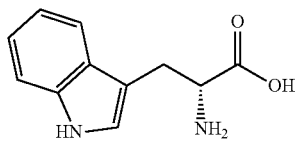

In a preferred embodiment of the present invention, the food composition comprises one or more ingredients selected from the group consisting of an orally acceptable carrier, sweeteners, colorants, preservatives, thickeners and stabilizers, anti-oxidants, color fixing agents, bleaches, antiseptics, gum base, bitters, enzymes, brightening agents, acidifier, seasonings, emulsifiers, enhancers, agents for manufacture, flavors, spice extracts, saccharides, starch, inorganic materials, plant powders, excipients, disintegrators, lubricants, binders, surfactants, and plasticizers.

The terms "orally acceptable carrier" and "excipient" are used interchangeably herein. An orally acceptable carrier as used in context of the present invention is not toxic and of food and/or feed grade and does not interfere with the effectiveness of the biological activity of D-tryptophan. Orally acceptable carriers include, but are not limited to diluents (fillers, bulking agents, e.g. lactose, microcrystalline cellulose), disintegrants (e.g. sodium starch glycolate, croscarmellose sodium), binders (e.g. PVP, HPMC), lubricants (e.g. magnesium stearate), glidants (e.g. colloidal SiO2), solvents/co-solvents (e.g. aqueous vehicle, Propylene glycol, glycerol), buffering agents (e.g. citrate, gluconates, lactates), preservatives (e.g. Na benzoate, parabens (Me, Pr and Bu), BKC), anti-oxidants (e.g. BHT, BHA, Ascorbic acid), wetting agents (e.g. polysorbates, sorbitan esters), anti-foaming agents (e.g. Simethicone), thickening agents (e.g. methylcellulose or hydroxyethylcellulose), sweetening agents (e.g. sorbitol, saccharin, aspartame, acesulfame), flavouring agents (e.g. peppermint, lemon oils, butterscotch, etc), humectants (e.g. propylene, glycol, glycerol, sorbitol). Further orally acceptable carriers are (biodegradable) liposomes; microspheres made of the biodegradable polymer poly(D,L)-lactic-coglycolic acid (PLGA), albumin microspheres; synthetic polymers (soluble); nanofibers. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopolyplexes, inverse lipid micelles, dendrimers, ethosomes, multicomposite ultrathin capsules, aquasomes, pharmacosomes, colloidosomes, niosomes, discomes, proniosomes, microspheres, microemulsions and polymeric micelles. The person skilled in the art will readily be able to choose suitable orally acceptable carriers, depending, e.g., on the formulation of the food composition.

In a further preferred embodiment of the present invention, the food composition is capable of decreasing constitutive CCL17 secretion of the cell line KM-H2 and/or preventing upregulation of costimulatory molecules of LPS-stimulated human dendritic cells.

A person skilled in the art can easily determine whether a food composition comprising D-tryptophan is capable of decreasing constitutive CCL17 secretion of the cell line KM-H2 and/or preventing upregulation of costimulatory molecules of LPS-stimulated human dendritic cells without further ado. Suitable assays that can be used for assessing CCL17 secretion of the cell line KM-H2 or upregulation of costimulatory molecules of LPS-stimulated human dendritic cells are described elsewhere herein in detail. The KM-H2 cell line is, e.g. available from the DSMZ under accession number ACC-8. It is also described in Kamesaki et al., 1986, Blood 68(1), 285-292 or Drexler, 1993, Leukemia & Lymphoma 9(1-2), 1-25.

In another preferred embodiment of the present invention, the food composition comprises D-tryptophan in an amount sufficient to increase the serum level of D-tryptophan in a subject.

In view of the present disclosure, a person skilled in the art can readily determine the serum level of D-tryptophan in a subject. Suitable assays that can be used to determine the serum level of D-tryptophan in the serum of a subject are described elsewhere herein in detail. Preferably, the serum level of D-tryptophan is assessed by measuring ultraperformance liquid chromatography mass spectrometry peak areas of D-tryptophan as described herein in more detail. Preferably, D-tryptophan is comprised in the food composition or the pharmaceutical composition or is administered to a subject in an amount sufficient to increase the serum level of D-tryptophan in the subject, such that D-tryptophan peak area is increased at least 1.1-fold, at least 1.2-fold, at least 1.3-fold, at least 1.4-fold, at least 1.5-fold, at least 2-fold, at least 2.5-fold, at least 3-fold, at least 3.5-fold, at least 4-fold, at least 5-fold, at least 6-fold, at least 7-fold, at least 8-fold, at least 9-fold, at least 10-fold, at least 15-fold, at least 20-fold, at least 25-fold, at least 30-fold, at least 50-fold, at least 100-fold or more and preferably at least 1.5-fold and even more preferably at least 2-fold compared to the D-tryptophan peak area measured in the serum of a subject which has not been supplemented with D-tryptophan.

The term "subject" as used herein relates to an animal, preferably a mammal, e.g. a dog, cat, horse, pig, cattle, cow or goat and more preferably a human.

D-tryptophan in the food composition is not specifically limited to any concentration as long as the resulting food composition can exert its activity of increasing the serum level of D-tryptophan in a subject. The concentration of D-tryptophan is preferably 0.001 to 100% by weight, more preferably 0.01 to 100% by weight and most preferably 0.1 to 100% by weight of the food composition comprising D-tryptophan. By way of example, amounts of D-tryptophan to be ingested by a subject can be in the range of 0.01 mg/d to 100 g/d or preferably 0.1 mg/d to 100 g/d. In case of mice, the present inventors could show that oral supplementation with 0.9 mg/d D-tryptophan increased D-tryptophan serum levels significantly. Therefore, a skilled person can easily calculate a possible amount for any subject, by adjusting this amount to the weight of the subject. The exact dose will depend on the purpose of the food composition, and will be ascertainable by one skilled in the art using known techniques. As is known in the art, adjustments for age, body weight, sex, diet and others may be necessary, and will be ascertainable with routine experimentation by those skilled in the art.

In a further preferred embodiment of the present invention, the food composition is capable of altering the gut microbiota in a subject upon administration.

The terms "microbiota" and "microbiome" are used interchangeably herein and relate to microbial communities, preferably bacteria, in and on a subject. Preferably, the terms "microbiota" and "microbiome" as used herein relate to bacterial communities in certain compartments of a subject, preferably gut or intestine.

The term "altering the microbiota" as used herein means in general shifting the structure of the microbiota or the microbial community composition in a host. In particular, the microbiota of a host is altered by increasing or decreasing the abundance of certain bacteria or bacteria families in the host or in certain compartments in the host, e.g. lung or gut. Altering means in this case also an increase in microbial diversity associated with the host. In case D-tryptophan is used in the treatment, amelioration or prevention of a disease as described herein, altering the microbiota in a subject suffering from an allergic disease as described herein preferably results in a microbiota in the subject that is more comparable to a healthy subject than before altering the microbiota as determined using the Shannon diversity index to estimate bacterial diversity or by determining abundance of certain families of bacteria, such as Lachnospiraceae, Odoribacteraceae, Rikenellaceae and Ruminococcaceae. In this respect, treatment of a subject with D-tryptophan preferably increases abundance of Lachnospiraceae and Odoribacteraceae, decreases abundance of Rikenellaceae and/or increases abundance of Ruminococcaceae to a level comparable to a healthy subject. Preferably, treatment with D-tryptophan re-establishes a healthy microbial community genotype in a subject suffering from an allergic airway disease, such as asthma.

Preferably, the food composition of the present invention is capable of increasing the diversity of the gut microbiota in a subject upon administration. In view of the present disclosure, a person skilled in the art can readily determine the diversity of gut microbiota in a subject. Suitable assays that can be used to determine the diversity of gut microbiota are described elsewhere herein. Preferably, microbiota diversity (e.g. in the gut of a subject) is assessed using the Shannon diversity index or as described herein in section Microbial diversity.

In another preferred embodiment of the present invention, the food composition is a pharmaceutical composition.

Definitions provided herein in context of the food composition apply mutatis mutandis to the pharmaceutical composition.

In a preferred embodiment, the pharmaceutical composition comprises a pharmaceutically acceptable carrier. Examples of suitable pharmaceutical carriers are well known in the art and include phosphate buffered saline solutions, water, liposomes, various types of wetting agents, sterile solutions, etc. Compositions comprising such carriers can be formulated by well known conventional methods. Further pharmaceutically acceptable carriers include, but are not limited to diluents (fillers, bulking agents, e.g. lactose, microcrystalline cellulose), disintegrants (e.g. sodium starch glycolate, croscarmellose sodium), binders (e.g. PVP, HPMC), lubricants (e.g. magnesium stearate), glidants (e.g. colloidal SiO2), solvents/co-solvents (e.g. aqueous vehicle, Propylene glycol, glycerol), buffering agents (e.g. citrate, gluconates, lactates), preservatives (e.g. Na benzoate, parabens (Me, Pr and Bu), BKC), anti-oxidants (e.g. BHT, BHA, Ascorbic acid), wetting agents (e.g. polysorbates, sorbitan esters), anti-foaming agents (e.g. Simethicone), thickening agents (e.g. methylcellulose or hydroxyethylcellulose), sweetening agents (e.g. sorbitol, saccharin, aspartame, acesulfame), flavouring agents (e.g. peppermint, lemon oils, butterscotch, etc), humectants (e.g. propylene, glycol, glycerol, sorbitol). Further pharmaceutically acceptable carriers are (biodegradable) liposomes; microspheres made of the biodegradable polymer poly(D,L)-lactic-coglycolic acid (PLGA), albumin microspheres; synthetic polymers (soluble); nanofibers, protein-DNA complexes; protein conjugates; erythrocytes; or virosomes. Various carrier based dosage forms comprise solid lipid nanoparticles (SLNs), polymeric nanoparticles, ceramic nanoparticles, hydrogel nanoparticles, copolymerized peptide nanoparticles, nanocrystals and nanosuspensions, nanocrystals, nanotubes and nanowires, functionalized nanocarriers, nanospheres, nanocapsules, liposomes, lipid emulsions, lipid microtubules/microcylinders, lipid microbubbles, lipospheres, lipopolyplexes, inverse lipid micelles, dendrimers, ethosomes, multicomposite ultrathin capsules, aquasomes, pharmacosomes, colloidosomes, niosomes, discomes, proniosomes, microspheres, microemulsions and polymeric micelles. Other suitable pharmaceutically acceptable carriers are inter alia described in Remington's Pharmaceutical Sciences, 15th Ed., Mack Publishing Co., New Jersey (1991) and Bauer et al., Pharmazeutische Technologie, 5th Ed., Govi-Verlag Frankfurt (1997). The person skilled in the art will readily be able to choose suitable pharmaceutically acceptable carriers, depending, e.g., on the formulation and administration route of the pharmaceutical composition. These pharmaceutical compositions can be administered to the subject at a suitable dose. The dosage regimen will be determined by the attending physician and clinical factors. As is well known in the medical arts, dosages for any one subject depends upon many factors, including the subject's size, body surface area, age, the particular compound to be administered, sex, time and route of administration, general health, and other drugs being administered concurrently. Preparations for parenteral administration include sterile aqueous or non-aqueous solutions, or suspensions. Examples of non-aqueous solvents are propylene glycol, polyethylene glycol, and injectable organic esters such as ethyl oleate. Aqueous carriers include water, aqueous solutions, or suspensions, including saline and buffered media. Parenteral vehicles include sodium chloride solution, Ringer's dextrose, dextrose and sodium chloride, or lactated Ringer's. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the composition might comprise proteinaceous carriers, like, e.g., serum albumine or immunoglobuline, preferably of human origin. It is envisaged that the composition might comprise, in addition to D-tryptophan further biologically active agents, depending on the intended use of the pharmaceutical composition. Such agents might be agents acting as cytostatica, agents preventing hyperurikemia, agents inhibiting immune reactions (e.g. corticosteroids, FK506), drugs acting on the circulatory system, cytokines and others.

The term "pharmaceutically acceptable" means a non-toxic material that does not interfere with the effectiveness of the biological activity of D-tryptophan according to the present invention.

In a further preferred embodiment, the present invention relates to D-tryptophan for use in the treatment, prevention or amelioration of a disease associated with $T_{reg}$ or $T_H2$ cells in a subject suffering from such a disease.

The term "treatment" as used herein means in the broadest sense medical procedures or applications that are intended to relieve illness. In the present case, the administration of D-tryptophan as described herein is for the treatment, amelioration or elimination of an inflammatory diseases described elsewhere herein and in particular allergic airway diseases, such as asthma.

The term "amelioration" as used herein is synonymous with improvement. If a subject's condition shows amelioration, the subject is clearly better—there is some improvement in her or his clinical condition. For example, it may be an improvement in the subject's condition, if an allergic airway inflammation is reduced.

The term "prevention" as used herein means in the broadest sense medical procedures or applications that are intended to prevent onset of an inflammatory disease described elsewhere herein and in particular allergic airway diseases, such as asthma in a subject at risk of developing such a disease.

The term "disease associated with $T_{reg}$ or $T_H2$ cells" in its broadest sense relates to any disease that can be treated by altering numbers or activity of $T_{reg}$ or $T_H2$ cells in a subject or certain compartments of the subject, e.g. lung, gut, blood, abdomen, liver, kidney, heart, central nervous system, brain, liquor and others. Preferably, such diseases are treated by increasing numbers of $T_{reg}$ cells in the subject, preferably in the lung and/or gut and/or by decreasing numbers of $T_H2$ cells in the subject, preferably in the lung.

$T_{reg}$ cells are regulatory T cells which are a subpopulation of T cells which, e.g. modulate the immune system, maintain tolerance to self-antigens, and/or prevent autoimmune disease. $T_{reps}$ are immunosuppressive and as such suppress or downregulate induction and proliferation of effector T cells. $T_{regs}$ may express the biomarkers CD4, FOXP3, and CD25.

$T_H2$ cells are T helper cells of type 2. They are, e.g. triggered by IL-4 and their effector cytokines are IL-4, IL-5, IL-9, IL-10 and/or IL-13. The main effector cells are eosinophils, basophils, and mast cells as well as B cells. They typically express CD4. $T_H2$ cells differ from $T_H1$ cells in their cell surface glycans (oligosaccharides).

In a preferred embodiment, the use of D-tryptophan in the treatment, prevention or amelioration of a disease, as described herein, comprises the step of administering to a subject a therapeutically effective dose of D-tryptophan.

The term "administration" as used herein means administration of a therapeutically effective amount of D-tryptophan to a subject. By "therapeutically effective amount" is meant a dose that produces the effects for which it is administered, e.g. to increase numbers of $T_{reg}$ cells, decrease numbers of $T_H2$ cells, treat, ameliorate or prevent an allergic disease as described herein, or increase gut microbial diversity. A typical dose can be, for example, in the ranges set forth in the embodiments of the food composition of the invention and the appended examples; however, doses below or above this exemplary range are envisioned.

In a preferred embodiment, the present invention relates to D-tryptophan for use in the treatment, prevention or amelioration of an allergy.

The term "allergy" as used herein means any type of hypersensitivity reaction to an environmental allergen mediated by immunological mechanisms. Allergic reactions occur to normally harmless environmental substances known as allergens; these reactions are acquired, predictable, and rapid. Common allergic reactions include eczema, hives, hay fever, asthma, food allergies, and reactions to the venom of stinging insects such as wasps and bees. Mild allergies like hay fever are highly prevalent in the human population and cause symptoms such as allergic conjunctivitis, itchiness, and runny nose. Allergies can play a major role in conditions such as asthma. In some people, severe allergies to environmental or dietary allergens or to medication may result in life-threatening anaphylactic reactions and potentially death.

In a further preferred embodiment, the present invention relates to D-tryptophan for use in the treatment, prevention or amelioration of an allergic airway disease.

The term "allergic airway disease" as used herein relates to an allergic disease of the airways characterized by airway inflammation, airway obstruction and/or hyperresponsiveness and others. Examples of allergic airway diseases are Asthma and allergic rhinitis.

In a further preferred embodiment, the present invention relates to D-tryptophan for use in the treatment, prevention or amelioration of asthma.

The term "asthma" as used herein relates to a chronic inflammation of the upper airways and comprises any known clinical phenotype, such as nonallergic asthma and allergic asthma, but preferably relates to allergic asthma. Asthma is a complex and heterogeneous chronic inflammation of the upper airways caused by a hypersensitivity of the bronchial system against different environmental stimuli. The disease leads to structural and functional changes in the lungs, including goblet cell hyperplasia, airway smooth muscle hypertrophy and subepithelial fibrosis in the airways that in turn give rise to airway hyperresponsiveness (AHR) and reversible airflow limitation. The processes that underlie asthma are characterized by different patterns of cytokine-based inflammation involving diverse cell types such as T cells, B cells, mast cells, eosinophils, basophils, neutrophils and dendritic cells, as well as structural cell types including epithelial, smooth muscle and mesenchymal cells. The most important cause of asthma is a reduced diversity of the microbiota, in particular during infancy or adolescence, leading to a modulation of the immune response.

In another preferred embodiment, the present invention relates to D-tryptophan for use in the treatment, prevention or amelioration of a disease as described herein, wherein D-tryptophan is administered to the subject in an amount sufficient to increase the serum level of D-tryptophan.

In this respect, amounts of D-tryptophan that can be administered to a subject can be for example in the range of 0.01 mg/d to 100 g/d or preferably 0.1 mg/d to 100 g/d. In case of mice, the present inventors could show that oral supplementation with 0.9 mg/d D-tryptophan increased D-tryptophan serum levels significantly. Therefore, a skilled person can easily calculate a possible starting dose for any subject, by adjusting this amount to the weight of the subject. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. The attending physician and clinical factors will determine the dosage regimen. As is well known in the medical arts, dosages for any one subject depends upon many factors, including the subject's size, body surface area, age, the particular compound to be administered, sex, time and route of administration, general health status, and other drugs being administered concurrently. A typical dose can be, for example, in the ranges set forth in the embodiments of the invention and the appended examples; however, doses below or above this exemplary range are envisioned, especially considering the aforementioned factors.

In a further preferred embodiment, the present invention relates to D-tryptophan for use in the treatment, prevention or amelioration of a disease as described herein, wherein D-tryptophan is capable of altering the gut microbiota in a subject upon administration.

Figure 7B:
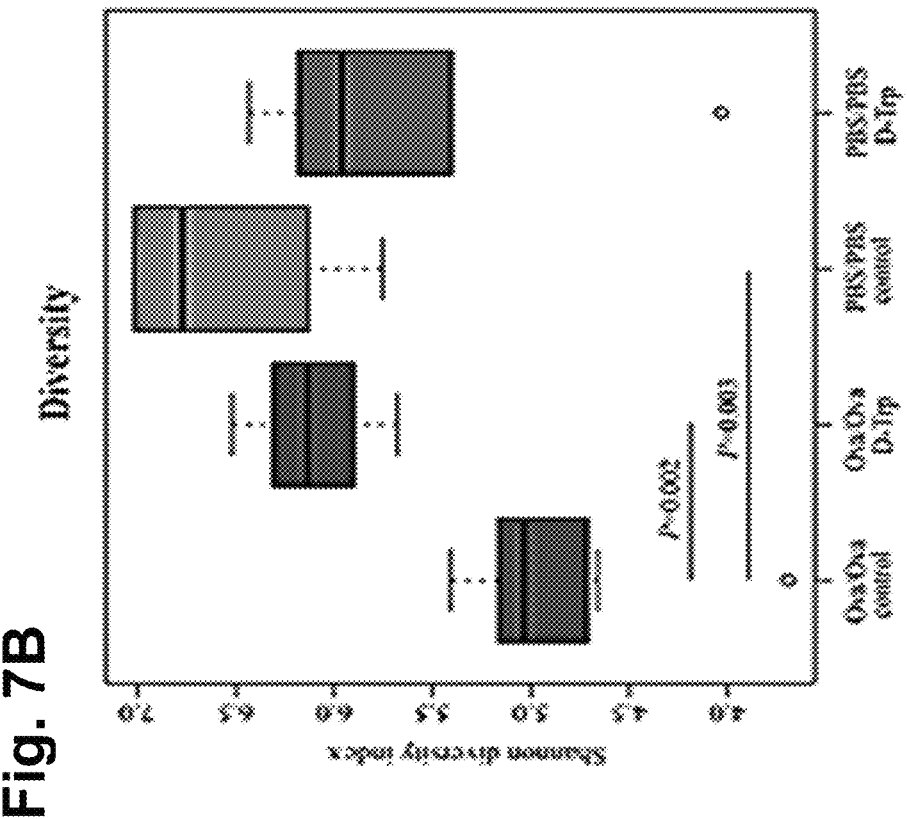
FIG. 7B is a graph of Alpha diversity of bacterial communities.

The present inventors show in a diversity analysis of bacteria by 16S rRNA based barcoding a strongly reduced community richness and diversity of gut microbiota in AAI mice (FIG. 7B). Supplementation with D-tryptophan increases the bacterial diversity in AAI mice, resulting in diversity patterns more comparably to healthy animals. Therefore, the use of D-tryptophan in the treatment of a disease as described herein, preferably increases diversity the gut and/or lung microbiota in a subject upon administration. Even more preferably, the use of D-tryptophan in the treatment of a disease as described herein increases diversity of the gut microbiota in a subject suffering from an allergy, such as an allergic airway disease and in particular asthma, upon administration, preferably resulting in a diversity pattern more comparable to a healthy subject. In view of the present disclosure, a person skilled in the art can readily determine the diversity of gut microbiota in a subject. Suitable assays that can be used to determine the diversity of gut or lung microbiota are described elsewhere herein. Preferably, microbiota diversity (e.g. in the gut of a subject) is assessed using the Shannon diversity index or as described herein in the section Microbial diversity.

The term "AAI mice" as used herein relates to mice in which an allergic airway inflammation has been induced. Preferably, a laboratory mouse strain, e.g. Balb/c mice, is used for induction of an allergic airway inflammation. An allergic airway inflammation can be induced in mice as described herein in detail. Briefly, mice are sensitized i.p. using 10 µg of ovalbumin in alum at day 0, 7 and 14 and challenged intranasally under isoflurane narcosis with 10 µg of ovalbumin in 20 µl PBS.

The mode of administration can be any mode of administration that results in the treatment, amelioration or prevention of disease in the subject. In a preferred embodiment, the present invention relates to D-tryptophan for use in the treatment, prevention or amelioration of a disease as described herein, wherein D-tryptophan administration to the subject is oral, intravenous, subcutaneous, parenteral, transdermal, intraperitoneal, intramuscular or pulmonary administration. Likewise, D-tryptophan may be administered by inhalation. In this respect, the present inventors developed highly sensitive assays, described elsewhere herein, which allowed demonstrating systemic distribution of D-tryptophan in mice after oral uptake for the first time.

In a further preferred embodiment, the present invention relates to D-tryptophan for use in the treatment, prevention or amelioration of a disease as described herein, wherein D-tryptophan modulates the immune response and/or alters the gut or lung microbiota in the subject upon administration. Preferably, D-tryptophan alters the gut microbiota in the subject upon administration The term "modulating the immune response" as used herein relates to modulating any immune response in a subject, either innate or adaptive. The immune response can be directly modulated using D-tryptophan by exerting an effect on cells from the subject involved in the immune response, e.g. by increasing or decreasing cell numbers, in particular numbers of immune cells, altering signal transduction, altering expression of certain cell surface molecules, e.g. receptors, altering cellular metabolism, altering secretion of cytokines or chemokines involved in the immune response, e.g. CCL17, IL-4, Gata3 or IL-13, modulating the profile of certain cells of the immune system, preferably towards a tolerogenic profile, e.g. in dendritic cells, and others. The immune response can also be indirectly modulated using D-tryptophan by shifting the structure of the microbiota of the host. Preferably, modulating the immune response in a subject results in reduction of a chronic inflammation, a reduced immune response against allergens, or treatment of a chronic immune disease, such as asthma, allergies, inflammatory bowel disease, or diabetes.

The present inventors surprisingly discovered, in the bioassays described elsewhere herein, that cells of a subject, e.g. a human subject, respond to D-tryptophan but to neither L-Tryptophan nor any other tested D-amino acid. Without being bound by theory, D-tryptophan could at least partially exert its effect via the G protein-coupled receptor GPR109B, which is expressed on macrophages, monocytes, adipose tissue, T cells and lung. The present inventors surprisingly discovered that GPR109B is significantly decreased in airway epithelial cells and T cells from subjects with asthma as opposed to control subjects. Furthermore, D-tryptophan could at least partially exert its effect via the receptor solute carrier family 6 amino acid transporter member 14 (SLC6A14, alias ATB$^{0,+}$), which is expressed in the intestine and transports D-tryptophan across epithelial cells.

In a further preferred embodiment, the present invention relates to D-tryptophan for use in the treatment, prevention or amelioration of a disease as described herein, wherein modulating the immune response is increasing $T_{reg}$ cells in the lung and/or in the gut, reducing $T_H2$ cells in the lung and/or reducing IL-4, Gata3 and IL-13 T cell secretion in the subject compared to a subject who has not been treated with D-tryptophan. In a preferred embodiment, Helios$^+$ $T_{reg}$ cells are increased in the lung and/or Foxp3$^+$ T cells are increased in the colon in the subject compared to a subject who has not been treated with D-tryptophan. In another preferred embodiment, treatment with D-tryptophan improves airway hyperreactivity or airway hyperresponsiveness to methacholine in the subject compared to a subject who has not been treated with D-tryptophan. In another preferred embodiment, treatment with D-tryptophan reduces Il-4-producing T cells and/or Il-4 levels in bronchoalveolar lavage fluid.

In a further preferred embodiment, the present invention relates to D-tryptophan for use in the treatment, prevention or amelioration of a disease as described herein, wherein modulating the immune response is reducing number of dendritic cells expressing costimulatory molecules (i.e. inducing a tolerogenic profile in the dendritic cells); increasing secretion of IL-10 of dendritic cells and/or decreasing secretion of IFN-g, IL-12 and IL-5 of dendritic cells of the subject compared to a subject who has not been treated with D-tryptophan.

In case D-tryptophan is used in the treatment, prevention or amelioration of a disease as described herein, the term "subject" relates to an animal, preferably a mammal and more preferably a human that suffers from or is at risk of developing an inflammatory disease described elsewhere herein, in particular an allergic airway disease, such as asthma. In this context, a healthy subject does not suffer from an inflammatory disease as described elsewhere herein and preferably does not suffer from an allergic airway disease, such as asthma.

In a further preferred embodiment, the present invention relates to D-tryptophan for use in the treatment, prevention or amelioration of a disease as described herein, wherein altering the gut or lung microbiota in the subject is increasing gut or lung microbiota diversity in the subject, wherein abundance of Lachnospiraceae and Odoribacteraceae is increased, abundance of Rikenellaceae is decreased and/or abundance of Ruminococcaceae is restored in the subject to a level more comparable to a healthy subject. Preferably, the above described abundance of bacteria at the family level is altered in the gut or lung of the subject and even more preferably in the gut of the subject.

In a further preferred embodiment, the present invention relates to D-tryptophan for use in the treatment, prevention or amelioration of a disease as described herein, wherein D-tryptophan decreases the number of bronchoalveolar lavage fluid cells, e.g. eosinophils or Il-4-producing T cells, in the subject, compared to a subject who has not been treated with D-tryptophan. Preferably, treatment with D-tryptophan decreases Il-4-producing T cells in bronchoalveolar lavage fluid.

In a further preferred embodiment, the present invention relates to D-tryptophan for use in the treatment, prevention or amelioration of a disease as described herein, wherein D-tryptophan decreases airway hyperreactivity in the subject, compared to a subject who has not been treated with D-tryptophan.

Airway hyperreactivity is preferably assessed by challenging a subject with methacholine and measuring Resistance and/or Compliance as described herein in detail.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "more than" does not include the concrete number.

For example, less than 20 means less than the number indicated. Similarly, more than or greater than means more than or greater than the indicated number, e.g. more than 80% means more than or greater than the indicated number of 80%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

A better understanding of the present invention and of its advantages will be had from the following examples, offered for illustrative purposes only. The examples are not intended to limit the scope of the present invention in any way.

FIGS. 1A-5B: Screening of supernatants from different of probiotic strains for immune activity on human cells. A, Dose-dependent capacity of bacterial supernatants from *Lactobacillus rhamnosus* GG (-●-), *Bifidobacterium* BB-420 (-▼-) and *Lactobacillus casei* W56 (-■-) to lower CCL17 secretion of human Hodgkin lymphoma KM-H2 cells. Negative control: non-probiotic *Lactobacillus* DSM-20021 (-▲-). Three independent experiments in duplicates (mean percentages±SD, relative to CCL17 secretion of untreated KM-H2 cells). Student's t test; p≤0.005, *p≤0.0005; L. casei W56: ##p<0.005, ###p<0.0005, BB-420: §§p<0.005, §§§p<0.0005; B1-B5, Capacity of supernatants from *Lactobacillus rhamnosus* GG, *Bifidobacterium* BB-420, *Lactobacillus casei* W56 or non-probiotic *Lactobacillus* DSM-20021 to prevent full upregulation of costimulatory molecules and HLA-DR on LPS stimulated human monocyte derived dendritic cells. +/− with/without bacterial supernatant. Five independent experiments (mean percentages±SD relative to LPS alone). Dunn's Multiple Comparison Test; p<0.01, *p<0.001.

FIGS. 2A-2D: Overview on the ability of bacterial supernatants from all 37 strains to lower CCL17 secretion of KM-H2 cells. Shaded bars: non-probiotic *Lactobacillus* DSM-20021 (negative control); *L. rhamnosus* GG was included as positive control in all experiments with strains other than Lactobacilli. White bars: untreated KMH2 and medium controls. Three independent experiments in duplicates (mean percentages+SD, relative to CCL17 secretion of untreated KM-H2). Student's t test; p<0.005 and *p<0.0005.

Figure 3A:
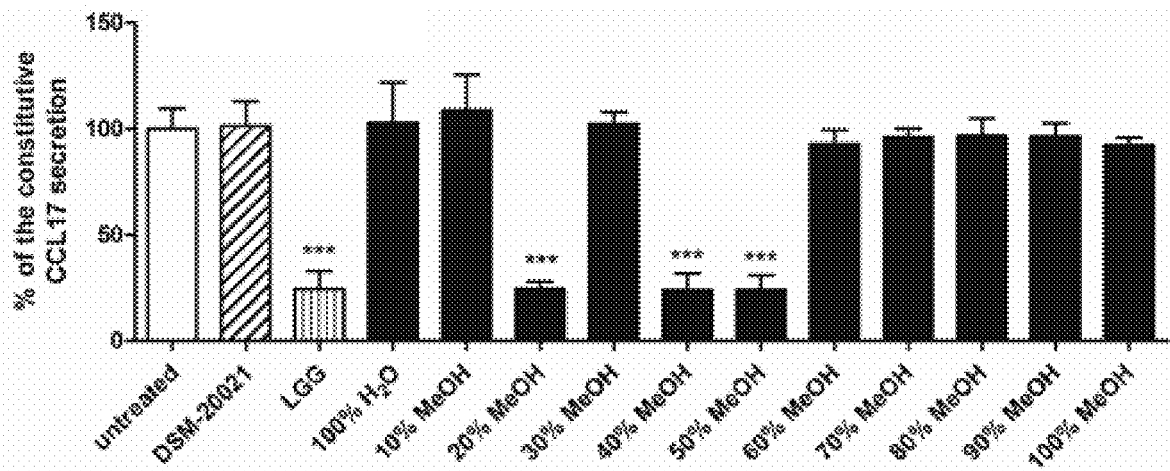
FIGS. 3A-3C are graphs showing the capacity of subfractions of probiotic supernatants to lower CCL17 secretion in KM-H2 cells.
Figure 3B:
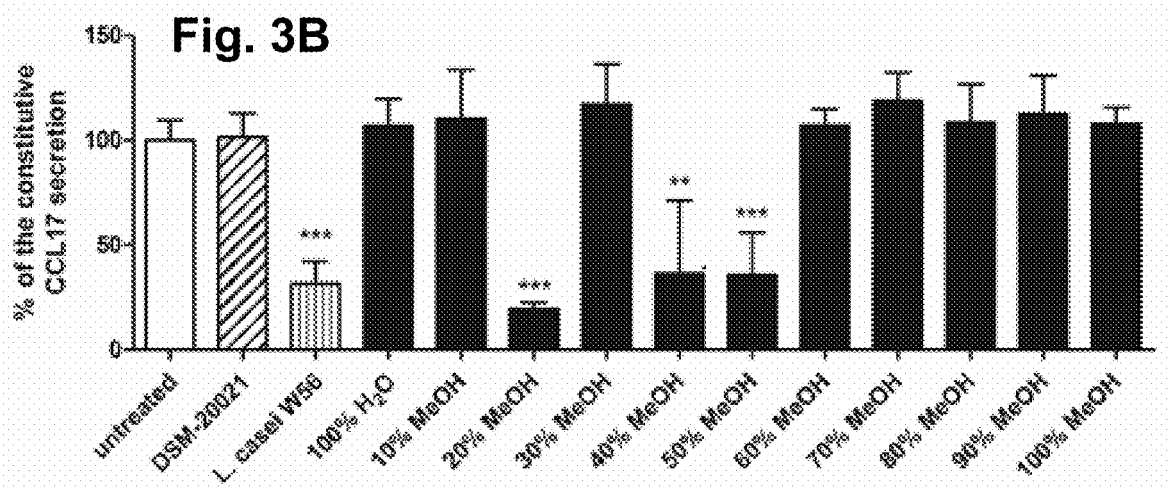
Figure 3C:
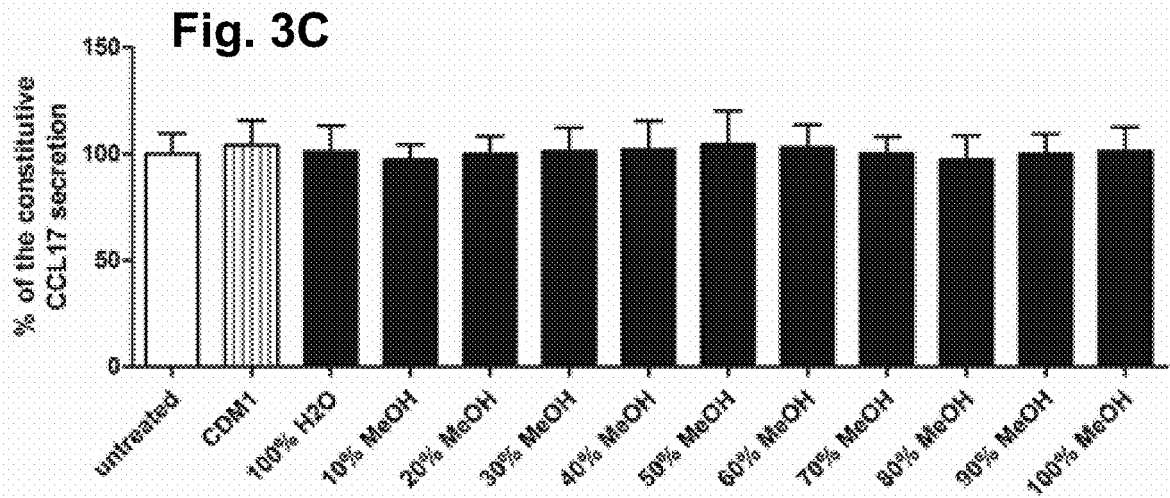

FIGS. 3A-3C: Capacity of subfractions of probiotic supernatants to lower CCL17 secretion in KM-H2 cells. Subfractions with different polarity (MeOH/H2O gradient chromatography) from supernatants of *Lactobacillus rhamnosus* GG (top), *Lactobacillus casei* W56 (middle), Negative controls: Non-probiotic DSM-20021 and blank CDM1 medium (bottom). Three independent experiments in duplicate (mean percentages±SD, relative to constitutive CCL17 secretion of untreated KM-H2 cells). Student's t test; p<0.005, *p<0.0005.

FIG. 4: Effect of tryptophan L- and D-isomers on CCL17 secretion by KM-H2 cells KM-H2 cells were stimulated with different concentrations of synthetic L-and D-isomers of tryptophan followed by CCL17 quantification in KM-H2 culture media after 24 h. (●) D-tryptophan, (♦) L-tryptophan. Three independent experiments in duplicates (mean percentages±SD, relative to constitutive CCL1 7 secretion of untreated KM-H2 cells). Student's t test; *p<0.05, p<0.005, *p<0.0005.

FIGS. 5A1-5G: Oral D-tryptophan reduces allergic airway inflammation. A1 and A2, Serum D-tryptophan in mice receiving D-tryptophan (50 mM) in drinking water or water only (UPLC-MS peak areas). Note the different scales for D-tryptophan (black bars) and L-tryptophan (grey bars). Welch Test, mean±SD, p=0.006, *p=0.004. B, Total number of cells in BALF. C, Differential cell count, D, Measurement of airway resistance to increasing doses of methacholine. Two-way ANOVA with Bonferroni post-test. E1 and E2, Geometric mean of Ifn-g and Il-4 in lung-derived $CD3^+CD4^+$ lymphocytes. F, Il-4 levels in BALF of mice, assessed by CBA. G, Helios+ Tregs of lung-derived $CD3^+$ $CD4^+$ $Foxp3^+$ lymphocytes, n=6-12 mice per group, Student's T-Test, *p<0.05, p<0.01, *p<0.001 (FIG. 5B,C, E, F) n=8 mice per group, Mann-Whitney U.

FIGS. 6A1-C2: D-Trp influences in vitro primary T cell differentiation. Primary, murine splenocytes were differentiated towards, Th1 (A1 and A2), Th2 (B1-B6), and Treg (C1-C2) with respective cytokine mixes under the presence of 0, 10 or 50 μM D-Trp (dissolved in water). Differentiation was assessed by flow cytometry, qRT-PCR and CBA for Il-13 and Il-5 protein levels from culture supernatants. Graphs depict fold changes to differentiated cells not treated with D-Trp. n=3-4 independent experiments, Mann-Whitney U, *p<0.05.

Figure 7A:
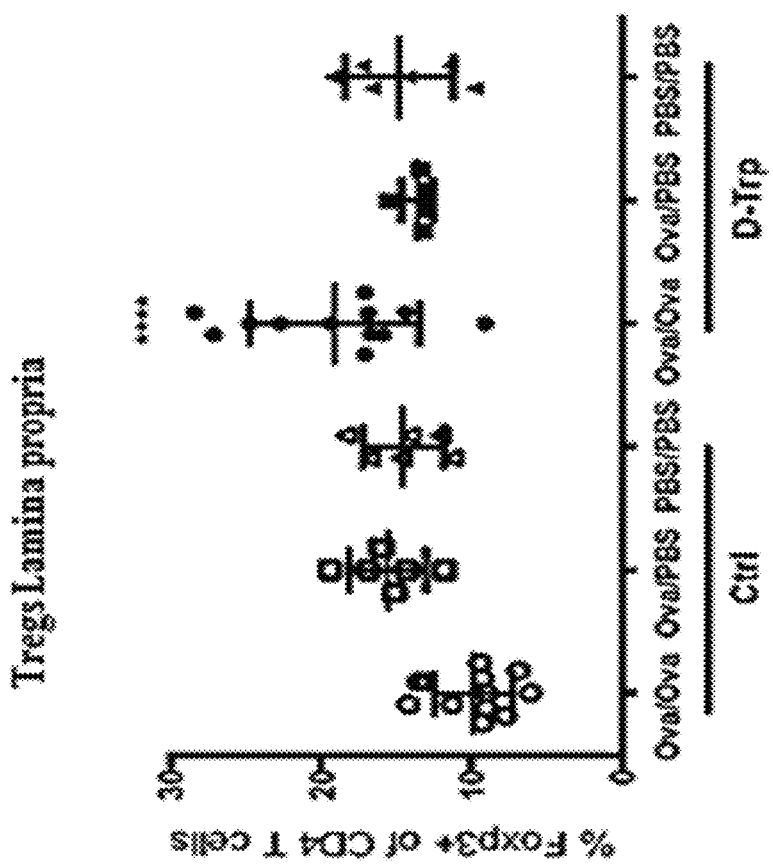
FIG. 7A is a graph of the Percentage of Foxp3$^+$ cells within CD3$^+$CD4$^+$ T cells in lamina propria of the colon.

FIGS. 7A and 7B: Oral D-tryptophan supplementation increased gut Treg and the intestinal bacterial community in mice with AAI. A, Percentage of $Foxp3^+$ cells within $CD3^+$ $CD4^+$ T cells in lamina propria of the colon. n=6-12 mice per group, Student's t test.***P<0.0001. B, Alpha diversity of bacterial communities. Shannon diversity index was used to estimate bacterial diversity for each treatment. Wilcoxon rank-sum test.

FIGS. 8A1-8B8: Kinetic and volumes of supernatants from probiotic bacteria able to lower CCL17 secretion from KM-H2 cells. A1-A8, Capacity of supernatants from bacteria cultured in rich MRS medium to lower CCL17 secretion of KM-H2 cells. B1-B8, Capacity of supernatants from bacteria cultured in restricted CDM1 medium to lower CCL17 secretion of KM-H2 cells (■2 h; ● 6 h; ▲ 12 h; ♦24 h; ▼48 h). Data are shown each from three independent experiments in duplicate (mean percentages±SD, relative to constitutive CCL17 secretion of untreated KM-H2).

FIG. 9A1-9D2: Viability of KM-H2 cells and primary DCs. Viability analysis of KM-H2cells (upper panel, A1, B1, C1) and primary DCs (lower panel, A2, B2, C2) after treatment with probiotic supernatants with trypanblue (A1, A2), 7-AAD staining (B1, B2) and photometric analysis after treatment with CellTiter-Blue® reagent (C1, C2). D1 and D2, Purity assessment of primary DCs via flow cytometry before (left panel, D1) and after LPS stimulation (right panel, D2) (representative image).

Figures 10A, 10B:
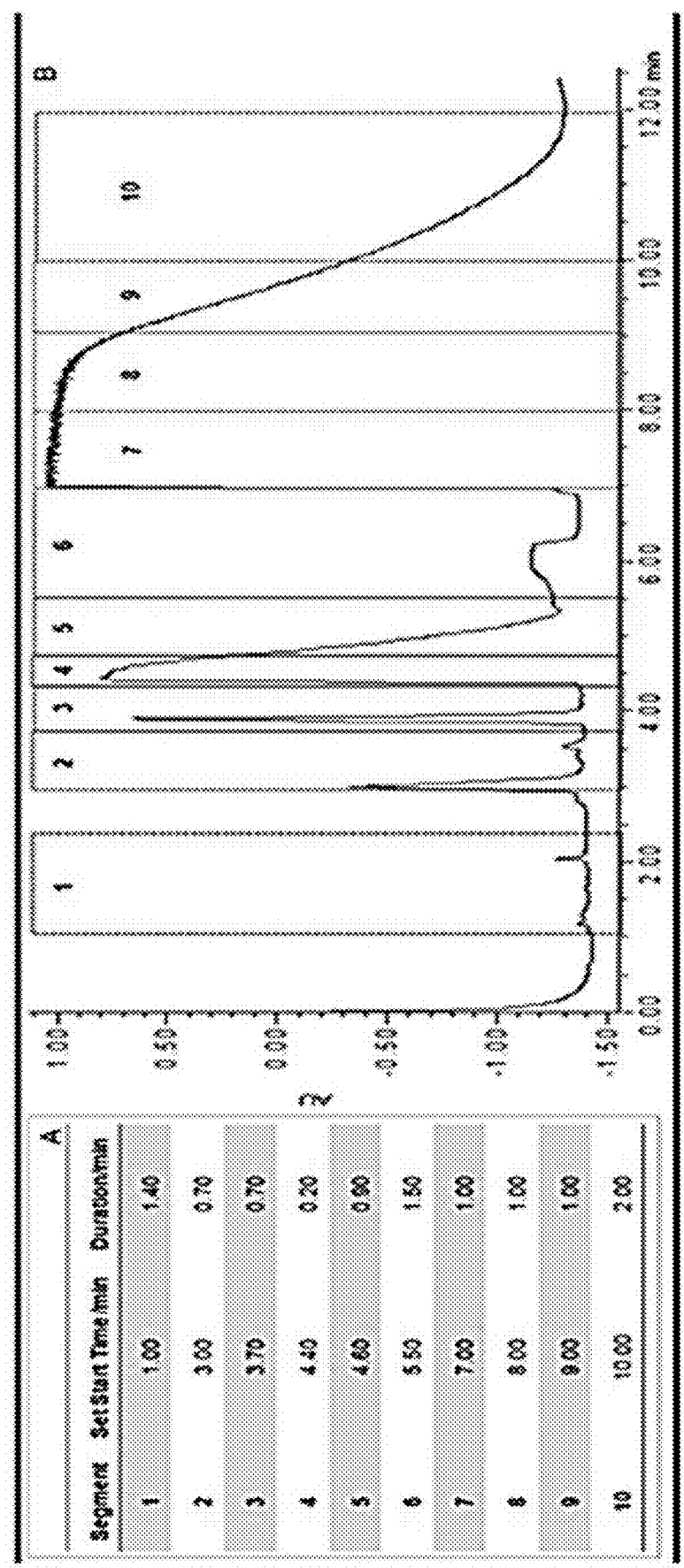
FIG. 10A is a table with data from a UPLC-PDA chromatogram of 20% MeOH/H2O extract from *L. casei* W56 supernatant.
FIG. 10B is a graph showing chromatogram peaks.

FIGS. 10A and 10B: UPLC-PDA chromatogram of 20% MeOH/H2O extract from *L. casei* W56 supernatant. A, Sub-fractions and their time of collection were decided based on the peaks observed in the chromatogram. B, Immune modulatory activity was observed for sub-fractions 7, 8 and 9. Chromatographic conditions: Kinetex PFP column 1.7 μm particle size, 2.1×150 mm. Nonlinear gradient in 10 min from 5 to 25% B, 14 min to 100% B at 40° C. with 0.180 mL/min flow rate (Mobile phase A: 10% MeOH/H2O; B: 100% MeOH).

FIGS. 11A-11D: UPLC-URH-TOF MS analyses of *L. casei* W56 and LGG bioactive sub-fractions and their nearest neighbors. A, Total ion chromatograms in ESI+ using reversed phase chromatography (C18 column: 1.7 μm, 2.1× 150 mm) showing a peak at $t_R$ 4.2 min for all bioactive sub-fractions. B, Extracted mass spectra corresponding to the chromatographic time range of 4.1-4.3 min. The same signal profile was observed for all bioactive sub-fractions, where m/z 409.1875, 205.0971 and 188.0702, strongly agree with the Tryptophan ions [2M+H]+, [M+H]+ and its fragment [M+H−NH3]+. C, and D, FT-ICR-MS spectra of the purified bioactive sub-fraction 7 of LGG in ESI negative mode and ESI positive mode respectively. The assigned molecular formula is $C_{11}H_{12}N_2O_2$ with an error <0.01 ppm.

Figures 12A, 12B, 12C:
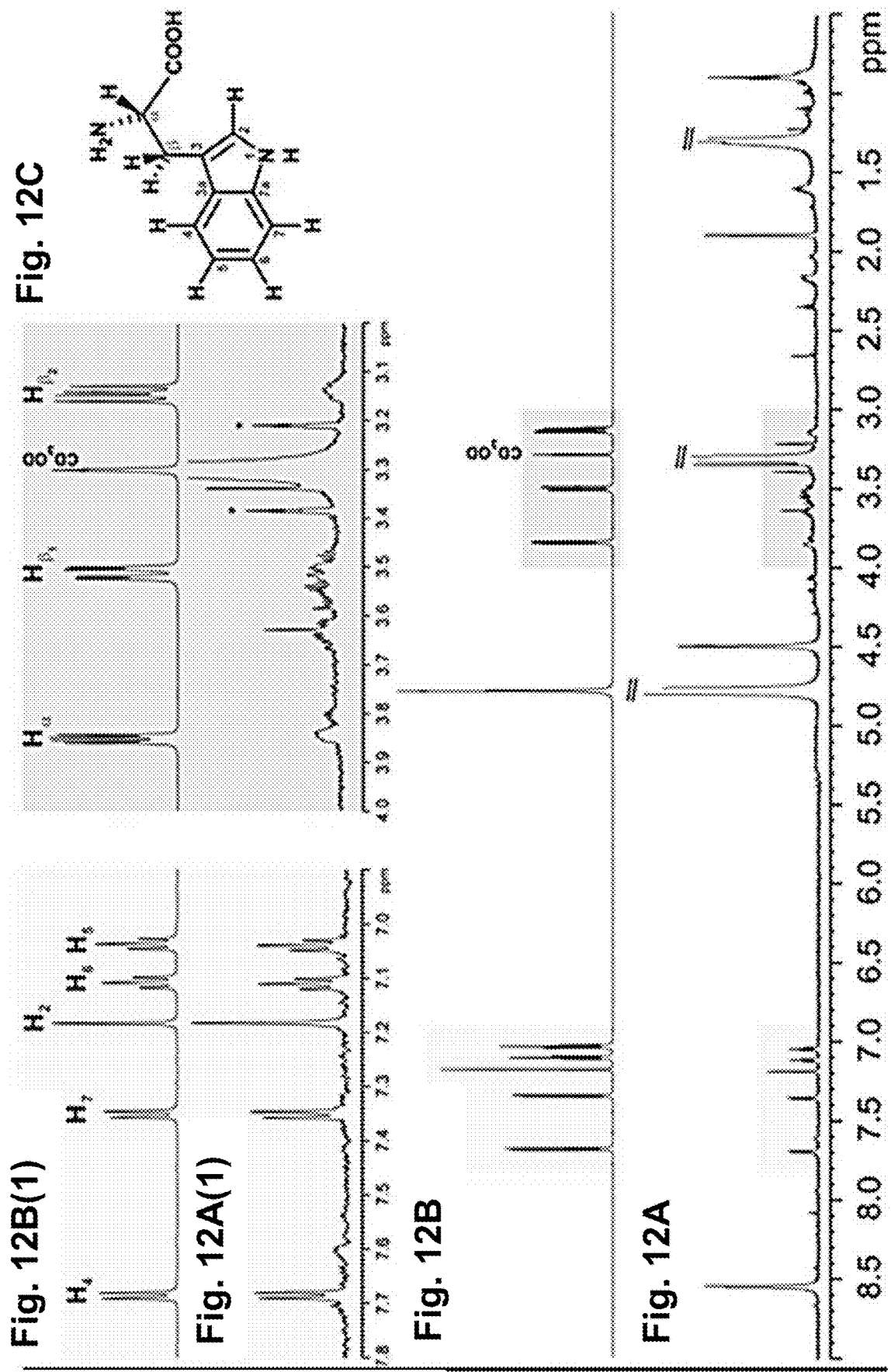
FIG. 12A is a graph of a 800 MHz $^1$H NMR spectrum of probiotic bacterial supernatant.
FIG. 12B is a graph of a 800 Hz $^1$H NMR spectrum of L-Tryptophan (FIG. 12C) in CD3OD.

FIGS. 12A-12B: Proton-NMR spectra of probiotic bacterial supernatant and L-Tryptophan. The upper panel of both figures (FIGS. 12A(1) and 12B(1)) shows an enlargement of the shaded areas in the lower panel (FIGS. 12A and 12B). A, 800 MHz $^1$H NMR spectrum of probiotic bacterial supernatant; note the low sample concentration (asterisk: $^{13}$C satellites at 0.5% intensity of HCD2OD with 99.95% $^2$H). Aromatic spin systems can be recognized, including J-couplings, whereas aliphatic nuclei show partial splitting due to low signal to noise (S/N) ratio. B, 800 Hz $^1$H NMR spectrum of L-Tryptophan in CD3OD with aromatic (yellow) and aliphatic (green) spin systems indicated (note: D- and L-Tryptophan produce identical NMR spectra in achiral solvents).

Figure 13B:
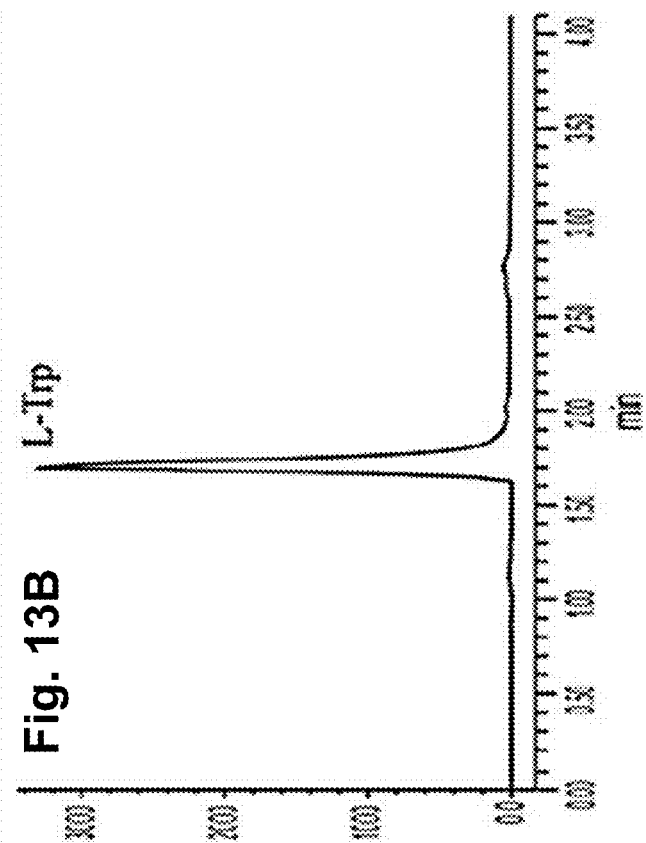
FIG. 13B is a graph of a corresponding sub-fraction of blank CDM1 medium.
Figure 13A:
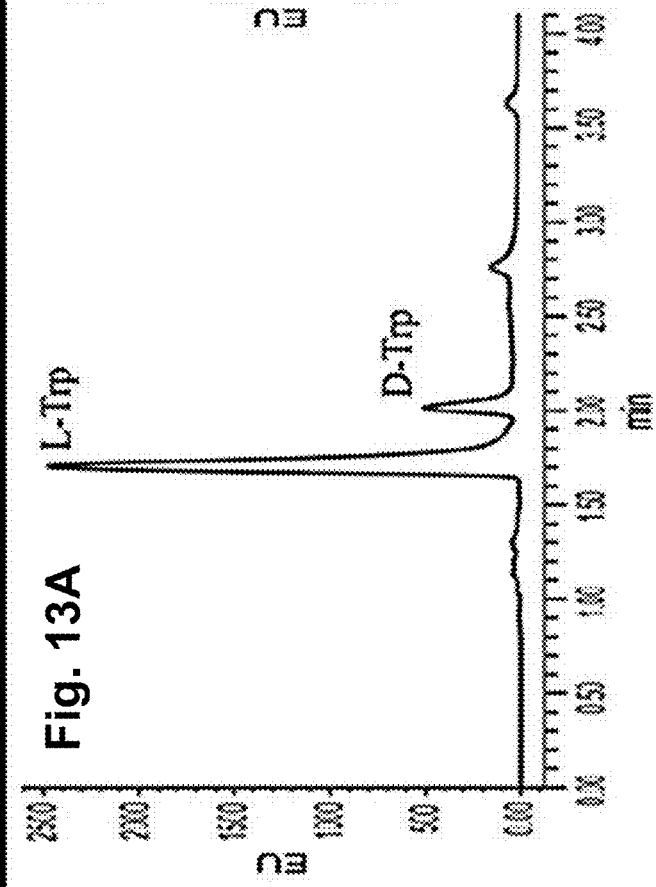
FIG. 13A is a graph of UPLC-FLD chromatogram from a purified bioactive sub-fraction LGG.

FIGS. 13A and 13B: Comparative UPLC-FLD chromatogram from the purified bioactive sub-fraction. Comparative UPLC-FLD chromatogram from the purified bioactive sub-fraction. Panel A: Subfraction 7 from LGG; Panel B: corresponding sub-fraction of blank CDM1 medium. Enantiomer separation of Tryptophan derivatized with OPA-IBLC shows the presence of D-Tryptophan only in the bioactive sub-fraction.

FIGS. 14A-14D2: Oral D-Tryptophan supplementation ameliorates allergic airway inflammation. A, Treatment scheme for induction of allergic airway inflammation, D-Trp was supplied in drinking water from day −3 in respective groups. B, Measurement of airway resistance to increasing doses of methacholine. C1 and C2, Percent Il-4+ and Il-13+ cells within spleen CD3+CD4+ T cells. D1 and D2, CD40+ and CD80+ on spleen CD11b$^{high}$DCs, Box and whisker plots: Maximum and minimum values (whiskers), the upper and lower quartiles (boxes) and median (horizontal line). (A) 7-8 mice/group, mean±SD, Two-way ANOVA with Bonferroni post-test. *p<0.05, ***p<0.001.

FIGS. 15A1-15B5: In vitro differentiation of primary T cells. Murine naïve CD4+ cells were differentiated in vitro for 6 days with respective cytokines. Gating strategy for analysis of (A) Th1 & Th2 cells as assessed by CD4+Ifny+ or CD4+Il4+, respectively, and induced Tregs as CD4+ CD25+Foxp3+ cells (B). Representative images of n=4 independent experiments.

FIGS. 16A-16B4: Influences of D-Tryptophan supplementation on the intestinal bacterial composition in healthy and diseased mice. A, An unweighted UniFrac distance matrix based on OTU counts was used to perform Principal Coordinate Analysis (PCoA). The generated scatterplot indicates dissimilarities between individual samples. Statistical significance was determined with Student's t test, P=0.001. All results are based on 95%-similarity OTUs. OTU, operational taxonomic unit. PC, principal coordinate. Ova, ovalbumin. PBS, phosphate buffered saline. B1-B4, Proportion of dominant bacteria (>0.05% abundance) in the intestinal tract of healthy and diseased mice. Pie charts were generated to visualize the relative distribution of the most abundant bacteria at the family level.

Figure 17:
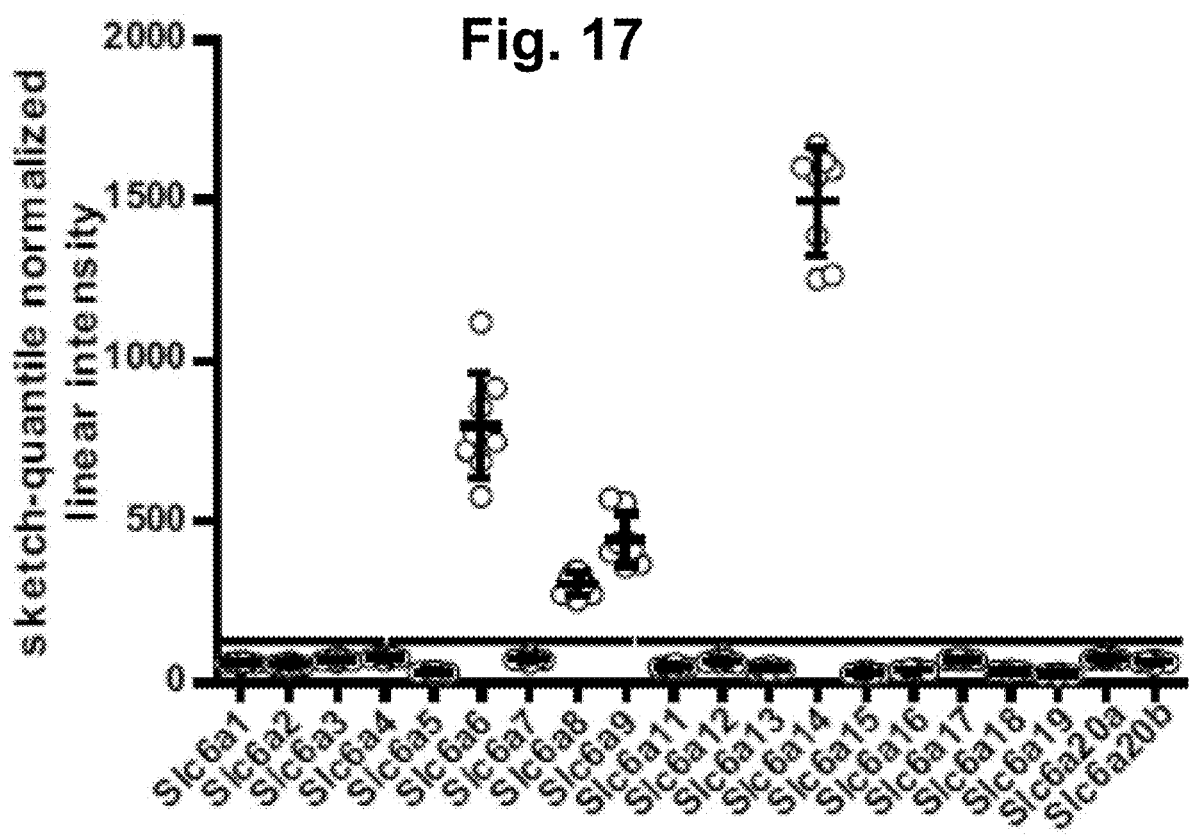
FIG. 17 is a graph of expression of Slc6a family members in lungs of neonatal mice.

FIG. 17. Expression of Slc6a family members in lungs of neonatal mice Sketch-quantile normalized linear intensity (mean±SD). Background levels (dashed line). Male and female neonates (n=4 each).

EXAMPLES

The following Examples illustrate the invention, but are not to be construed as limiting the scope of the invention.

Reagents. L-Tryptophan and D-amino acids (A, F, H, I, L, M, P, S, T, V, W, Y) were purchased from Carl Roth GmbH, Karlsruhe, Germany.

Growth conditions of bacterial and collection of supernantants. For the primary screen of bioactivity, probiotic strains were grown in complex de Man-Rogosa-Sharpe (MRS) medium (Applichem, Darmstadt, Germany) at 37° C. under microaerobic conditions in an Incubator (Thermo Fisher Scientific, Waltham, USA). For metabolite analyses, the strains were grown in modified defined medium CDM1 (Savijoki et al., Lett Appl Microbiol. 2006 March; 42(3): 202-9.) which contains L-Tryptophan among 19 other L-amino acids, at 37° C. In contrast to the original medium, we omitted Tween 80, as it is known to interfere with mass spectrometric analyses (Müller et al., J Chromatogr A. 2014 Jan. 10; 1324:109-14.). E. Coli Nissle 1917 was grown aerobically in Luria-Bertani (LB)-Medium on a rotary shaker (New Brunswick Scientific, Enfield, USA) (200 rpm) at 37° C.

Generation of human monocyte-derived dendritic cells. Peripheral venous blood was obtained from healthy volunteers aged between 20 and 50 years after informed consent. Individuals with allergic disease, acute infection or taking any medication 20 days prior to blood sampling or any history of smoking (personal interview) were excluded prior to blood sampling. All experiments were conducted according to the principles expressed in the Declaration of Helsinki.

Peripheral blood mononuclear cells (PBMC) were isolated from heparinized whole blood by density gradient centrifugation (2000 rpm, 22° C., 20 min) (Biocoll, Biochrom AG, Berlin, Germany). Adherent monocytes were obtained from PBMC via plastic adherence in 12-well plates (Nunc, Wiesbaden, Germany) in 1.5 mL very low endotoxin (VLE) RPMI 1640 medium (Biochrom AG, Berlin, Germany) supplemented with 5% human serum type AB (CELLect®, MP Biomedicals™, Eschwege, Germany) and 1% glutamine (Gibco® Invitrogen, Karlsruhe, Germany) for 1 h. Granulocyte macrophage colony-stimulating factor (GM-CSF) and Interleukin (IL)-4 (CellGenix, Freiburg, Germany) were added on days 1, 3, and 6 at 100 ng/mL and 20 ng/mL, respectively, yielding 2-3×10$^6$ immature DCs per well. Purity and viability of DCs was assessed by flow cytometry (FIG. 9A-C).

Human T cell line KM-H2. The human Hodgkin lymphoma T cell line (KM-H2) was purchased from the Leibniz Institute DSMZ-German Collection of Microorganisms and Cell Cultures, Braunschweig, Germany. 3-5×10$^6$ KM-H2 cells were grown in 4 mL RPMI 1640 per well in 6-well-plates (Nunc, Wiesbaden, Germany). All eukaryotic cells were cultured in 5% CO$_2$ at 37° C. (HeraCell 240 and Heraeus BDD 6220, Thermo Fisher Scientific, Waltham, USA). Viability of cells after treatment with bacterial supernatants was assessed by trypan blue, 7-AAD and CellTiter-Blue® staining. (FIG. 9A-C)

Isolation of intestinal lamina propria cells. Total colons were excised from mice, removed from mesenteries, opened longitudinally and cut into 2 cm long pieces that were incubated for 30 min in 30 mM EDTA in PBS on ice and then shaken vigorously with PBS to remove epithelial cells. After further cutting into small pieces with sharp scissors these were digested at 37° C. in RMPI supplemented with 1 mg/mL collagenase D (Roche Diagnostics, Mannheim, Germany) and 10 mg/ml DNAse I (Sigma-Aldrich, St. Louis, USA). Cells were separated by a 40/80% (w/v) Percoll (GE Healthcare, Chalfont St. Giles, UK) density centrifugation step and washed prior to staining for flow cytometry analysis.

Differentiation of murine primary T cells. Murine spleens from female Balb/c mice were filtered through a 40 μm filter to generate single cell suspensions. These were then subjected to red blood cell lysis by using RBC lysis buffer (Biolegend, San Diego, USA) according to the manufacturer's recommendations. Afterwards, naïve CD4+ T cells were isolated via magnetic-activated cell sorting (MACS) using the naïve CD4+ T cell isolation kit (Miltenyi Biotec, Bergisch-Gladbach, Germany). The resulting naïve CD4+ T cells were cultured in 96 wells plates (1×10$^6$ cells/ml Medium) in TexMACS medium supplemented with 10% FCS, 0.01 mM 2-Mercaptoethanol, rIL-2 (10 ng/ml) as well as MACSiBead particles with anti-CD3 and anti-CD28 (1×10$^6$ beads per 1×10$^6$ cells) (all Miltenyi Biotec). Cells were differentiated over a period of 6 days towards Th1 (10 ng/ml IL12 and 10 μg/ml anti-IL4, derived from Cytobox Th1), Th2 (10 ng/ml Il4 and 10 μg/ml anti-Ifnγ, derived from Cytobox Th2) and Treg (5 ng/ml) (all Miltenyi Biotec). Differentiation of cells was assessed by flow cytometry (see FIG. 15 for gating strategy), enhanced cytometric bead array (CBA) from cell culture supernatants and qRT-PCR. Prior to CBA and flow cytometry, cells were stimulated with monensin (0.7 μL/mL, BD Golgi Stop, BD Bioscience, Heidelberg, Germany) for 4 h at 37° C. in the prescence of Ionomycin (500 ng/ml, Sigma Aldrich, Missouri, USA) and PMA (5 ng/ml, Sigma Aldrich, Missouri, USA).

Flow Cytometry

Costimulatory molecules on human DCs. The following primary monoclonal antibodies were used: CD83 fluorescein isothiocyanate (FITC); CD1a phycoerythrin (PE); CD86-FITC; CD80-PE; CD14 allophycocyanine (APC); CD40-APC; CD3-peridinin chlorophyll protein (PerCP); HLA-DR-PerCP; mouse immunoglobulins $G_1$ (IgG$_1$) mouse immunoglobulins $G_1$ (IgG$_1$) κ were used as isotype controls using the corresponding fluorochromes (all purchased from BD Biosciences, Heidelberg, Germany). To account for donor dependent variability of DC surface markers, all data were normalized to the expression induced by LPS which was set to 100% after subtraction of background values (FACS Canto, FACS DIVA software, Version 5.0.3, BD Biosciences, Heidelberg, Germany). Murine DC subsets and CD4$^+$ T cells. Single cell suspensions of splenocytes were obtained by filtering spleens through a 70 μm strainer. Samples were stained with CD3-PB (1:200, Biolegend, San Diego, USA), CD4-APC-H7 (BD, 1:400), CD11c-APC-Cy7 (1:100), Mhc-II-Percp-Cy5 (1:100), CD11b-FITC (1:100), CD80-AF647, CD40-APC (1:100). For intracellular cytokines, total spleen cells were stimulated with anti-CD3 (4 μg/mL, BD Bioscience, Heidelberg, Germany) and anti-CD28 (30 ng/mL, BD Bioscience, Heidelberg, Germany) for 16 h. $1 \times 10^6$ of total lung cells were stimulated for 16 h with MACSiBead particles coated with anti-CD3 and anti-CD28 using the T cell activation/expansion kit (Miltenyi Biotec, Bergisch Gladbach, Germany) in TexMACS medium (Miltenyi Biotec) according to the manufactures recommendations. Prior to staining, cells were treated with monensin (0.7 μL/mL, BD Golgi Stop, BD Bioscience, Heidelberg, Germany) for 6 h at 37° C. and intracellularly stained for Il-4-PE (1:100, eBioscience, Vienna, Austria according to the manufacturer's protocols. Intracellular staining for Foxp3 was performed by using the Foxp3/Transcription Factor Staining buffer set (eBiosciences, Vienna, Austria) according to the manufacturer's recommendations.

The analysis was performed on an LSRII, with DIVA TM Software v8.0 (BD Bioscience, Heidelberg, Germany), kindly provided by the core unit fluorescence cytometry of the Research Center Borstel.

Assessment of cytokines by cytometric bead array. Levels of Il4, Il5 and Il13 were analysed in BALF and cell culture supernatants using an enhanced cytometric bead array (eCBA, Fex Set Kits, BD Biosciences, Franklin Lakes, N.J., USA) according to the manufacturer's guidelines.

Murine regulatory T cells. Cells were preincubated with Fc-Block (BD Bioscience, Heidelberg, Germany) for 5 min and stained for 20 min with the following antibodies: FITC-conjugated anti-CD3, Alexa-Fluor700-conjugated anti-CD4 and APC-eFluor780-conjugated CD45.2. For intracellular staining, cells were fixed and permeabilized with a commercially available fixation/permeabilization buffer (eBioscience, Vienna, Austria). LIVE/DEAD fixable Aqua dead stain kit (Invitrogen, Carlsbad, USA) was used prior to fixation. Intracellular staining was performed with PerCP-Cy5.5-conjugated anti-Foxp3 and Helios. Gates were set on live CD45$^+$CD3$^+$CD4$^+$ T cells. All antibodies were from eBioscience (Vienna, Austria). Cells were analyzed with a flow cytometer (Fortessa and LSRII, BD Bioscience, Heidelberg, Germany) and analyzed with Flowjo software (Flowjo LLC, Ashland, USA).

Quantification of CCL17 and cytokines in eukaryotic cell culture supernatants. CCL17 was quantified in cell culture supernatants of KM-H2 cells using ELISA reagent Quantikine CCL17/TARC, (R&D Systems, Minneapolis, USA) according to the manufacturer's instructions (ELISA reader MRXII, Thermo Fisher Scientifc, Waltham, USA).

For cytokine analyses, cell-free culture supernatants were collected from DCs after 24 h incubation with either probiotic supernatants or D-Tryptophan, and were stored in aliquots at −80° C. before analysis. For probiotic supernatants, blank CDM1 was used as medium control. For D-Tryptophan the present inventors used L-Tryptophan, D- and L-Prolin as control. IL-5, IFN-gamma, IL-12, and IL-10, were quantified by a multiplex assay (Milliplex Human Cytokine Immunoassay, Millipore GMbH Schalbach, Germany) as described by the manufacturer.

Bioassay-Guided Fractionation of Probiotic Supernatants and Structural Elucidation of D-Tryptophan. Each Fractionation Step was Controlled and Driven by the Results from the Bioassays.

Fractionation according to polarity. Bioactive cell-free supernatants were first fractionated using stepwise gradient elution in solid phase extraction cartridges. 6 mL of bacteria free supernatants from *Lactobacillus casei* W56 and *Lactobacillus rhamnosus* GG and CDM1 medium (control) were applied into SPE-C$_{18}$ cartridges (1 g, Mega Bond Elut, Varian, Agilent Technologies, Santa Clara, USA). Elution was done in 10 steps using 2 mL of methanol/water solutions from 0% to 100% MeOH. Each resulting eluate was divided in two equal volumes and dried in a SpeedVac (SpeedVac Concentrator, Savant SPD 121P, Thermo Fisher Scientific, Waltham, USA) for further bioassay experiments and chemical analyses. MeOH/water extracts that showed bioactivity were resolved in 500 μL of 10% MeOH/water solution and further subjected to a second fractionation using a pentafluorophenyl chromatographic column (Kinetex PFP 1.7 μm, 2.1×150 mm, Phenomenex, Torrance, USA) in order to have a complementary selectivity to C$_{18}$ phase. A nonlinear gradient in 10 min from 5 to 25% B, 14 min to 100% B at 40° C. with 0.180 mL/min flow rate (Mobile phase A: 10% MeOH/H$_2$O; B: 100% MeOH) was applied.

To this end, an Ultra Performance Liquid Chromatography system (UPLC-PDA, Waters, UK) was coupled to an automatic fraction collector (TriVersa NanoMate, Advion BioSciences, Ithaca, USA) to originate new sub-fractions, which were retested in our bioassays. UPLC and collection methods were defined for the bioactive 20% MeOH/water extract according to its chromatogram at λ=200 nm in an attempt to collect single peaks or at least, reduce the complexity present in each collected sub-fraction. To obtain a large volume of each sub-fraction, the separation and collection process was repeated 15 times. The results from the bioassays drove the chemical characterization of the newly obtained bioactive sub-fractions.

Structural elucidation of the bioactive compound present in 20% MeOH extracts. The bioactive sub-fractions and their nearest neighbors collected from the second step fractionation in PFP columns were reevaluated via UPLC (Acquity, Waters, Elstree, UK) coupled to high resolution TOF Mass Spectrometer (maXis URH-TOF, Bruker Daltonics, Bremen, Germany) to identify a candidate compound by comparing peak retention time and m/z values between chromatograms. Here, reversed phase chromatography (BEH-C$_{18}$ 1.7 μm, 2.1×150 mm, Waters) and gradient elution from 0 to 100% B in 8 min at 40° C. (A: 10% MeOH/0.1% formic acid/water; B: 0.1% formic acid/MeOH; flow rate: 0.4 mL/min) was used. Total Ion Chromatograms were obtained in electrospray ionization (ESI) positive mode. The candidate compound was isolated by repeated chromatographic runs followed by peak collection until 1 ml of volume was obtained to purify the bioactive sub-fraction for further molecular formula assignment by high resolution FT-ICR-MS in positive and negative ESI mode (APEX-Qe 12 Tesla, Bruker Daltonics, Bremen, Germany) and for structural elucidation by proton NMR (Ultra-Shield Plus 800 MHz, Bruker Biospin, Billerica, USA).

Chiral separation of amino acid enantiomers in fractionated supernatants. After chemical characterization of the bioactive sub-fraction, it was important to know whether both isomers of Tryptophan were present in the solution. Therefore, a derivation technique using o-phthaldialdehyde (OPA) and N-isobutyryl-L-cysteine (IBLC) (Sigma-Aldrich, St. Louis, USA) according to a previously described method (Brückner et al., 1995, Journal of Chromatography, vol. 711, 1(201-215)). Standard solutions containing D- and L-Tryptophan and our bioactive sub-fraction were then analyzed by reversed phase chromatography using a small diameter UPLC column (BEH-$C_{18}$ 1.7 µm, 1.0×150 mm, Waters, Elstree, UK) with isocratic elution at 45% B for 3 min at 60° C. (A: 20 mM sodium acetate; B: 7% acetonitrile in MeOH; flow rate: 0.1 mL/min) coupled to a fluorescence detector ($\lambda$=300 nm for the excitation; $\lambda$=445 nm for the emission).

Enantiomeric separation of D-Tryptophan in murine sera. The investigator (C.M.) was blinded to the murine intervention groups. Due to the abundance of interfering proteins a protein precipitation was done. For this purpose the sera were thawed on ice and 20 µL of each sample were vigorously shaken with 80 µL 4° C. methanol (Chromasolve, Fluka, St. Louis, USA) and centrifuged (15,000×g at 4° C. for 15 min). The supernatants were taken, evaporated and resolved in water before injection. The derivation was performed as described for bacterial supernatants with some modifications as recently published (Müller et al., J Chromatogr A. 2014 Jan. 10; 1324:109-14). For quantification human serum was spiked with different concentrations (0.005-0.15 µg/mL) of D-Tryptophan and randomly analyzed. The enantiomeric ratio (peak area D-Tryptophan/peak area L-Tryptophan) was calculated, and was observed to follow a linear regression (y=0.0406x+0.0102, $R^2$>0.98).

Induction of allergic airway inflammation. Female 6-8 week old Balb/c mice (Charles River Laboratories, Wilmington, USA) were sensitized i.p. using 10 µg of ovalbumin (grade VI; Sigma Aldrich, St. Louis, USA) or PBS (controls) in alum (Pierce Chemical Co, Rockfort, USA) at day 0, 7 and 14 and challenged intranasally under isoflurane narcosis with 10 µg of ovalbumin in 20 µl PBS or PBS only (controls).

Lung function. Animals were anesthetized i.p. with ketamine (140 mg/kg) and xylazine (7 mg/kg), tracheostomized, intubated (18G tube), placed on a warming plate and ventilated with a tidal volume of 10 mL/kg at a frequency of 150 breaths/minute and a positive end-expiratory pressure of 2 cm $H_2O$ on a Buxco R/C system (Buxco Reseach Systems, Wilmington, USA). To assess airway hyperreactivity, the mice were challenged with metacholine in physiological saline generated with an in-line nebulizer and administered directly with increasing concentrations (0, 12.5, 25, 50 mg/mL) by the ventilator for 20 seconds. Resistance (R) and Compliance (C) were measured continuously for 2 min and the average was calculated and plotted against concentration.

Gene expression analysis in murine fetal lungs. Fetal lungs were collected from animals delivered via cesarean section at embryonic day 18.5 (Balb/c). Total RNA was isolated employing the miRNeasy Mini (Qiagen, Venlo, Netherlands) including digestion of remaining genomic DNA. The Agilent 2100 Bioanalyzer (Agilent Technologies, Santa Clara, USA) was used to assess RNA quality and only high quality RNA (RIN≥8.7) was used for microarray analysis. For mRNA profiling, 30 ng total RNA was amplified using the Ovation PicoSL WTA System V2 in combination with the Encore Biotin Module (Nugen, San Carlos, USA). Amplified cDNA was hybridized on an Affymetrix Mouse Gene ST 2.1 array plate. Staining and scanning was done according to the Affymetrix expression protocol including minor modifications as suggested in the Encore® Biotin protocol (NuGen, San Carlos, USA).

Bacterial 16S rRNA gene amplification and diversity analysis. Diversity analysis of 16S rRNA genes was performed by amplicon sequencing. In the first PCR reaction, bacterial genomic DNA was subjected to 16S rRNA gene amplifications using the primer S-D-Bact-0785-a-S-18 [5'-GGMTTAGATACCCBDGTA-3'] (SEQ ID NO: 1) and S-*-Univ-1100-a-A-15 [5'-GGGTYKCGCTCGTTR-3'] (SEQ ID NO: 2) as already mentioned. The reaction mixture of 25 µL in total was composed of 5 ng×µL-1 template DNA, 10 µM of each primer, 10 mM dNTPs (Fermentas, Vilnius, Lithuania), 5% of dimethyl sulfoxide (Sigma-Aldrich, St. Louis, USA), 5 U×µL-1 of FastStart High Fidelity Polymerase (Roche Diagnostics, Mannheim, Germany), 10× FastStart Buffer, and nuclease-free water (Life Technologies, Carlsbad, Calif., USA). The PCR started with an initialization at 95° C. for 5 min, followed by 28 cycles of denaturation at 94° C. for 45 sec, annealing at 44° C. for 45 sec, and elongation at 72° C. for 45 sec. A final elongation step at 72° C. for 5 min completed the PCR reaction. To minimize contamination with primer dimers, generated fragments were cut out of the gel after standard agarose gel electrophoresis and purified with the NucleoSpin Gel and PCR Clean-up Kit (Macherey-Nagel, Düren, Germany).

During the second PCR, Illumina sequencing adapters as well as dual indices were attached to the purified amplicons using the Nextera XT Index Kit (Illumina, San Diego, Calif., USA). The reaction volume was 50 µL in total and contained 5 µL of genomic DNA, 5 µL of each Nextera XT Index Primer, 25 µl 2× KAPA HiFi HotStart ReadyMix (Kapa Biosystems, Wilmington, Mass., USA), and 10 µL of nuclease-free water (Life Technologies, Carlsbad, Calif., USA). The PCR reaction was performed according to the following thermal profile: 95° C. for 3 min, followed by 8 cycles of 95° C. for 30 sec, 55° C. for 30 sec, 72° C. for 30 sec, and finalized by 72° C. for 5 min. The PCR products were cleaned up with the Agencourt AMPure XP system (Beckman Coulter, Brea, Calif., USA), DNA was quantified and the DNA quality was controlled using the 2100 Bioanalyzer Instrument (Agilent Technologies, Santa Clara, Calif., USA), and sequenced with the MiSeq instrument (Illumina, San Diego, Calif., USA).

Gene expression analysis. Total RNA was isolated from homogenized lung tissue or cell culture using the miRNeasy Micro Kit according to manufacturer's instructions (Qiagen, Venlo, Netherlands). Concentrations were determined using a NanoDrop® ND-1000 (NanoDrop Technologies, Erlangen, Germany) spectrophotometer. mRNA was transcribed to cDNA with the QuantiTect Rev. Transcription kit (Qiagen, Venlo, Netherlands) and PCR for specific genes was performed on a LightCycler 480 platform with Light Cycler 480 SYBR Green I Mastermix (Roche, Mannheim, Germany). Detailed qPCR primer sequences are listed in table 4.

Bacterial strains. Bifidobacteriae, Lactobacilli, Lactococci, *E. Coli* Nissle 1917, *Enterococcus faecium*, and *Streptococcus thermophilus* were obtained from different providers (Table 3) All strains were grown until stationary phase and a minimum cell number of $10^8$ CFU/ml. Cell free supernatants were obtained by centrifugation (6000 rpm; 5 min; 20° C.) followed by filtration through 0.22 µm pore size surface-modified polyethersulfone membrane (Millipore, Darmstadt, Germany). No bacterial growth was observed when aliquots from supernatants were cultured in bacterial growth medium. Otherwise, supernatants were stored immediately after collection in aliquots at −80° C. until further use.

Bioassays for screening for immune modulatory activity in probiotic supernatants. Two biological assays based on down-modulation of costimulatory molecules on human DCs, and of CCL17-secretion by a human Hodgkin lymphoma T cell line (KM-H2) were set up. Human immature DCs were matured with 0.1 μg/mL lipopolysaccharide (LPS) from *E. coli* (Sigma-Aldrich, St. Louis, USA) in the presence or absence of 200 μL bacteria free supernatants for 24 h followed by flow cytometric analysis of costimulatory molecules.

Similarly, 200 μL supernatants were added to 3-5×10$^6$ KM-H2 cells for 24 h. Supernatants were collected from KM-H2 by centrifugation and stored at −80° C. until quantification of CCL17. To control for the dilution of KM-H2 culture media with different volumes of bacterial supernatants, the corresponding amount of blank MRS medium was added. Blank bacterial growth medium and supernatants from Lactobacillus rhamnosus DSM 20021, which has no probiotic activity, were used as negative controls in both screening assays.

Animals and oral supplementation with D-tryptophan. All animal experiments were conducted under the Federal Guidelines for the Use and Care of Laboratory Animals (Az 55.2-1-54-2532-137-13) and was approved by the Government of the District of Upper Bavaria and Schleswig-Holstein (V244-13313/2016 (7-1/10). Female Balb/c mice from 6-8 weeks old were obtained from Charles River (Sulzfeld, Germany) and housed in individually ventilated cages with two mice each in specific pathogen free conditions. A standard extruded pellet diet and sterile filtered drinking water were provided ad libitum. For quantification of D-tryptophan in mouse sera, D-tryptophan (Sigma-Aldrich, St. Louis, USA) was dissolved in the drinking water at concentrations of 1.8 mg/dL or 18 mg/dl (approximately 0.09 and 0.9 mg/day per mouse). Control animals received pure water (n=8 per group). No changes in behavior or body weight were noted in the supplemented animals compared to controls. Animals were sacrificed after 14 days and sera were immediately stored at −80° C. until analysis.

For testing prevention of AAI, mice received 50 mM D-tryptophan starting at least three days before the first sensitization until sacrificing on day 25. For microbiome analyses, the caecum was cut off and immediately stored at −80° C. until further processing.

Statistical Analyses: Bioassays and Animal Experiments

Results of bioassays and animal experiments are given as means with standard deviation. Student's t test with Dunn's Multiple Comparison Test or Two-way ANOVA with Bonferroni post test were used where appropriate. Tests applied are given in the respective figure legends. P values<0.05 were considered significant. (GraphPad Prism Software version 5.0, Inc. La Jolla, Calif. 92037 USA).

Microbial Diversity. Bacterial diversity was assessed by molecular barcoding of 16S rRNA genes in caecum samples of six animals per group. To this end, DNA was directly extracted from the caecum using a kit based protocol (PowerSoil DNA Isolation Kit, MO BIO Laboratories, Carlsbad, Calif., USA). 315 bp fragments were amplified within the variable region V5 and V6 of the 16S rRNA gene using S-D-Bact-0785-a-S-18[5'-GGMTTAGATACCCBDGTA-3'] (SEQ ID NO: 1) and S-*-Univ-1100-a-A-15 [5'-GGGTYKCGCTCGTTR-3'] (SEQ ID NO: 2) as primers (Klindworth et al., Nucleic Acids Res. 2013 Jan. 7; 41(1):e1). Sequencing of amplicons was performed on the Illumina MiSeq platform (Illumina, San Diego, Calif., USA) using paired end technology (see section "Bacterial 16S rRNA gene amplification and diversity analysis" herein). Sequences are deposited in NCBI accession number PRJNA304109.

Reads were analyzed with the software package QIIME. Operational taxonomic units (OTUs) were picked within the 13_8 version of the Greengenes reference database (McDonald et al., ISME J. 2012 March; 6(3):610-8) at a similarity level of 95% sequence identity. Sequences were subsampled to 15000 reads per sample, which reflects the number of reads obtained in the sample with the lowest number of reads after quality control. This number was still sufficient to reach a plateau when collectors' curves were calculated on the basis of OTU$_{95}$. The taxonomy assignment was done using the RDP classifier 2.2 (Wang et al., Appl Environ Microbiol. 2007 August; 73(16):5261-7). Principal coordinate analysis (PCoA) was generated on the unweighted UniFrac distance matrix using the ape-package within the R software environment and statistical significance was determined with the Student's t test. Alpha-diversity of each sample was measured using the Chao1 metric (Chao, Scand J Stat. 1984; 11(4):265-70) and compared between treatments by nonparametric two-sample t test (i.e., using Monte Carlo permutations for significance testing). Beta-diversity was calculated using the phylogenetic method UniFrac (Lozupone et al., Appl Environ Microbiol. 2005 December; 71(12): 8228-35). The nonparametric analysis of similarity (ANOSIM) was performed to examine the beta-diversity distance matrix for significant differences between groups of samples; differences in OTU abundance between groups were tested for significance by nonparametric ANOVA.

I. Identification and Characterization of a Bioactive Probiotic Substance

Example 2

Screening of Crude Probiotic Supernatants for Downregulation of CCL17

To develop a high-throughput screening system for the detection of Th2-downregulatory activity in supernatants from probiotic bacteria, use was made of the high constitutive secretion of the Th2-associated CCL17 by the human Hodgkin Lymphoma T cell line KM-H2.

To identify the threshold for downregulation of CCL17, KM-H2 cells were incubated with increasing volumes of supernatants from *Lactobacilus rhamnosus* GG (*L. rhamnosus* GG), *Bifidobacterium* BB-420 and *Lactobacillus casei* W56. Supernatants from all three probiotic strains led to a significant dose- and time dependent reduction of CCL17 concentrations to ~30% relative to supernatant from the non-probiotic *Lactobacillus rhamnosus* DSM-20021 (FIG. 1A). The minimum volume (200 μl) leading to that reduction was used in all subsequent experiments.

As the numerous ingredients of the bacterial culture medium interfered with the detection of specific signals in mass spectrometry, the bacteria were cultivated in less complex medium, chemically defined medium (CDM1). The potency of supernatants from probiotic strains cultivated in CDM1 versus standard medium to lower CCL17 concentrations was comparable (FIG. 8A, B). Subsequent testing of supernatants from 37 probiotic strains revealed that 7 of 21 *Lactobacillus* sp. strains, 5 of 10 *Bifidobacterium* sp. strains, and 1 of 3 *Lactococcus* sp. strains lowered CCL17 secretion without affecting cell viability FIG. 9). In contrast, none of the *Streptococcus thermophilus, Enterococcus faecium* or *E. coli* Nissle 1917 strains influenced CCL17 levels (FIG. 2; Table 3).

Example 3

Verification of Results from CCL17-Based Screening Assays

To confirm the observed immune modulatory activity, the efficacy of the probiotic supernatants to lower the expression of co-stimulatory molecules on human monocyte derived dendritic cells (DC) was evaluated. Upon recognition of antigen, naïve DCs undergo a complex maturation process. While fully activated DCs induce adaptive immune responses, incomplete activation leads to tolerance. Therefore, it was screened for reduced expression of co-stimulatory molecules in the presence of probiotic supernatants. All 13 supernatants that had already been pre-identified as "immune modulatory" in the CCL17-based screen also significantly decreased the percentages of LPS-induced CD83, CD80, CD86 and CD40 expressing mature DCs, whereas the remaining supernatants were inactive on DCs. None of the supernatants affected the viability of DC FIG. 9. Thus, both bioassays gave 100% concordant results. (FIG. 1B). For a complete overview of the bioactivity of all strains see table 3.

Example 4

Fractionation of Selected Probiotic Supernatants Yields Three Bioactive Fractions of Different Polarity

*L. rhamnosus* GG has been most frequently used in clinical studies. Therefore, supernatants from *L. rhamnosus* GG and further of *L. casei* W56 for further enrichment and stepwise chemical characterization of the putative metabolite were selected. During this procedure, each sub-fraction was retested for bioactivity in both the KMH2 and DC bioassays.

Bacterial supernatants were subjected to semi-preparative chromatography yielding 11 MeOH/H$_2$O extracts. The highest immune modulatory activity was found in the 20% fraction along with slightly lower activities in the 40% and 50% MeOH fractions (FIG. 3). Therefore, this fraction was chosen for further purification.

Example 5

Isolation and Identification of the Bioactive Substance in 20% MeOH/H2O Etracts

Figure 11A:
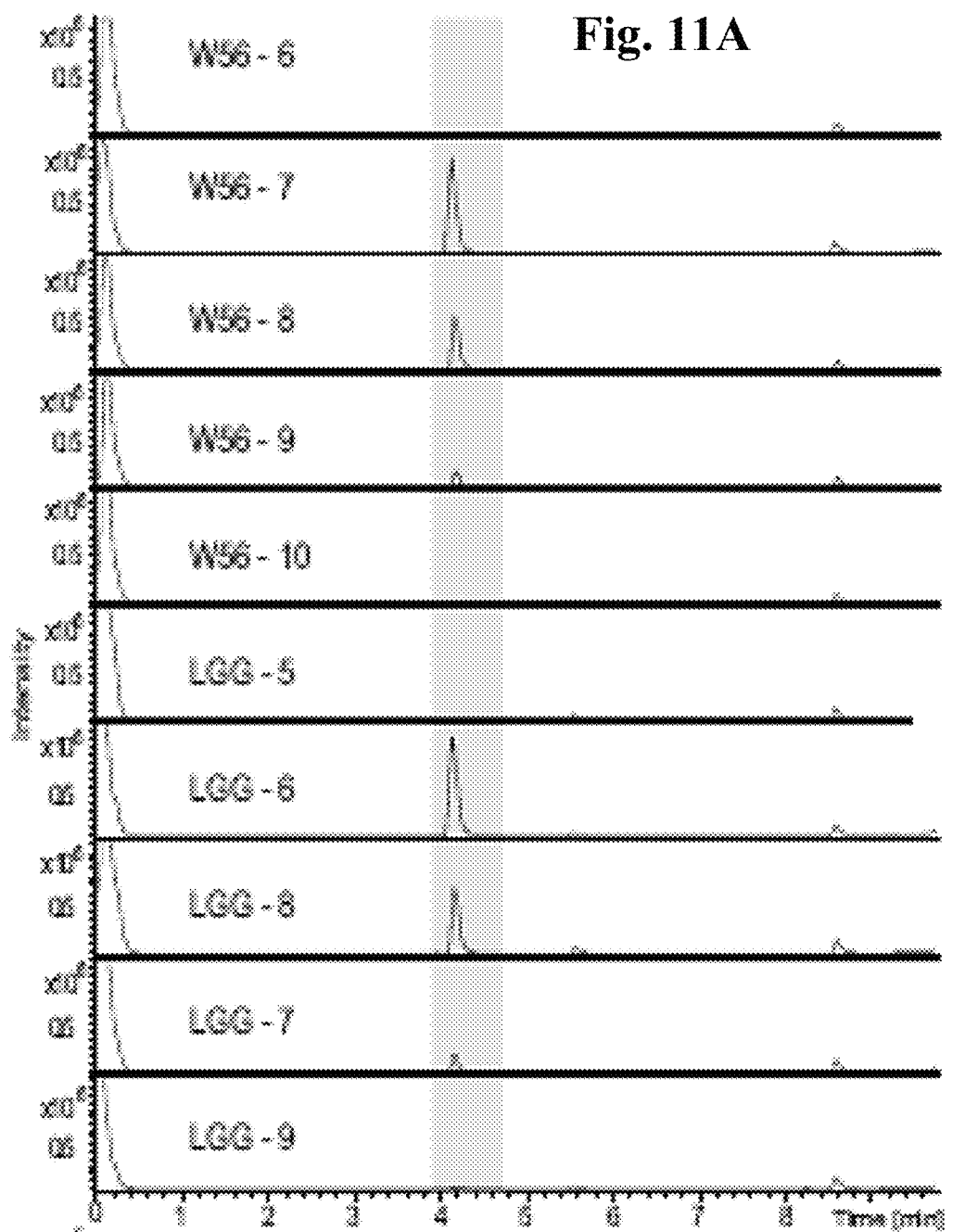
FIG. 11A is a graph showing chromatogram peaks from UPLC-URH-TOF MS analyses of *L. casei* W56 and LGG bioactive sub-fractions and their nearest neighbors.
Figure 11B:
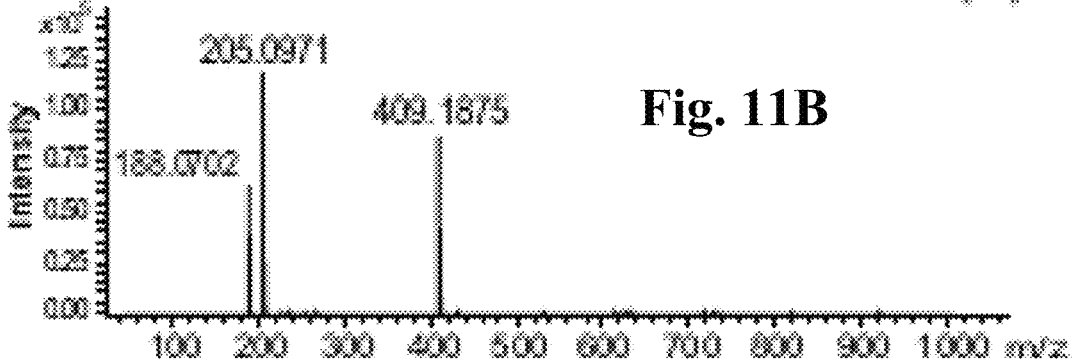
FIG. 11B is a graph showing mass spectra peaks corresponding to the chromatographic time range of 4.1-4.3 min.

Chromatographic sub-fractionation of the 20% MeOH/H$_2$O fraction yielded ten sub-fractions, three of which showed activity in the bioassays (FIG. 10A, B). These sub-fractions and their closest neighbors were re-evaluated via reversed phase UPLC-High Resolution TOF MS generate Total Ion Chromatograms. By identifying similarities in the chromatograms, a substance was identified that, according to peak retention time and molecular mass information, was only present in the bioactive sub-fractions, being highest in sub-fraction 7 from *L. casei* W56 and sub-fraction 6 from *L. rhamnosus* GG (FIG. 11A). The extracted mass spectrum strongly suggested that this substance was composed of the tryptophan ions $[2M+H]^+$, $[M+H]^+$ and its fragment $[M+H-NH_3]^+$ (FIG. 11B).

Figure 11C:
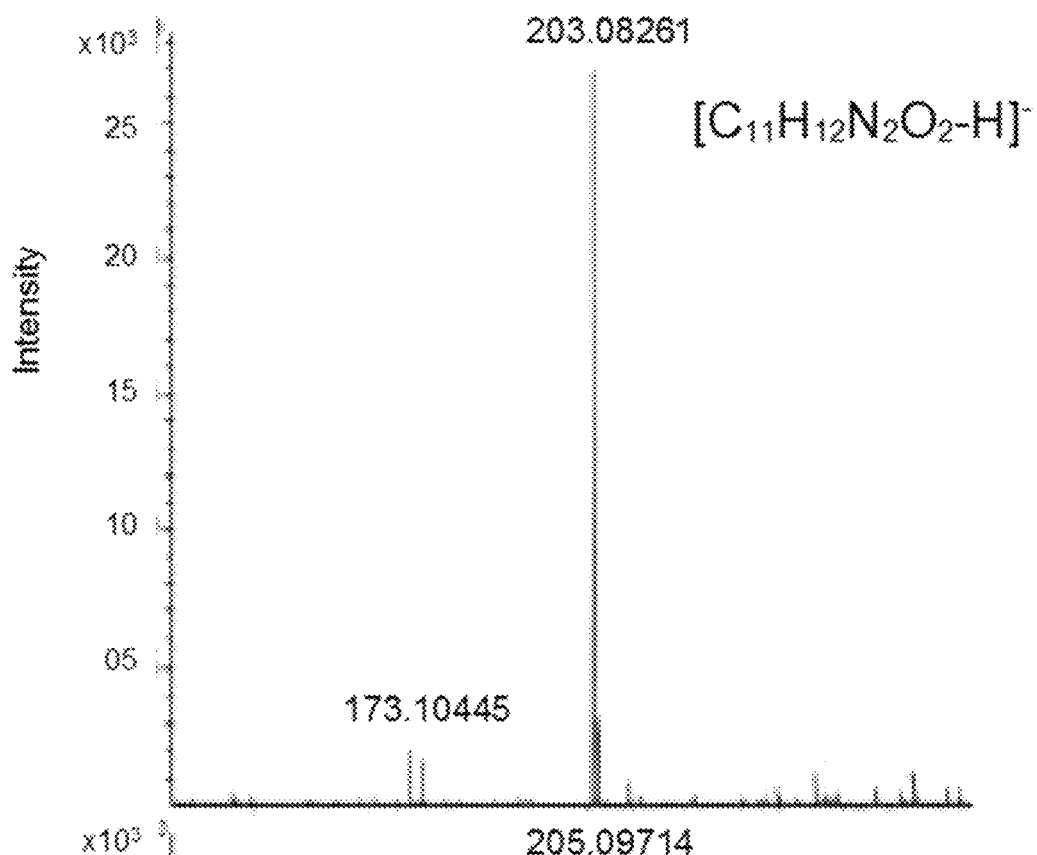
FIGS. 11C and 11D are graphs showing FT-ICR-MS spectra peaks of the purified bioactive sub-fraction 7 of LGG in ESI negative mode and ESI positive mode respectively.
Figure 11D:
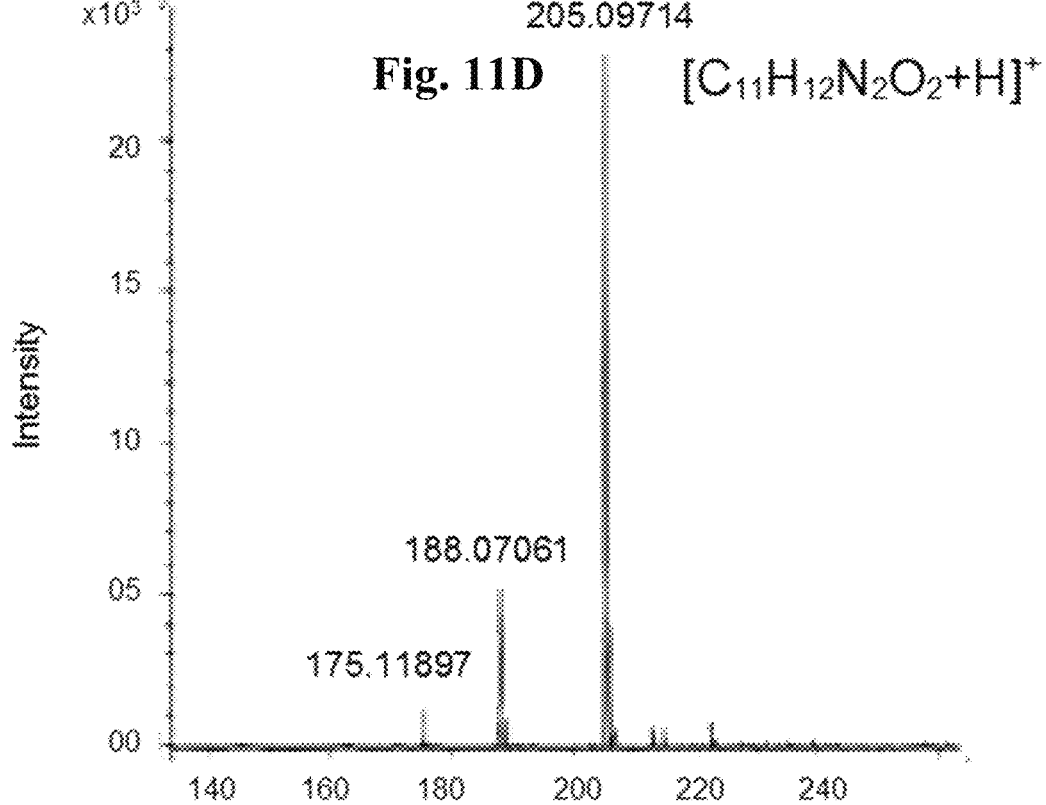

After careful enrichment of the bioactive substance by repeated chromatography runs, the isolated candidate substance of both strains showed bioactivity in both screening assays. High resolution mass spectrometry analyses by FT-ICR-MS confirmed $C_{11}H_{12}N_2O_2$ as the molecular formula of these ions (FIG. 11C, D). Further analyses by proton NMR provided detailed information on the functional group distribution and molecular structure: The doublets and triplets ($\delta 7.8$-7.0) showed the occurrence of an idole ring. Resonance signals at the region of $\delta 3.9$-3.8 and $\delta 3.2$-3.1 could also be assigned to β-CH and α-CH protons, respectively (FIG. 12). Thus, there was a close agreement between standard tryptophan and our bioactive sub-fraction.

Since L-tryptophan is a standard component of the bacterial growth medium, it was hypothesized that the bioactivity is related to the D-form of this amino acid. Indeed, enantiomeric separation of the purified sub-fraction confirmed the presence of D- and L-tryptophan (FIG. 13A), while the corresponding sub-fraction of blank medium contained solely the L-form (FIG. 13B).

Example 6

The Immune Modulatory Activity in Probiotic Supernatants is Restricted to the D-form of Tryptophan To verify if the bioactivity was indeed restricted to the D-isomer of tryptophan, different concentrations of synthetic L- and D-tryptophan in the CCL17 bioassay were tested. Only D-tryptophan showed a dose dependent immune activity (FIG. 4). Moreover, none of twelve other polar and non-polar neutral D-amino acids tested showed any bioactivity (Table 1).

Example 7

Bacterial Supernatants and D-Tryptophan Modulate Cytokine Profiles of Enriched Human DC To obtain a first insight into mechanisms underlying this bioactivity, the cytokines secreted by highly enriched DCs (FIG. 9D) were quantified after treatment with the bacterial supernatants or synthetic D-tryptophan. All probiotic supernatants and D-tryptophan strongly induced IL-10 and lowered LPS-induced IFN-g, IL-12 and IL-5 in these cultures. In contrast, cytokine patterns were unaffected by the control supernatants, and amino acids (Table 2). Overall this resulted in increased IL-10/IL-12 ratios and—with the exception of BB-46—in decreased IL-5/IFN-g ratios.

II. Preclinical Effects of Oral D-Tryptophan Supplementation

Example 8

D-Tryptophan Influences Allergic Airway Inflammation and Th2 Immune Responses

If it is to be used as an oral intervention in allergic diseases, D-tryptophan needs to be absorbed from the gut. Oral supplementation of mice with 0.9 mg/day D-tryptophan increased D-tryptophan serum levels significantly (FIG. 5A) indicating enteric uptake and systemic distribution. Pretreatment of mice with D-tryptophan for 3 days and throughout experimental "asthma" induction lowered total BALF cells, which was mainly caused by a reduction of eosinophils (FIG. 5B, C). Furthermore, the supplementation improved airway hyperreactivity to methacholine (FIG. 5D). As this suggested an involvement of Th2 responses, lung T cells were analyzed: D-tryptophan reduced II-4 producing T cells and II-4 levels in BALF (trend, FIG. 5E, F and 14) but not Ifn-g-producing Th1 cells. Furthermore, D-Trp treatment significantly increased Helios+ Treg while total Foxp3+ cells remained unchanged (FIG. 5G).

To further substantiate these in vivo findings T cell differentiation assays in vitro were performed. In line with the in vivo observations, D-Trp reduced Th2 cell differentiation, whereas Th1 differentiation remained unaffected (FIG. 6A,B). Consequently, II-4, Gata3 expression and II-13 secretion was reduced, whereas Ifng expression remained unaffected. Treg cells however, showed increased Foxp3 expression on mRNA and protein level (FIG. 6C).

Example 9

D-Tryptophan Induces Gut Tregs and Increases Intestinal Microbial Diversity in Allergic Airway Inflammation In addition to the observed pulmonary immune response, the frequency of Foxp3+ T cells was locally increased in the colon of supplemented AAI mice compared to non-supplemented AAI mice (FIG. 7A). Altered gut immunity might be driven directly by D-tryptophan and/or indirectly via altered gut microbiota.

A diversity analysis of bacteria by 16S rRNA based barcoding demonstrated a strongly reduced community richness and diversity at the level of $OTU_{95}$ in AAI mice (FIG. 7B). Supplementation with D-tryptophan increased the in bacterial diversity of AAI mice, resulting in comparable alpha-diversity patterns compared to healthy animals. Although the original diversity was not completely restored after D-Trp application, its impact on microbial community composition was significant (FIG. 16A).

Independent of the health status of the animals D-tryptophan supplementation all samples were dominated by the phyla Bacteroidetes and Firm icutes (19.4-27.7% and 65.9-78.4% of the total sequences). As expected, the phylum Firmicutes mainly consisted of members of the order Clostridiales. Other phyla including Actinobacteria and Proteobacteria were also present but at significantly lower abundance. At the family level, Lachnospiraceae, Odoribacteraceae, Rikenellaceae, Ruminococcaceae, S24-7 and an unclassified bacterial family belonging to Clostridiales (FIG. 16B) dominated. The latter was mainly present in AAI mice, forming 58.6% of the total community. Lachnospiraceae, however, were less abundant in AAI animals (5.5%), compared to controls (13.7%), to D-tryptophan treated AAI mice (20.6%), or to D-tryptophan treated mice without AAI (27.5%). Odoribacteraceae were strongly affected by D-Tryptophan, as their relative abundance tripled in both groups of supplemented animals (3.9% vs ~1.1%). In contrast, Rikenellaceae showed a decreased abundance in the D-Trp groups (1.1-2.0%) compared to to the control groups (4.6-7.7%). Interestingly, Ruminococcaceae, which were strongly reduced in the control mice affected with AAI (3.7%), recovered by the application of D-Trp (8.9%): this was comparable to the abundance in control group of mice without AAI. Members of the S24-7 family were neither affected by AAI nor by the application of D-tryptophan. Overall, D-tryptophan supplementation increased intestinal bacterial diversity in AAI, D-tryptophan treated mice, such that the bacterial diversity pattern was more comparable to 'healthy' control mice (PBS/PBS). (FIG. 7B). Thus, these results suggested that D-tryptophan treatment reestablishes a "healthy" microbial community genotype in mice with AAI.

TABLE 1

Percentage of surface marker expressing mature DCs treated with synthetic D-amino acids*

|  | D-alanine | D-histidine | D-isoleucine | D-leucine | D-methionine | D-phenylalanine |
|---|---|---|---|---|---|---|
| CD83 | 97.7 ± 2.3 | 103.1 ± 0.3 | 100.5 ± 1.1 | 97.1 ± 2.4 | 102.4 ± 2.2 | 99.6 ± 2.0 |
| CD86 | 99.2 ± 2.1 | 102.5 ± 0.4 | 99.8 ± 1.2 | 101.9 ± 1.3 | 102.2 ± 2.5 | 99.2 ± 3.3 |
| CD80 | 98.3 ± 2.6 | 102.0 ± 0.9 | 98.2 ± 1.5 | 100.3 ± 1.6 | 100.4 ± 0.2 | 92.4 ± 3.5 |
| CD40 | 102.3 ± 3.4 | 101.4 ± 3.2 | 100.4 ± 2.4 | 100.4 ± 1.7 | 102.7 ± 0.6 | 100.4 ± 2.7 |
| HLA-DR | 98.1 ± 1.1 | 99.9 ± 0.9 | 100.1 ± 0.3 | 98.0 ± 10.0 | 98.9 ± 2.0 | 98.0 ± 3.2 |

|  | D-proline | D-serine | D-threonine | D-trytophan | D-tyrosin | D-valine |
|---|---|---|---|---|---|---|
| CD83 | 100.9 ± 0.4 | 100.8 ± 0.3 | 102.6 ± 0.5 | 7.6 ± 3.3 | 101.6 ± 0.6 | 102.1 ± 1.2 |
| CD86 | 101.2 ± 1.9 | 101.1 ± 2.8 | 102.1 ± 0.7 | 24.1 ± 2.7 | 102.2 ± 0.9 | 101.8 ± 0.9 |
| CD80 | 100.3 ± 0.1 | 100.1 ± 2.8 | 100.8 ± 0.4 | 12.1 ± 1.7 | 101.6 ± 0.4 | 99.6 ± 2.0 |
| CD40 | 99.2 ± 1.3 | 100.8 ± 1.1 | 100.6 ± 1.5 | 15.2 ± 6.5 | 100.4 ± 1.3 | 101.4 ± 2.4 |
| HLA-DR | 98.4 ± 2.6 | 98.6 ± 0.6 | 97.1 ± 3.9 | 88.9 ± 3.0 | 98.4 ± 2.4 | 100.0 ± 1.0 |

*DCs were stimulated with LPS (0.1 µg/ml) in the presence of the indicated D-amino acids (10 µM). Percentages of CD83, CD86, CD80 or CD40 expressing DCs were assessed.
Three independent experiments (mean percentages ± SD, relative to LPS-induced expression).

TABLE 2

Cytokine regulation by probiotic supernatants or D/L-tryptophan in human LPS treated DCs*

|  | IL-10 [pg/ml] | | IL-5 [pg/ml] | | IFN-g [pg/ml] | | IL-12 [pg/ml] | | Ratios | |
|---|---|---|---|---|---|---|---|---|---|---|
|  | | | | | | | | | IL-10/IL-12 | IL-5/IFN-g |
|  | — | LPS | — | LPS | — | LPS | — | LPS | — | LPS | — | LPS |
| Medium | 3.20 | 2.90 | 14.70 | 68.30 | 112.50 | 2238.80 | 102.10 | 2092.80 | 0.031 | 0.001 | 0.131 | 0.031 |
| DSM-20021 | 6.80 | 4.80 | 33.60 | 55.90 | 330.00 | 2520.50 | 447.80 | 2217.30 | 0.015 | 0.002 | 0.102 | 0.022 |

TABLE 2-continued

Cytokine regulation by probiotic supernatants or D/L-tryptophan in human LPS treated DCs*

| | IL-10 [pg/ml] | | IL-5 [pg/ml] | | IFN-g [pg/ml] | | IL-12 [pg/ml] | | Ratios IL-10/IL-12 | | IL-5/IFN-g | |
|---|---|---|---|---|---|---|---|---|---|---|---|---|
| | — | LPS | — | LPS | — | LPS | — | LPS | — | LPS | — | LPS |
| LGG | 432.90 | 787.90 | 9.10 | 5.40 | 372.70 | 105.70 | 79.20 | 106.90 | 5.466 | 7.370 | 0.024 | 0.051 |
| LA-2 | 107.30 | 591.70 | 8.00 | 10.30 | 111.60 | 437.70 | 89.30 | 238.00 | 1.202 | 2.486 | 0.072 | 0.024 |
| LA-5 | 81.30 | 305.70 | 7.60 | 8.00 | 113.30 | 531.80 | 87.50 | 331.10 | 0.929 | 0.923 | 0.067 | 0.015 |
| LC-01 | 452.40 | 924.50 | 7.90 | 2.40 | 109.30 | 211.30 | 76.90 | 67.80 | 5.883 | 13.636 | 0.072 | 0.011 |
| BB-12 | 234.90 | 735.70 | 11.00 | 10.90 | 75.40 | 437.00 | 91.50 | 228.20 | 2.567 | 3.224 | 0.146 | 0.025 |
| BB-46 | 813.50 | 1230.70 | 14.00 | 13.60 | 13.50 | 637.90 | 95.10 | 202.30 | 8.554 | 6.084 | 1.037 | 0.021 |
| BB-420 | 450.40 | 915.40 | 8.80 | 8.40 | 81.50 | 783.70 | 102.50 | 356.90 | 4.394 | 2.565 | 0.108 | 0.011 |
| L-Trp | 5.70 | 4.90 | 12.00 | 61.40 | 45.00 | 2031.50 | 88.30 | 1993.00 | 0.065 | 0.002 | 0.267 | 0.030 |
| D-Trp | 56.90 | 202.50 | 10.30 | 20.60 | 21.90 | 1129.50 | 82.50 | 871.90 | 0.690 | 0.232 | 0.470 | 0.018 |
| L-Pro | ** | 6.00 | 14.80 | 57.70 | 88.90 | 2133.90 | 99.80 | 1938.00 | ** | 0.003 | 0.166 | 0.027 |
| D-Pro | 5.90 | 4.00 | 15.80 | 69.10 | 92.60 | 2295.40 | 90.60 | 1911.90 | 0.065 | 0.002 | 0.171 | 0.030 |

*DCs were stimulated in the presence or absence of LPS (0.1 µg/ml) with supernatants from 200 µl bacterial cell free supernatants or tryptophan enantiomers (10 µM) for 14 h. Non-probiotic DSM-20021 and blank medium (CDM1) were used as negative control. D/L-prolin and L-tryptophan were used as controls for D-tryptophan.
**below detection limit

TABLE 3

Bacterial strains used in this study

| | | Bioactivity on[1] | |
|---|---|---|---|
| Bacterial strain | Provider | KM-H2 | DC |
| Lactobacillus rhamnosus DSM-20021 | Leibniz Institute DSMZ | − | − |
| Lactobacillus rhamnosus GG | Valio Ltd, Helsinki, Finland | + | + |
| Lactobacillus acidophilus W22 | Winclove Bioindustries BV | + | + |
| Lactobacillus acidophilus W37 | Winclove Bioindustries BV | − | − |
| Lactobacillus acidophilus W50 | Winclove Bioindustries BV | − | − |
| Lactobacillus acidophilus W74 | Winclove Bioindustries BV | − | − |
| Lactobacillus acidophilus DSM-20079 | Leibniz Institute DSMZ | − | − |
| Lactobacillus acidophilus LA-2 | Chr. Hansen | + | + |
| Lactobacillus acidophilus LA-5 | Chr. Hansen | + | + |
| Lactobacillus casei W56 | Winclove Bioindustries BV | + | + |
| Lactobacillus casei W79 | Winclove Bioindustries BV | + | + |
| Lactobacillus paracasei DSM-20312 | Leibniz Institute DSMZ | − | − |
| Lactobacillus paracasei subsp. paracasei LC-01 | Chr. Hansen | + | + |
| Lactobacillus gasseri W44 | Winclove Bioindustries BV | − | − |
| Lactobacillus gasseri DSM-20077 | Leibniz Institute DSMZ | − | − |
| Lactobacillus helveticus W60 | Winclove Bioindustries BV | − | − |
| Lactobacillus plantarum W21 | Winclove Bioindustries BV | − | − |
| Lactobacillus plantarum W62 | Winclove Bioindustries BV | − | − |
| Lactobacillus plantarum DSM-20174 | Leibniz Institute DSMZ | − | − |
| Lactobacillus rhamnosus W102 | Winclove Bioindustries BV | − | − |
| Lactobacillus salivarius W24 | Winclove Bioindustries BV | − | − |
| Lactobacillus salivarius W57 | Winclove Bioindustries BV | − | − |
| Bifidobacterium animalis subsp. lactis BB-12 | Chr. Hansen, Horsholm, Denmark | + | + |
| Bifidobacterium breve W25 | Winclove Bioindustries BV, Amsterdam, Netherlands | − | − |
| Bifidobacterium breve DSM-20091 | Leibniz Institute DSMZ-German Collection of Microorganisms and Cell Cultures, Braunschweig, Germany | − | − |
| Bifidobacterium bifidum DSM-20456 | Leibniz Institute DSMZ | − | − |
| Bifidobacterium lactis BB-420 | Danisco, Niebüll, Germany | + | + |
| Bifidobacterium lactis W51 | Winclove Bioindustries BV | − | − |
| Bifidobacterium lactis W52 | Winclove Bioindustries BV | + | + |
| Bifidobacterium longum BB-46 | Chr. Hansen | + | + |
| Bifidobacterium longum W108 | Winclove Bioindustries BV | + | + |
| Bifidobacterium longum subsp. infantis DSM- 20088 | Leibniz Institute DSMZ | − | − |
| Enterococcus faecium W54 | Winclove Bioindustries BV | − | − |
| Lactococcus lactis W19 | Winclove Bioindustries BV | − | − |
| Lactococcus lactis W32 | Winclove Bioindustries BV | − | − |
| Lactococcus lactis W58 | Winclove Bioindustries BV | + | + |

TABLE 3-continued

Bacterial strains used in this study

| Bacterial strain | Provider | Bioactivity on[1] | |
|---|---|---|---|
| | | KM-H2 | DC |
| *Streptococcus thermophilus* W69 | Winclove Bioindustries BV | – | – |
| *Escherichia coli* Nissle 1917 | Ardeypharm GMbH, Herdecke, Germany | – | – |

[1]Ability of bacterial cell free supernatants to lower CCL17 secretion by KMH2 cells (left) and to reduce LPS-induced up-regulation of costimulatory molecules on human monocyte derived dendritic cells (DC, left)

TABLE 4 primer sequences used for qRT-PCR

| Name | fwd 5'->3' | rev 5'->3' |
|---|---|---|
| Gata 3 | CTTATCAAGCCCAAGCGAAG (SEQ ID NO: 3) | CATTAGCGTTCCTCCTCCAG (SEQ ID NO: 4) |
| IL4 | GGATGCGACAAAAATCACTTG (SEQ ID NO: 5) | TTGGAAGCCCTACAGACGAG (SEQ ID NO: 6) |
| IL13 | Mm_Il13_1_SG QuantiTect Primer Assay (Qiagen) | |
| Ifny | AGGTCAACAACCCACAGGTC (SEQ ID NO: 7) | GAATCAGCAGCGACTCCTTT (SEQ ID NO: 8) |
| Foxp3 | TCAAGTACCACAATATGCGACC (SEQ ID NO: 9) | TAGGCGAACATGCGAGTAAAC (SEQ ID NO: 10) |

What is claimed is:

1. A food composition or a pharmaceutical composition comprising D-tryptophan in an amount sufficient to increase the serum level of D-tryptophan in a human subject, such that the D-tryptophan peak area is increased at least 2-fold compared to the D-tryptophan peak area measured in the serum of a human subject which has not been supplemented with D-tryptophan,
  wherein the composition is configured to decrease constitutive CCL17 secretion of the cell line KM-H2 and to prevent upregulation of costimulatory molecules of LPS-stimulated human dendritic cells,
  wherein the composition is capable of altering the gut microbiota in a subject upon ingestion or administration,
  wherein D-tryptophan is present in the composition at a concentration by weight higher than any naturally-occuring material in the composition, and
  wherein the composition further comprises a buffering agent, an anti-oxidant, or a preservative, wherein the preservative is selected from the group consisting of Na-benzoate, a paraben, and benzalkonium chloride (BKC).

2. The food composition or pharmaceutical composition of claim 1 which is a pharmaceutical composition comprising a pharmaceutical excipient.

3. The food composition or pharmaceutical composition of claim 1, which is a food composition.

4. The food composition of claim 3, comprising D-tryptophan in a concentration of 0.1% to 100% by weight of the food composition.

5. The food composition of claim 3, wherein the food composition is selected from the group consisting of juices, refreshing drinks, drinking water, soups, teas, milk, beverages, dairy products, fermented milks, ices, butter, cheese, processed milk, skim milk, meat products, ham, sausage, hamburger, fish meat cake products, egg products, seasoned egg rolls, egg curd, confectioneries, cookie, jelly, snacks, chewing gum, breads, noodles, pickles, smoked products, dried fishes, seasonings, powder foods, sheet-like foods, bottled foods, canned foods, retort foods, capsule foods, tablet foods, fluid foods, food compositions for infants, modified milk for infants, protein-decomposed milk, specific nutritionally modified milk or baby foods and foods prepared for toddlers, powder milks dried and pulverized and baby foods, ice cream, fermented milk and jelly for infantile ingestion, pet feed, pet feeds for dogs, cats and rats, cattle feeds for cows and pigs, chicken feeds for chicken and turkeys, and fish cultivation feeds for porgy and yellowtail, feeds in which D-tryptophan is blended in a raw feed material selected from cereals, brans, oil-seed meals, animal-derived raw feed materials, other raw feed materials and purified products, cereals selected from mile, wheat, barley, oats, rye, brown rice, buckwheat, fox-tail millet, Chinese millet, Deccan grass, corn, and soybean, brans selected from rice bran, defatted rice bran, bran, lowest-grade flour, wheat germ, barley bran, screening pellet, corn bran, and corn germ, oil-seed meals selected from soybean meal, soybean powder, linseed meal, cottonseed meal, peanut meal, safflower meal, coconut meal, palm meal, sesame meal, sunflower meal, rapeseed meal, kapok seed meal and mustard meal, animal-derived raw feed materials selected from fish powders, import meal, whole meal, and coast meal, fish soluble, meat powder, meat and bone powder, blood powder, decomposed hair, bone powder, byproducts from butchery, feather meal, silkworm pupa, skim milk, casein, dry whey and krill, raw feed materials selected from plant stems and leaves selected from alfalfa, hey cube, alfalfa leaf meal, and locust leaf powder, byproducts from corn processing industries selected from corn gluten meal, corn gluten feed and corn steep liquor, starch, sugar, yeast, byproducts from fermentation industry selected from beer residue, malt root, liquor residue and soy sauce residue, and agricultural byproducts selected from citrus processed residue, soybean curd residue, coffee residue, and cocoa residue, cassava, horse bean, guar meal, seaweed, spirulina and chlorella, purified products selected from proteins selected from casein and albumin, amino acids, starch, cellulose, saccharides selected from sucrose and glucose, minerals and vitamins.

6. The food composition of claim 3 configured to provide a daily amount of D-tryptophan in the range of 0.1 mg to 100 g upon ingestion by a subject.

7. The food composition of claim 3 comprising solids components, the solids components consisting of the D-tryptophan and the buffering agent, the anti-oxidant, or the preservative, wherein the preservative is selected from the group consisting of Na-benzoate, the paraben, and benzalkonium chloride (BKC).

8. The food composition of claim 7 configured to provide a daily amount of D-tryptophan in the range of 0.1 mg to 100 g upon ingestion by a subject.

9. A method for the treatment, prevention or amelioration of a disease associated with $T_{reg}$ or $T_H2$ cells in a subject suffering from such a disease, the method comprising ingesting or administering to said subject a composition comprising D-tryptophan according to claim 1, wherein said ingesting or administering treats, prevents, or ameliorates the disease associated with $T_{reg}$ or $T_H2$ cells in the subject.

10. The method according to claim 9, wherein the disease is allergy.

11. The method according to claim 9, wherein the disease is an allergic airway disease.

12. The method according to claim 9, wherein the disease is asthma.

13. The method according to claim 9, wherein D-tryptophan is administered to the subject in an amount sufficient to increase the serum level of D-tryptophan.

14. The method according to claim 9, wherein D-tryptophan is capable of altering the gut microbiota in a subject upon administration.

15. The method according to claim 9, wherein D-tryptophan administration to the subject is oral, intravenous, subcutaneous, parenteral, transdermal, intraperitoneal, intramuscular or pulmonary administration.

16. The method according to claim 9, wherein D-tryptophan modulates the immune response and/or alters the gut or lung microbiota in the subject upon administration.

17. The method according to claim 16, wherein modulating the immune response comprises increasing $T_{reg}$ cells in the lung and/or in the gut, reducing $T_H2$ cells in the lung and/or reducing IL-4, Gata3 and IL-13 T cell secretion in the subject compared to a subject who has not been treated with D-tryptophan.

18. The method according to claim 16, wherein modulating the immune response comprises reducing number of dendritic cells expressing costimulatory molecules; increasing secretion of IL-10 of dendritic cells and/or decreasing secretion of IFN-g, IL-12 and IL-5 of dendritic cells of the subject compared to a subject who has not been treated with D-tryptophan.

19. The method according to claim 16, wherein altering the gut or lung microbiota in the subject is increasing gut or lung microbiota diversity in the subject, wherein abundance of Lachnospiraceae and Odoribacteraceae is increased, abundance of Rikenellaceae is decreased and/or abundance of Ruminococcaceae is restored in the subject to a level more comparable to a healthy subject.

20. The method according to claim 9, wherein D-tryptophan decreases the number of bronchoalveolar lavage fluid cells in the subject, compared to a subject who has not been treated with D-tryptophan.

21. The method according to claim 11, wherein D-tryptophan decreases airway hyperreactivity in the subject, compared to a subject who has not been treated with D-tryptophan.

* * * * *